United States Patent
Greenblatt et al.

(10) Patent No.: US 11,875,415 B2
(45) Date of Patent: *Jan. 16, 2024

(54) SYSTEM FOR PRE-ADJUDICATING AND MODIFYING DATA PACKETS IN HEALTH CLAIM PROCESSING SYSTEM

(71) Applicant: FLIPT, LLC, Jersey City, NJ (US)

(72) Inventors: Aaron Greenblatt, Jersey City, NJ (US); Lev Peysekhman, Freehold, NJ (US)

(73) Assignee: Flipt, LLC, Jersey City, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/129,272

(22) Filed: Mar. 31, 2023

(65) Prior Publication Data

US 2023/0289889 A1    Sep. 14, 2023

Related U.S. Application Data

(63) Continuation of application No. 16/681,139, filed on Nov. 12, 2019, now Pat. No. 11,663,669.

(60) Provisional application No. 62/760,890, filed on Nov. 13, 2018.

(51) Int. Cl.
  *G06Q 40/08*   (2012.01)
  *G06Q 30/0207*   (2023.01)
  *G16H 20/10*   (2018.01)
  *G16H 10/60*   (2018.01)

(52) U.S. Cl.
  CPC .......... *G06Q 40/08* (2013.01); *G06Q 30/0224* (2013.01); *G16H 10/60* (2018.01); *G16H 20/10* (2018.01)

(58) Field of Classification Search
  CPC ................................................ G06Q 50/22–26
  See application file for complete search history.

(56) References Cited

U.S. PATENT DOCUMENTS

| | | |
|---|---|---|
| 6,067,524 A | 5/2000 | Byerly et al. |
| 6,820,058 B2 | 11/2004 | Wood et al. |
| 6,915,254 B1 | 7/2005 | Heinze et al. |
| 7,006,983 B1 | 2/2006 | Packes et al. |
| 7,246,068 B2 | 7/2007 | Thomas |
| 7,552,061 B2 | 6/2009 | Richmond |

(Continued)

OTHER PUBLICATIONS

Office Action for U.S. Appl. No. 16/590,241, dated Aug. 6, 2021; 19 pps.

(Continued)

*Primary Examiner* — Neal Sereboff
(74) *Attorney, Agent, or Firm* — Rowan Tree Law Group, PLLC; Magdalena M. Fincham

(57) ABSTRACT

In accordance with some embodiments, an alternative system for processing a data packet received via a secure pharmacy prescription claim network is provided, in which data included in the data packet as received from a pharmacy system is modified prior to being routed to a PBM. The data packet may be modified such that a first BIN/PCN is replaced by a second BIN/PCN and a Consumer Price is added. The alternative system allows for a third party to act as a switchboard for prescription claims such that requests for prescription claims received from pharmacy systems are pre-adjudicated and data packets included in the requests are modified prior to being routed to a PBM selected by the third party.

17 Claims, 15 Drawing Sheets

(56) References Cited

U.S. PATENT DOCUMENTS

| | | |
|---|---|---|
| 7,566,000 B2 | 7/2009 | Agostino et al. |
| 7,596,578 B1 | 9/2009 | Marks |
| 7,657,437 B2 | 2/2010 | Kalies |
| 7,677,601 B2 | 3/2010 | Garett |
| 7,702,530 B2 | 4/2010 | Pearson |
| 7,739,127 B1 | 6/2010 | Hall |
| 7,769,601 B1 | 8/2010 | Bleser et al. |
| 7,885,836 B2 | 2/2011 | Pendleton et al. |
| 7,912,741 B1 | 3/2011 | Pinsonneault |
| 8,032,397 B2 | 10/2011 | Lawless |
| 8,050,943 B1 | 11/2011 | Wiley et al. |
| 8,095,381 B2 | 1/2012 | Simons et al. |
| 8,099,300 B2 | 1/2012 | Gourley |
| 8,099,303 B1 | 1/2012 | Battaglia et al. |
| 8,165,895 B2 | 4/2012 | Nadas et al. |
| 8,190,453 B2 | 5/2012 | Rowe et al. |
| 8,204,781 B2 | 6/2012 | Solomon et al. |
| 8,219,422 B2 | 7/2012 | Hallberg |
| 8,249,897 B2 | 8/2012 | Yamaga et al. |
| 8,265,953 B2 | 9/2012 | Elizabeth et al. |
| 8,301,493 B2 | 10/2012 | Sanders et al. |
| 8,335,695 B2 | 12/2012 | Cedergreen |
| 8,341,015 B2 | 12/2012 | Harrell |
| 8,392,209 B1 | 3/2013 | Bertha et al. |
| 8,412,538 B2 | 4/2013 | Hardaway |
| 8,433,590 B2 | 4/2013 | Prescott |
| 8,458,022 B2 | 6/2013 | Bous |
| 8,489,417 B2 | 7/2013 | Hoffman et al. |
| 8,521,550 B2 | 8/2013 | Mindala |
| 8,527,300 B2 | 9/2013 | Jackson et al. |
| 8,566,129 B1 | 10/2013 | Schwarz |
| 8,571,889 B2 | 10/2013 | Ashford |
| 8,620,830 B2 | 12/2013 | Melnick et al. |
| 8,630,873 B1 | 1/2014 | Wiley et al. |
| 8,635,083 B1 | 1/2014 | Casu |
| 8,635,089 B1 | 1/2014 | Mahoney et al. |
| 8,639,523 B1* | 1/2014 | Pinsonneault ......... G16H 20/10 |
| | | 705/2 |
| 8,712,797 B1 | 4/2014 | Bezdek et al. |
| 8,719,078 B1 | 5/2014 | McRae et al. |
| 8,738,399 B1 | 5/2014 | Nader et al. |
| RE45,006 E | 7/2014 | Deaton et al. |
| 8,781,851 B2 | 7/2014 | Anderson et al. |
| 8,788,282 B2 | 7/2014 | Watanabe |
| 9,786,023 B2 | 10/2017 | Cohan et al. |
| 9,846,914 B1 | 12/2017 | Murray et al. |
| 10,235,729 B1 | 3/2019 | Cedergreen et al. |
| 10,373,255 B1 | 8/2019 | Cedergreen |
| 10,402,839 B1 | 9/2019 | Frazee et al. |
| 10,417,380 B1 | 9/2019 | Kaye et al. |
| 10,438,693 B1 | 10/2019 | Vandervoort et al. |
| 10,482,476 B2 | 11/2019 | Morsa |
| 10,489,552 B2 | 11/2019 | Pinsonneault |
| 10,541,049 B2 | 1/2020 | Shutko et al. |
| 10,713,694 B1 | 7/2020 | Harris et al. |
| 10,719,839 B2 | 7/2020 | Smeeding et al. |
| 10,748,227 B2 | 8/2020 | Drzewucki et al. |
| 10,817,920 B2 | 10/2020 | Begley et al. |
| 10,922,687 B2 | 2/2021 | Mahaffey et al. |
| 2001/0029464 A1 | 10/2001 | Schweitzer |
| 2001/0032124 A1 | 10/2001 | Savage et al. |
| 2001/0037216 A1 | 11/2001 | Oscar et al. |
| 2002/0055856 A1 | 5/2002 | Adams |
| 2002/0087444 A1 | 7/2002 | DiPiero et al. |
| 2002/0103680 A1 | 8/2002 | Newman |
| 2002/0188476 A1 | 12/2002 | Bienvenu et al. |
| 2003/0033532 A1 | 2/2003 | Marks |
| 2003/0036923 A1 | 2/2003 | Waldon et al. |
| 2003/0055687 A1 | 3/2003 | Rudy |
| 2003/0074234 A1 | 4/2003 | Stasny |
| 2003/0195773 A1 | 10/2003 | Mahaffey |
| 2003/0230610 A1 | 12/2003 | Cyr-Hasty et al. |
| 2004/0006490 A1 | 1/2004 | Gingrich et al. |
| 2004/0078235 A1 | 4/2004 | Tallal |
| 2004/0138950 A1 | 7/2004 | Hyman et al. |
| 2004/0230502 A1 | 11/2004 | Fiacco et al. |
| 2005/0065850 A1 | 3/2005 | Mitchell et al. |
| 2005/0187821 A1 | 8/2005 | Lapsker |
| 2005/0187822 A1 | 8/2005 | Lapsker |
| 2005/0240442 A1 | 10/2005 | Lapsker |
| 2005/0261939 A1* | 11/2005 | Augspurger ........... G06Q 10/10 |
| | | 705/2 |
| 2005/0288966 A1 | 12/2005 | Young |
| 2006/0020514 A1 | 1/2006 | Yered |
| 2006/0026041 A1 | 2/2006 | Ullman |
| 2006/0129426 A1 | 6/2006 | Pearson |
| 2006/0184391 A1* | 8/2006 | Barre .................... A61K 8/732 |
| | | 705/2 |
| 2006/0190337 A1 | 8/2006 | Ayers et al. |
| 2006/0212345 A1 | 9/2006 | Soza et al. |
| 2006/0224443 A1 | 10/2006 | Soza et al. |
| 2006/0290886 A1 | 12/2006 | Santos |
| 2007/0027712 A1 | 2/2007 | Lapsker |
| 2007/0050210 A1 | 3/2007 | Wiley |
| 2007/0067218 A1 | 3/2007 | Bingham |
| 2007/0239487 A1 | 10/2007 | Abraham-Fuchs et al. |
| 2007/0250341 A1 | 10/2007 | Howe et al. |
| 2008/0154635 A1 | 6/2008 | Babyak et al. |
| 2008/0154759 A1 | 6/2008 | Babyak et al. |
| 2008/0183492 A1 | 7/2008 | Warren et al. |
| 2008/0215361 A1 | 9/2008 | Nunnari et al. |
| 2008/0313103 A1 | 12/2008 | Burns et al. |
| 2009/0094055 A1 | 4/2009 | Gage, Jr. et al. |
| 2009/0228302 A1 | 9/2009 | Rothschild |
| 2009/0326977 A1 | 12/2009 | Cullen et al. |
| 2010/0088108 A1 | 4/2010 | Machado |
| 2010/0096293 A1 | 4/2010 | Liebermann |
| 2010/0145798 A1 | 6/2010 | Richards |
| 2010/0241445 A1 | 9/2010 | Rago et al. |
| 2011/0015978 A1 | 1/2011 | Welch |
| 2011/0054935 A1 | 3/2011 | Hardaway |
| 2011/0054994 A1 | 3/2011 | Kelly |
| 2011/0099028 A1 | 4/2011 | van der Veen et al. |
| 2011/0106593 A1 | 5/2011 | Schoenberg |
| 2011/0153342 A1 | 6/2011 | Rose |
| 2011/0160544 A1 | 6/2011 | Hayter |
| 2011/0184796 A1 | 7/2011 | Miceli et al. |
| 2012/0136809 A1 | 5/2012 | Cannata et al. |
| 2012/0185263 A1 | 7/2012 | Emert |
| 2012/0278165 A1 | 11/2012 | Mercuri et al. |
| 2012/0284048 A1 | 11/2012 | Baym et al. |
| 2013/0054261 A1 | 2/2013 | Dufour |
| 2013/0090993 A1 | 4/2013 | Taylor et al. |
| 2013/0103465 A1 | 4/2013 | Meralli |
| 2013/0144646 A1 | 6/2013 | Loncar |
| 2013/0144649 A1 | 6/2013 | Kalies |
| 2013/0151281 A1* | 6/2013 | Kaburick ............... G06Q 10/10 |
| | | 705/2 |
| 2013/0179179 A1 | 7/2013 | Patra |
| 2013/0222116 A1* | 8/2013 | Barry, III ............... G16H 40/20 |
| | | 340/10.1 |
| 2014/0006048 A1 | 1/2014 | Liberty |
| 2014/0025471 A1 | 1/2014 | Bradley et al. |
| 2014/0039911 A1 | 2/2014 | Iyer |
| 2014/0067406 A1 | 3/2014 | Hyatt et al. |
| 2014/0081668 A1 | 3/2014 | Cunningham et al. |
| 2014/0100864 A1 | 4/2014 | Matosich |
| 2014/0100871 A1 | 4/2014 | Toleti et al. |
| 2014/0244546 A1 | 4/2014 | Bezdek et al. |
| 2014/0214435 A1 | 7/2014 | Previdi |
| 2014/0244281 A1 | 8/2014 | Smith |
| 2014/0244288 A1 | 8/2014 | Goodman |
| 2014/0278541 A1 | 9/2014 | Cassidy et al. |
| 2014/0297298 A1 | 10/2014 | Rago |
| 2014/0316796 A1 | 10/2014 | Cox |
| 2015/0095055 A1 | 4/2015 | Bagull |
| 2015/0142479 A1 | 5/2015 | Porter et al. |
| 2015/0154668 A1 | 6/2015 | Bezdek et al. |
| 2015/0161687 A1 | 6/2015 | Kehayes et al. |
| 2015/0178685 A1 | 6/2015 | Krumel et al. |
| 2015/0206262 A1 | 7/2015 | Pinsonneault et al. |
| 2015/0234991 A1 | 8/2015 | Pinsonneault |
| 2015/0254428 A1 | 9/2015 | Burkett |
| 2015/0278472 A1 | 10/2015 | King et al. |

(56) References Cited

U.S. PATENT DOCUMENTS

| | | |
|---|---|---|
| 2015/0370981 A1 | 12/2015 | Nuckolls et al. |
| 2016/0019354 A1 | 1/2016 | Grant et al. |
| 2016/0034668 A1* | 2/2016 | Rourke ............ G16H 10/60 705/2 |
| 2016/0103975 A1 | 4/2016 | Gairani et al. |
| 2016/0110511 A1 | 4/2016 | Momita |
| 2016/0154946 A1 | 6/2016 | Rubsamen |
| 2016/0321411 A1 | 11/2016 | Wiley |
| 2016/0358293 A1 | 12/2016 | Berger et al. |
| 2016/0358294 A1 | 12/2016 | Berger et al. |
| 2017/0017760 A1 | 1/2017 | Freese et al. |
| 2017/0039331 A1 | 2/2017 | Bezdek et al. |
| 2017/0091416 A1 | 3/2017 | Mink et al. |
| 2017/0161458 A1 | 6/2017 | Rourke et al. |
| 2017/0185724 A1 | 6/2017 | Darling |
| 2017/0220768 A1 | 8/2017 | Tanner et al. |
| 2017/0255759 A1 | 9/2017 | McGrath |
| 2017/0345060 A1 | 11/2017 | Janin et al. |
| 2018/0012244 A1 | 1/2018 | Leonardi |
| 2018/0121621 A1 | 5/2018 | Wiley |
| 2018/0233219 A1 | 8/2018 | Cathcart et al. |
| 2018/0293358 A1 | 10/2018 | Sooudi et al. |
| 2019/0252049 A1 | 8/2019 | Fotsch et al. |
| 2019/0279242 A1 | 9/2019 | Welch |
| 2019/0304021 A1 | 10/2019 | Rutherford et al. |
| 2019/0370845 A1* | 12/2019 | Peysekhman ............ G06Q 40/08 |
| 2019/0371444 A1 | 12/2019 | Glass et al. |
| 2019/0385722 A1 | 12/2019 | Wiley |
| 2020/0027547 A1 | 1/2020 | Darling |
| 2020/0043035 A1 | 2/2020 | Peysekhman et al. |
| 2020/0160957 A1* | 5/2020 | Key ............ G06Q 40/08 |
| 2020/0302445 A1 | 9/2020 | Docken |
| 2020/0402017 A1 | 12/2020 | Davydov |
| 2020/0410618 A1 | 12/2020 | Solakhyan et al. |
| 2021/0074401 A1 | 3/2021 | Bezdek et al. |
| 2021/0090116 A1 | 3/2021 | Marks |

OTHER PUBLICATIONS

Office Action for U.S. Appl. No. 16/542,106, dated Jun. 24, 2021; 16 pps.

Final Office Action for U.S. Appl. No. 16/542,106, dated Oct. 8, 2021; 21 pps.

Written Opinion for PCT/US2018/033005 dated Oct. 11, 2018; 5 pps.

International Search Report for PCT/US2018/033005 dated Oct. 11, 2018; 2 pps.

International Preliminary Report and Patentability for PCT/US2018/033005 dated Nov. 28, 2019; 6 pps.

Final Office Action for U.S. Appl. No. 16/590,241, dated Jan. 24, 2022; 21 pps.

Office Action for U.S. Appl. No. 16/590,241, dated Aug. 17, 2022; 22 pps.

Office Action for U.S. Appl. No. 16/542,106, dated Apr. 11, 2022; 23 pps.

Final Office Action for U.S. Appl. No. 16/542,106, dated Oct. 20, 2022; 21 pps.

"Congress" (115th Congress 2d Session S.2582; Mar. 21, 2018; pp. 15, 16; link at: https://www.congress.gov/115/bills/s2582/ BI LLS-115s2582is.pdf.

Office Action for U.S. Appl. No. 16/681,139 dated Oct. 15, 2021; 18 pps.

Final Office Action for U.S. Appl. No. 16/681,139 dated Apr. 25, 2022; 15 pps.

Office Action for U.S. Appl. No. 16/681,139 dated Nov. 14, 2022; 15 pps.

Notice of Allowance for U.S. Appl. No. 16/681,139 dated Feb. 3, 2023; 7 pps.

NPCC and Pharmacy Benefit Consultants, "Manufacturers Are Using "Switch Operators" to Undermine Your Plan's Cost Saving Efforts" (Year: 2014).

ERX Network, "Connect" As downloaded from https://web.archive.or/web20010501000000/https://erxnetwork.com (Year: 2001).

Office Action for U.S. Appl. No. 16/542,106, dated Feb. 28, 2023; 24 pps.

* cited by examiner

1900A

SYSTEM FOR PRE-ADJUDICATING AND MODIFYING DATA PACKETS IN HEALTH CLAIM PROCESSING SYSTEM

CLAIM OF PRIORITY

The present Application is a Continuation Application of U.S. application Ser. No. 16/681,139 filed Nov. 12, 2019 in the name of Greenblatt et al. and titled SYSTEMS FOR PRE-ADJUDICATING AND MODIFYING DATA PACKETS IN HEALTH CLAIM PROCESSING SYSTEM, which Application claims the benefit of U.S. Provisional Application No. 62/760,890 filed in the name of Peysekhman et al. on Nov. 13, 2018 and titled SYSTEM FOR FACILITATING HEALTHCARE EXPENDITURES. The entirety of each of these Applications is incorporated by reference herein for all purposes.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND

The process of filling a prescription at a pharmacy involves a complicated process involving a well-established infrastructure that involves several entities, in which the pharmacy transmits a data packet defining a prescription that a consumer is requesting to fill and receiving an approval or denial of the request, all within a secure and specialized network (e.g., eRx Network™) for transmitting such prescription claim requests and responses. While various attempts have been made at providing new processes that have the potential of providing savings to consumers on their prescriptions, these processes rely on pharmacies changing their well-established processes and/or changing the underlying infrastructure for processing and adjudicating requests for prescription claims, which limits the desirability, efficiency and accessibility of such solutions. Additionally, many such solutions require a consumer to make the difficult choice of going through the established infrastructure of prescription fulfillment and having their prescription go through their prescription plan of their chosen health benefit plan or trying to find an alternate mechanism for savings that is outside their prescription plan.

Pharmaceutical prescription costs have been dramatically increasing over the past many years and are expected to continue to do so. Even persons covered by a pharmacy benefit insurance plan (also referred to as a prescription plan or prescription benefit plan herein) and/or health insurance plans continue, year-over-year, to pay increasingly higher prices for each prescription they fill. Prescription costs continue to increase for reasons such as the co-pay amounts escalating, prescriptions not being covered by pharmacy benefit plans or counting towards an insured's out-of-pocket portion of the plan due to increasing prices even within a pharmacy benefit plan network.

One reason for the high cost of prescription drugs is that the savings that result from rebate or discount agreements that are entered into between prescription drug manufacturers and Pharmacy Benefit Managers ("PBMs") or other entities are not nearly often enough passed on to the plan holders/consumers. PBMs are third party administrators of pharmacy benefit plans that work with pharmacies, pharmaceutical drug manufacturers and pharmaceutical benefit plan providers to negotiate discounts and rebates for prescription drugs and process claims for prescription drug claims and reimburse pharmacies for prescriptions filled by the pharmacies. Unfortunately, the end user or consumer that ultimately purchases the prescription drug often does not realize the benefits of any discounts negotiated with the retailers or rebates negotiated with the drug's manufacturer. Further, PBMs often add significant spreads to the cost of generic prescription drugs; in Applicant's estimation, generic drugs are marked up nearly 600% on average from the time they leave the manufacturer's premise until the time they are reimbursed by some combination of plan sponsor and plan member.

Applicant has recognized that there is a long-standing need for a prescription drug redemption system that results in lower prescription drug prices to ends users or consumers and that works within the framework of the long-standing systems and processes for how prescription drugs are sold by pharmacies and for which pharmacies are reimbursed after filling a prescription. Lower prescription drug costs to consumers will result in various benefits, such as a greater adherence to a medical treatment plan (since many consumers report that the primary reason for not filling or re-filling a prescription is the high cost to the consumer when filling the prescription) and cost savings to employers or other health plan providers. Applicant has further recognized that pharmacies operate within a long-standing prescription redemption infrastructure that should be largely maintained in order to minimize any disruptions or modifications to the systems and processes of the many pharmacies throughout the country that rely on such infrastructure. Accordingly, Applicant has invented embodiments which, working within the current prescription redemption infrastructure relied upon by pharmacies, provides for Applicant's inventive system to process and modify data packets such that, while allowing a consumer to realize lower prices, results in minimal disruption and/or modification to pharmacies' current processes such that the insertion of Applicant's system and processes into the current infrastructure appears essentially transparent to the pharmacies.

BRIEF DESCRIPTION OF THE FIGURES

An understanding of embodiments described herein and many of the attendant advantages thereof may be readily obtained by reference to the following detailed description when considered with the accompanying drawings, wherein.

DETAILED DESCRIPTION

Figure 1:
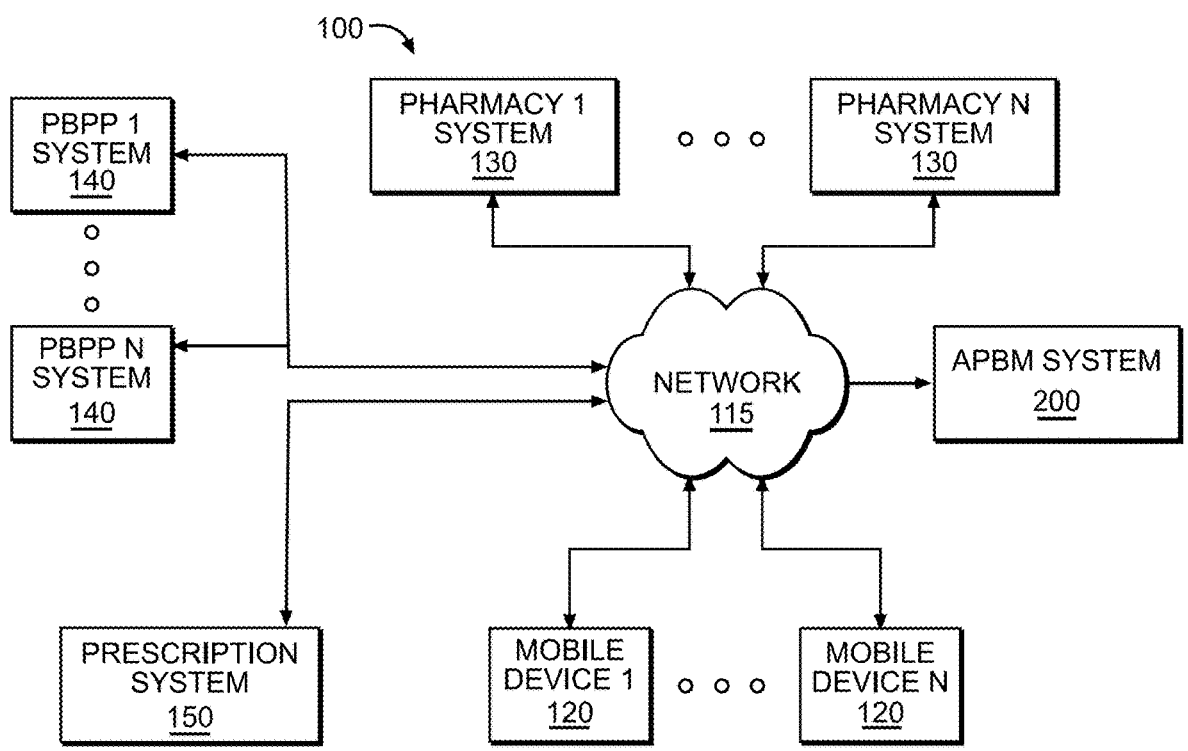
FIG. 1 is a block diagram of a system consistent with at least some embodiments described herein.

The filling of prescriptions by consumers is currently a stressful and opaque process for the consumers (the persons for whom the prescriptions are provided by healthcare providers). The costs to consumers and pharmacy benefit providers (whether these be employers, corporate employers, health plans, labor unions, government entities and other organizations, collectively "Pharmacy Benefit Plan Providers" or PBPPs herein; also sometimes collectively referred to as "employers" herein) has been rapidly and continually increasing over many years. In accordance with some embodiments, PBPPs may also include employers or other healthcare benefit plan provider that provide healthcare benefits other than pharmacy benefits (e.g., healthcare provider benefits, treatment or diagnostic test benefits, etc.). The pricing of pharmaceutical drugs (in terms of the price the consumer ends up paying out-of-pocket for obtaining the drug, referred to as a Consumer Price herein) is a convoluted process that involves confidential contracts between the various pharmacies that fill the prescriptions and the Pharmacy Benefit Managers (PBMs) that administer pharmacy benefit plans on behalf of PBPPs, with the result being that the same pharmaceutical drug can have different Consumer Prices at different pharmacies. Under current practices, neither consumers nor PBPPs have ready access to the pricing information for different available pharmacies such that they can effectively accept and lock in a price for filling the prescription drug at a first pharmacy and thus realize the potential cost savings of having a prescription filled at the first pharmacy rather than a second pharmacy. Embodiments described herein provide consumers with an effective mechanism for comparing Consumer Prices at different pharmacies (and, in some embodiments, earning rewards) and obtaining the lowest available price while still going through their health insurance and pharmacy benefit plan such that the Consumer Price they pay is applied towards their deductible.

It should be noted that under the current prescription drug fulfillment system that involves PBMs managing and facilitating the fulfillment of prescriptions as a middleman between the PBPP, the consumer and the pharmacies, there are different monetary values exchanged between the various involved entities, which further obfuscates to the consumer whether he/she could be paying less for the prescription. The various monetary amounts involved in the fulfillment of a prescription are described below, for purposes of background information that sets forth the need for the invention(s) described herein.

A first monetary value involved in the fulfillment of a prescription is the monetary value a pharmacy has paid for obtaining the pharmaceutical drug (e.g., directly from the drug manufacturer or from a wholesaler) such that it has it in inventory and available for fulfillment of prescriptions. The monetary value that a pharmacy has paid for obtaining a pharmaceutical drug (whether a generic or brand version) is referred to as a Drug Cost herein.

A second monetary value involved in the fulfillment of a prescription is the monetary value a pharmacy is paid by a PBM upon filling the prescription. The PBM that administers the consumer's pharmacy benefit plan on behalf of the consumer's PBPP has different pricing agreements with different pharmacies (e.g., WALMART™ vs. CVS™). A pricing agreement, that defines prices for different drugs that the PBM will cover and reimburse the pharmacy for, is agreed to between a pharmacy company and a PBM (often referred to as a Pharmacy Participation Agreement, or "PPA" herein). For generic drugs, the pricing agreement typically defines the parameters and aggregate discounts rates that are used to develop the respective Maximum Allowable Cost ("MAC") for each generic pharmaceutical drug that the PBM will reimburse the pharmacy upon fulfillment of a prescription. Typically, MAC lists are published monthly and show the current MAC value for each generic pharmaceutical drug, per PBM. Sometimes, a pharmacy is reimbursed less than the MAC Pharmacy Reimbursement Amount for the various pharmaceutical drugs dispensed by the pharmacy and for which the pharmacy is reimbursed by the PBM. A Pharmacy Reimbursement Amount for a particular pharmaceutical drug, as the term is used herein unless indicated otherwise, is the monetary value a particular pharmacy is paid by a particular PBM (or the system of the present invention, as described herein) upon fulfillment of a prescription for that pharmaceutical drug (whether it is a MAC list price or otherwise and likely includes a fixed fulfillment fee per prescription).

The Pharmacy Reimbursement Amounts owed to a pharmacy by a PBM are often provided to a pharmacy in bulk at periodic intervals. For example, once per month or once per fiscal quarter a PBM will transmit payment to a PBM of all the Pharmacy Reimbursement Amounts it owes the pharmacy for prescriptions filled by the pharmacy under a pricing agreement between the PBM and the pharmacy, along with a transaction log that shows the particular Pharmacy Reimbursement Amount owed and what transaction it pertains to. A unique transaction identifier is assigned to a prescription fulfillment request when it is submitted to the PBM by a pharmacy when a consumer is at the pharmacy to fill the prescription and the transaction log references this unique transaction identifier along with the amount being paid to the pharmacy by the PBM for that transaction.

It should be noted that in many cases there may be a brand version and/or multiple generic versions that are suitable for fulfillment of a particular prescription. Each such generic version (and the brand version) may be considered a respective pharmaceutical drug for purposes of the present description and have a respective Pharmacy Reimbursement Amount associated therewith in the pricing contracts of a PBM (sometimes multiple Pharmacy Reimbursement Amounts if different pharmacies have negotiated different Pharmacy Reimbursement Amounts for the same pharmaceutical drug). It should be noted that a pharmacy may receive other payments in exchange for filing a prescription (e.g., a transaction fee for each prescription filled). Further, if the consumer has a co-pay associated with his/her pharmacy benefit plan, the pharmacy may also collect this co-pay, which may be forwarded to the PBM by the pharmacy or credited against the Pharmacy Reimbursement Amount owed to the pharmacy by the PBM.

A third monetary value involved in the fulfillment of a prescription is the monetary value paid by the consumer's PBPP or employer to the PBM. Each PBM has a pricing schedule as part of its agreement with the PBPP or employer of the consumer, the pricing schedule defining a respective PBM Price for each pharmaceutical drug. A PBM Price, as the term is used herein, is the price a PBPP has to pay to a PBM once the PBM facilitates the fulfillment of the corresponding prescription drug at a particular pharmacy. Often, the PBPP or employer does not know what the Pharmacy Reimbursement Amount is set at as between a pharmacy and the PBM for a given pharmaceutical drug, it only knows the PBM Price for the drug as per its pricing schedule with the PBM. Typically a PBM profits significantly by including a substantial mark-up between the PBM Price of a particular pharmaceutical drug (i.e., what the PBM charges for the drug to the PBPP) and the Pharmacy Reimbursement Amount for the drug (i.e., what the PBM pays to a pharmacy for that drug). Depending on the PBMs pricing contracts with different pharmacies, that price differential can vary significantly. A PBM may further profit by collecting rebates from a drug manufacturer of a pharmaceutical drug (this being particularly true for brand drugs) but not passing any, or most, of that rebate on to the PBPP (e.g., in the form of a reduced PBM Price).

A fourth monetary value involved in the fulfillment of a prescription is the monetary value a consumer ultimately pays for filling a prescription for a pharmaceutical drug and is referred to as a Consumer Price herein. A Consumer Price may, in some embodiments, be a co-pay amount (e.g., after a deductible threshold is met for the consumer's pharmacy benefit plan), the PBM Price (e.g., before a deductible threshold is met for the consumer's pharmacy benefit plan) or another amount. In the current complex and obfuscated environment of prescription fulfillment, consumers end up paying for a pharmaceutical drug based on the PBM Price of the drug (e.g., directly, in the deductible term of their pharmacy benefit plan, or indirectly even after their deductible amount is met because co-pays and premiums are calculated partially on how much the PBPP is expecting to pay to its PBM). Due to the lack of transparency inherent in the conduct of the PBMs, neither consumers nor PBPPs realize full the benefits of any rebates and fees the PBM may be receiving from the drug manufacturer or the potential for savings as a result of filling the prescription at a pharmacy that has a lower Pharmacy Reimbursement Amount than a pharmacy that has a relatively higher Pharmacy Reimbursement Amount.

Applicant's invention(s) deduces the Pharmacy Reimbursement Amounts as between different PBMs and different pharmacies by analyzing a variety of data sources, as well as estimated rebates available to PBMs from brand pharmaceutical drug manufacturers, and leverages the generated pricing data for the benefit of both consumers and PBPPs, with the result being not only savings to the consumer and PBPP but also, in many circumstances, additional rewards being earned by the consumer. The system of Applicant's invention may also have its own pricing contracts that it negotiates directly with pharmacies, as a PBM would. Applicant's invention(s) provides an alternative to the conventional PBM model by providing an alternate mechanism that runs parallel to the PBM process or as an added node in the PBM process such that Applicant's system becomes akin to a switchboard for the PBMs, as (or as an alternate to the PBM process, for PBPPs or for consumers who may not have a pharmacy benefit plan).

In accordance with some embodiments, the invention(s) described herein outputs to a consumer who has been prescribed a pharmaceutical treatment (i.e., a prescription that can be filled with a brand or either a brand or at least one acceptable generic version of a drug, according to an acceptable formulary) a menu of offers, each offer defining a pharmacy location at which the prescription may be filled and a Consumer Price for each such location. The Consumer Price for each pharmacy location, in accordance with some embodiments, is based on the Pharmacy Reimbursement Amount for that pharmacy location (i.e., not on the PBM Price, which in the vast majority of circumstances will be significantly higher than the Pharmacy Reimbursement Amount), based on one or more pricing agreements with various available pharmacies. In some embodiments, such an offer may be for a pharmacy at which a consumer is located (e.g., a consumer may arrive at a pharmacy without first reviewing and accepting an offer to fill a prescription at a particular pharmacy and thus may be presented with an offer for the pharmacy at which the consumer is located at the time the request for the offer is submitted to the system).

In accordance with some circumstances (e.g., after a deductible threshold for the consumer's pharmacy benefit plan is met), a Reward Amount to be provided to the consumer may also be defined by one or more of the offers. A Reward Amount may be offered in order to incentivize the consumer to either use the system described herein (which system is referred to as the Alternate Pharmacy Benefit Manager system ("APBM" system)) rather than the traditional PBM's mechanism when the APBM system is running in parallel with the PBM and its prices are lower, or fill the prescription at a pharmacy location that, while less convenient for the consumer, has a relatively lower Pharmacy Reimbursement Amount and will thus be less costly for the consumer's PBPP. The APBM system(s) described herein provide an alternative to PBPPs as well as to consumers, by inserting itself as an alternate middleman (alternate to the PBM) between the PBPP and the pharmacy. In accordance with embodiments described herein, the APBM system allows the PBPP to only pay the Pharmacy Reimbursement Amount for prescriptions filled thereon (e.g., in exchange for the PBPP paying the APBM a relatively nominal fee (e.g., a per member per month fee or a per transaction fee) to the system) such that the PBPPs may realize the benefits of a consumer filling a prescription at a pharmacy that has a relatively lower Pharmacy Reimbursement Amount for the pharmaceutical drug with which the prescription is filled. The APBM system further allows for the consumer to realize these benefits for offering to the consumer a Reward Amount that is calculated or based on the differential between a PBM Price the PBPP would otherwise have to pay for the fulfillment of the prescription if the prescription fulfillment were to go through the conventional PBM process and the Pharmacy Reimbursement Amount. In accordance with some embodiments, the APBM system may provide the PBPP a choice as to what percentage or portion of this differential to include as a Reward Amount to the consumer (in other embodiments, this variable may be adjusted or set by the APBM, in some cases on a dynamic, transaction-by-transaction, customer-by-customer basis).

In accordance with some embodiments, a PBPP contractually agrees to provide APBM services to its plan members/consumers and in doing so provides specific information on its plan members and existing PBM plan to the APBM (e.g., a plan identifier). A consumer registers with an APBM prior to attempting to fill a prescription via the APBM system. The APBM system is thus able to obtain, update and utilize the specific information of a consumer's pharmacy benefit plan based on information obtained from the PBPP (e.g., co-pay amounts, deductible period and amount information, other consumers covered under the plan, the PBPP and PBM associated with the plan) when calculating and including the various data included in each offer output to the consumer (e.g., the Reward Amount and the Consumer Price).

In accordance with some embodiments, each offer further defines a Consumer Price for the pharmaceutical drug defined by the offer, which is the price the consumer is to pay the pharmacy for the pharmaceutical drug if the prescription is filled via the APBM system. The Consumer Price may comprise, for example: (i) a co-pay amount (e.g., if the prescription is being filled after a deductible period of the consumer's pharmacy benefit plan); (ii) a price based on the Pharmacy Reimbursement Amount (e.g., if the prescription is being filled during a deductible period of the consumer's pharmacy benefit plan); or (iii) the lower of the co-pay amount or the Pharmacy Reimbursement Amount of a given pharmacy location. In some embodiments, the menu of offers may also indicate to the consumer the PBM Price the consumer would pay if he/she were to fill the prescription via the traditional PBM route rather than using the APBM system (e.g., if the consumer is filling the prescription during a deductible period of their pharmacy benefits plan).

In accordance with some embodiments, once the consumer accepts the one or more offers and agrees to filling the prescription at the pharmacy location defined by the accepted offer, the consumer is guaranteed the Consumer Price defined by that offer (e.g., even if the APBM ends up having to pay a higher price to the pharmacy for the fulfillment of the consumer's prescription, as described in more detail below). In accordance with some embodiments, the consumer pays the Consumer Price to the APBM system, which then forwards that payment to the appropriate entity (e.g., the pharmacy location at which the prescription is filled). Thus, in such embodiments the consumer does not need to provide any payment to the pharmacy when filling the prescription at the pharmacy location defined by the offer. In other embodiments, the consumer may pay the Consumer Price to the pharmacy when picking up the prescription, as in traditional pharmacy transactions.

In accordance with some embodiments, the consumer is presented with one or more offers, and is able to accept an offer, via an app that is downloaded to the consumer's mobile device. Of course, a software application or online portal that is accessible via a desktop or other computing device may also be utilized.

Previous attempts at reducing the costs of prescription fulfillment have not addressed the consumer's need for a guaranteed price or price that can be relied upon, nor have they provided an opportunity for the PBPP and consumer to earn rewards and share in the cost savings when a consumer chooses to redeem a prescription at a pharmacy with a relatively low PBM price. Further, previous attempts at reducing the costs of prescription fulfillment have not been integrated with, or taken into account, a consumer's pharmacy benefit plan. Additionally, previous solutions have not been integrated with a claim processing system used by pharmacies to approve and process prescriptions, which allows a guaranteed price to be offered to a consumer at the point of sale.

Referring now to FIG. 1, illustrated therein is a functional block diagram of an example system 100, which is consistent with some embodiments. The system 100 includes an APBM System 200 which may, for example, by operated by or on behalf of an APBM in order to facilitate and/or manage the fulfilment of pharmaceutical prescriptions in accordance with at least some embodiments described herein. For example, the APBM System 200 may be operable to carry out one or more of the methods and/or functionalities described herein, such as (i) inferring, calculating or estimating, via one or more algorithms or protocols, the estimated Pharmacy Reimbursement Amount(s) for a particular pharmaceutical drug available via various pharmacies; (ii) identifying and maintaining an indication of PBM prices for various pharmaceutical drugs and/or pricing contracts negotiated between the APBM and various pharmacies; (iii) maintaining one or more formularies (a formulary being a schedule of which pharmaceutical drugs are acceptable substitutes for one another or a listing of pharmaceutical drugs that are approved to be prescribed under a particular pharmacy benefit plan); (iv) identifying the estimated rebate amount available for one or more brand pharmaceutical drug; (v) obtaining and maintaining account information for member consumers (persons who register with the APBM in order to receive offers for prescription fulfillment options), such information including pharmacy benefit plan information for each such consumer; (vi) generating offers in response to a consumer entering prescription data; maintaining and updating information on offers accepted by consumers (e.g., including a redemption status of each such offer); (vii) facilitating the collection of payment from consumers; (viii) facilitating the provision of Pharmacy Reimbursement Amounts to pharmacies based on accepted and redeemed offers; (ix) collecting payments from PBPPs (e.g., flat transaction fees for redeemed offers and/or payments of Pharmacy Reimbursement Amounts that have been paid, or that need to be paid, to pharmacies at which offers have been redeemed); and/or (x) modifying or altering a data packet received from a pharmacy (the data packet defining a transaction via which a consumer is requesting to fill a particular prescription at the pharmacy) prior to forwarding the data packet to a PBM corresponding to a pricing contract to be used in fulfilling the prescription.

In accordance with some embodiments, APBM System 200 may be operable to communicate, via a network 115, with (i) one or more mobile devices 120, devices of consumers or consumers participating in the APBM system described herein; (ii) one or more pharmacy computer systems 130; (iii) one or more PBPP systems 140; (iv) a commercial prescription claim processor 150 (e.g., Script-Claim™ or an appropriate equivalent thereon, which stores prescription information such that it can be retrieved by a pharmacy upon a consumer requesting to fill the prescription at the pharmacy).

As will be appreciated by one skilled in the art, aspects of the present disclosure and of any of the components of the system 100 (as well as system 500, described below) may be embodied as an apparatus that incorporates software, hardware, and/or firmware components. Any and all of the components of the system 100 and/or system 500 may be implemented as a system controller, a dedicated hardware circuit, an appropriately programmed general-purpose computer, or any other equivalent electronic, mechanical, or electro-mechanical device. Any or all of the components of the system 100 and/or system 500 may comprise, for example, one or more server computers operable to communicate with a plurality of computing devices (e.g., respective computing devices of PBPPs participating in the pharmaceutical prescription fulfillment program of the APBM and/or respective computing devices of one or more pharmacies participating in such program) and/or one or more additional devices such as a gateway server, router devices, or other devices for facilitating a pharmaceutical prescription fulfillment program as described herein.

The network 115 may comprise, for example, a mobile network such as a cellular, satellite, or pager network, the Internet, a wide area network, a Wi-Fi network, another network, or a combination of such networks. Although not shown in FIG. 1, other networks and devices may be part of system 100 and/or the network 1115 may comprise two or more networks operable to facilitate the routing of communications among the devices or components illustrated in FIG. 1. For example, in one embodiment, both a Wi-Fi network and a wireless cellular network may be involved in routing communications and/or transmitting data among two or more devices or components illustrated in FIG. 1.

The communication between any of the components of system 100, whether via the network 115 or otherwise, may take place over one or more of the following: the Internet, wireless data networks, such as 802.11 Wi-Fi, PSTN interfaces, cable modem DOCSIS data networks, or mobile phone data networks commonly referred to as 3G, LTE, LTE-advanced, etc.

In some embodiments, additional devices or components that are not show in FIG. 1 may be part of a system for facilitating an alternate pharmacy prescription fulfillment program as described herein. For example, one or more servers operable to serve as wireless network gateways or routers may be part of such a system. In other embodiments, some of the functionality described herein as being performed by system 200 may instead or in addition be performed by a third party server operating on behalf of the system 200 (e.g., the APBM may outsource some functionality, such as registration of new consumers or managing the redemption of rewards earned by consumers). Thus, a third party server may be a part of a system such as that illustrated in FIG. 1.

It should be understood that any of the functionality described herein as being performed by a particular component of the system 100 may in some embodiments be performed by another component of the system 100 and/or such a third party server. For example, one or more of the functions or processes described herein as being performed by APBM System 200 (e.g., a module or software application of the APBM System 200) or another component of system 100 may be implemented with the use of one or more cloud-based servers which, in one embodiment, may be operated by or with the help of a third party distinct from the APBM. In other words, while in some embodiments the APBM System 200 may be implemented on servers that are maintained by or on behalf of an APBM, in other embodiments it may at least partially be implemented using other arrangements, such as in a cloud-computing environment, for example.

Figure 2:
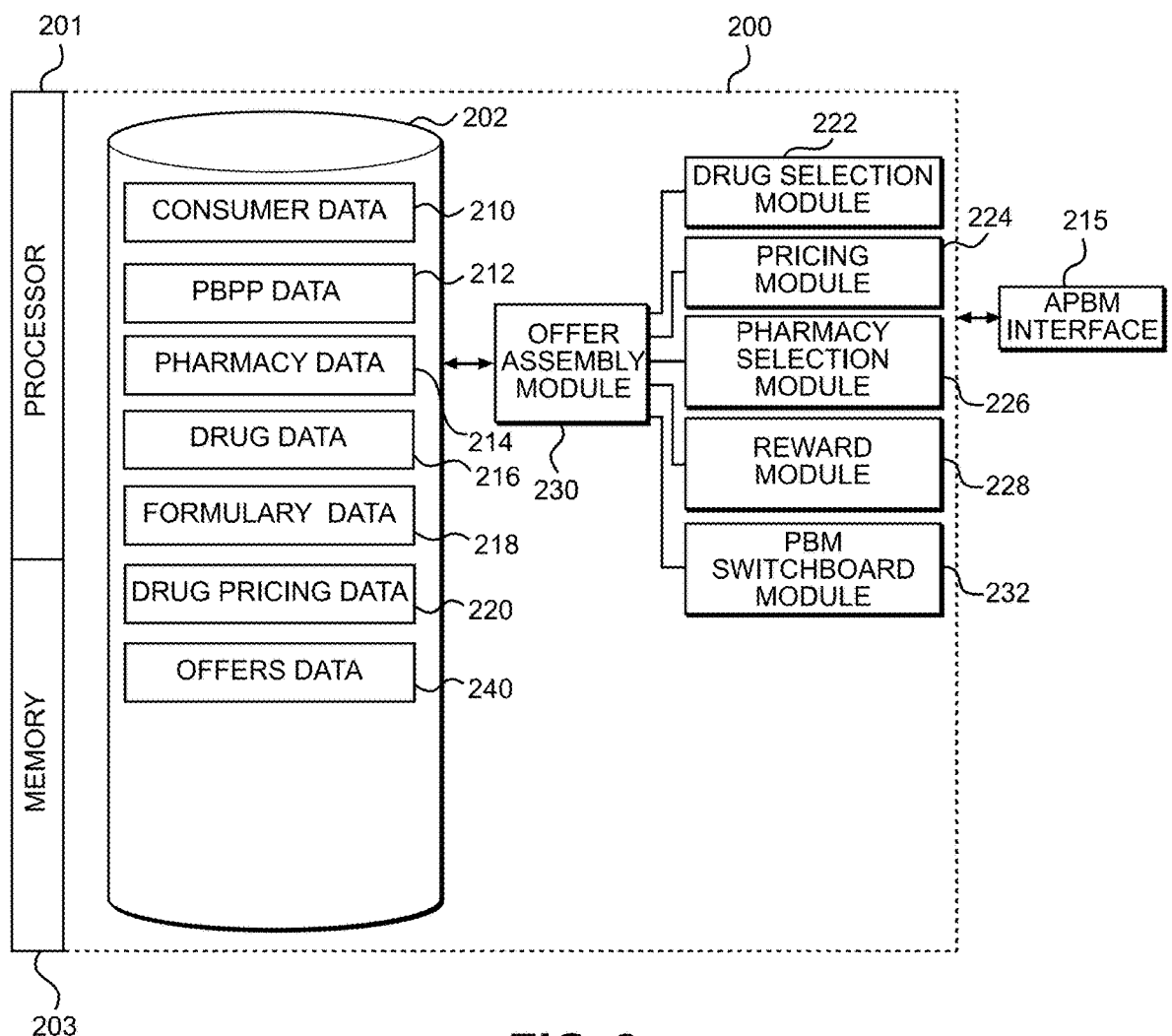
FIG. 2 is a block diagram of a system consistent with at least some embodiments described herein.

Turning now to FIG. 2, illustrated therein is an example of the APBM System 200 illustrated as being part of the system 100 of FIG. 1. The APBM System 200 may comprise, for example, a processor 201, a memory 203, a database 202 and a plurality of software modules 222-230.

In accordance with some embodiments, any or all of the components of the APBM System 200 may comprise one or more hardware components, such as microprocessors, microcontrollers, or digital sequential logic, etc., such as processor 201. The processor 201 may comprise one or more processors, such as one or more INTEL™ processors, working sequentially or in parallel. The processor 201 is in communication with, or operatively connected to, a memory 203. The memory 203 may comprise an appropriate combination of magnetic, optical, and/or semiconductor memory, and may include, for example, Random Access Memory (RAM), Read-Only Memory (ROM), a compact disc and/or a hard disk. The processor 201 and the memory 203 may each be, for example: (i) located entirely within a single computer or other device; or (ii) connected to each other by a remote communication medium, such as a serial port cable, telephone line or radio frequency transceiver. In one embodiment, the system 200 may comprise one or more devices that are connected to a remote server computer for maintaining databases.

The system 200 may further comprise a database 202, which may in some embodiments store data useful for implementing one or more embodiments described herein, non-limiting examples of which include (i) data associated with one or more consumers, (ii) data associated with one or more PBPPs; (iii) data associated with one or more pharmacies; (iv) data associated with one or more pharmaceutical drugs; and (iii) data associated with one or more offers generated by the APBM and accepted by a consumer (e.g., offers for which a consumer has paid the Consumer Price to the APBM). In accordance with some embodiments, the database 202 includes data, associated data structures, and database management software. The database 202 may, for example, be implemented using any well-known database management systems, including Microsoft SQL, Oracle, IBM DB2, etc. It should be noted that in some embodiments, database 202 (or at least some of the data described as being stored therein) may be stored in memory 203 and/or in another memory device accessible to the memory 203 and/or to processor 201. For example, in one embodiment database 202 (or at least some of the data described as being stored therein) may be stored in a memory of a third party server, such as a server of a cloud-based computing service with which the APBM may contract for purposes of storing data.

In some embodiments, the data described herein as being stored in database 202 may be stored across more than one database; the example data described herein as being useful in at least some embodiments is described as being stored in a single database 202 merely for purposes of simplicity. In accordance with some embodiments, one or more of the types of data 210-220 and 240 may be stored as a separate database (e.g., the pharmacy data 214 and the drug pricing data 218 may, in some embodiments, comprise a pharmacy database and a drug pricing database, respectively).

An example of a type of data that may be stored in database 202 includes consumer data 210 defining persons who have registered with the APBM in order to receive offers for fulfillment of pharmaceutical prescription. Such consumer data may include at least one of (i) information regarding the consumer's pharmacy benefit plan (if any), such as the co-pay amounts, deductible amount and current status, family members covered under the plan and pharmaceutical drugs covered under the plan; (ii) medical information of the consumer (e.g., allergies, medical conditions, other medications being taken); (iii) location information for selecting pharmacy locations to include in offers for the consumer (e.g., the consumer's home address or other preferred location, such as a work address); (iii) offers from the APBM accepted by the consumer (including redemption status thereof; alternatively this data may be stored in accepted offers data 232); (iv) payment information such as a preferred credit card to be charged for Consumer Prices of offers accepted by the consumer; and (v) rewards earned by the consumer based on accepted and/or redeemed offers (including redemption status of the reward(s); alternatively the rewards data may be stored separately). It should be noted that the information described herein as examples of the types of consumer data 210 may be stored in one or more related tables accessible to the APBM.

Another example of a type of data that may be stored in database 202 includes PBPP data 212 defining PBPPs that have agreed to participate in the pharmaceutical prescription fulfillment program of the APBM in accordance with at least some embodiments described herein. Such PBPP data may include at least one of: (i) an indication of the PBM utilized by the PBPP; (ii) a schedule of PBM prices the associated PBM charges to the PBPP; (iii) payment processing information (e.g., for processing invoices to the PBPP); and (iv) preferences of the PBPP (e.g., a preference for the percentage or portion of the differential between a PBM Price and a Pharmacy Reimbursement Amount to be provided to a consumer in the form of a reward).

Yet another example of a type of data that may be stored in database 202 includes pharmacy data 214 defining pharmacies that are available to be included in offers made by the APBM to consumers registered with the APBM. Such Pharmacy data may include, for one or more pharmacies, at least one of: (i) a geographical location of a pharmacy branch (e.g., to be utilized to calculate distance from a consumer's location, for purposes of selecting pharmacy locations to be included in offers made to consumers); (ii) a Pharmacy Reimbursement Amount for each of a plurality of pharmaceutical drugs available at the pharmacy, as contracted between the APBM and the pharmacy (e.g., in some embodiments the APBM may contract directly with partner pharmacies for specified Pharmacy Reimbursement Amounts for particular pharmaceutical drugs); (iii) a Pharmacy Reimbursement Amount for a plurality of PBMS for each of a plurality of pharmaceutical drugs available at the pharmacy (as it may be inferred or estimated by the PBM from various data sources, as described elsewhere herein); (iv) an indication of the particular generic version(s) of pharmaceutical drugs stocked by the pharmacy for a given medical condition or brand drug; (v) an indication of the Drug Cost to the pharmacy (which may be provided by the pharmacy to the APBM or inferred or deduced by the APBM from various sources, as described elsewhere herein); (vi) an indication of any incentives that the pharmacy is willing to offer to a consumer for selecting a particular pharmacy location; (v) an indication of payment processing information (e.g., for providing to the pharmacy the Pharmacy Reimbursement Amounts for prescriptions filled by the pharmacy in accordance with the terms of APBM offers accepted and redeemed by consumers).

Yet another example of the data that may be stored in database 202 is drug data 216 defining a list of prescription drugs and an indication of which generic pharmaceutical drugs are acceptable substitutes for one another or for a particular brand pharmaceutical drug. In one embodiment, the drug data may store the Generic Product Identifier (GPI) for each prescription drug. The GPI is a hierarchical classification system that comprises various data for prescription drugs in accordance with a particular code (e.g., the therapeutic class, dosage, strength, etc.). Other drug classification indicators that may be stored in drug data 216 include the American Society of Health-System Pharmacists (AHFS Drug Information) and First DataBank's Generic Sequence Number (GSN).

Yet another example of the data that may be stored in database 202 is formulary data 218. In some embodiments, a plurality of formularies may be stored (e.g., different formularies for different pharmacy benefit plans). A formulary may comprise a list of the prescription drugs approved or covered under a particular pharmacy benefit plan or by a particular PBM and the respective consumer co-pay amounts relative to each drug.

Yet another example of the data that may be stored in database 202 is drug pricing data 220 defining one or more prices or monetary values corresponding to a particular pharmaceutical drug. For example, the drug pricing data may include, for each drug, at least one of: (i) a Drug Cost (e.g., per pharmacy); (ii) a manufacturer's retail price or suggested retail price; (iii) a Pharmacy Reimbursement Amount (e.g., per pharmacy, per pharmacy-PBM agreement and/or per pharmacy-APBM agreement; in some embodiments this may comprise the MAC list price for each drug); (iii) a PBM price (e.g., per PBM); and (iv) an estimated rebate amount or brand discount factor for brand pharmaceutical drugs (e.g., an estimation based on a protocols, algorithms and/or peer review processes as described elsewhere herein).

Yet another example of the data that may be stored in database 202 is offers data 240 that defines one or more offers that (i) a consumer has accepted (e.g., and for which a digital code or electronic prescription fulfillment card has been generated and provided to a consumer); (ii) has been offered or output to a consumer (even if the consumer has not accepted the offer(s)); and (iii) offers or prescriptions that a consumer has searched for). In some embodiments, some or all of such data (e.g., offers rejected by a consumer, prescriptions searched for by a consumer) may alternatively be stored in consumer data 210). In accordance with some embodiments, data on consumer search history and offers they did not accept may be utilized by the APBM system to tailor offers to the consumer (or other consumers) for purposes such as more appropriately sizing the rewards required to incentivize acceptance of certain offers.

In accordance with some embodiments, a new record may be opened and populated in the accepted offers data 240 each time a consumer accepts an offer output by the APBM. Such records may be accessed and updated, for example, upon receiving a confirmation from a pharmacy that a consumer has redeemed an offer (i.e., filled a prescription in accordance with the terms of the offer). Each record may indicate, for example, (i) details of the prescription (e.g., drug name, dosage and quantity); (ii) the name on the prescription (e.g. the consumer's name or a name of a family member of the consumer that is registered with the APBM); (iii) the pharmacy location defined by the offer that the consumer has accepted; (iv) an indication of the Consumer Price; (v) an indication of the cost of the prescription to the PBPP; (vi) an indication of the reward corresponding to the offer; (vii) a unique identifier identifying the offer; (viii) an indication of the PBM to which the transaction defining the fulfillment request for a prescription was routed by the APBM (e.g., in accordance with the embodiments of FIGS. 5, 6B, 7 and 8); and (ix) some or all of the above corresponding to the offers the consumer did not select as a result of selecting this offer.

Thus, as described in accordance with some embodiments, an APBM pharmacy prescription fulfillment program may comprise an alternate option to consumers and PBPPs for fulfillment of pharmaceutical prescriptions that allows the PBPP and consumer to avoid the significant costs added to prescription fulfillment costs by PBMs and/or to realize the benefits of relatively lower Pharmacy Reimbursement Amounts accepted by one pharmacy over another. The program takes into account a consumer's pharmacy benefit plan (if any), lowers costs for the consumer as well as the PBPP and allows the consumer to be guaranteed a Consumer Price for a prescription upon accepting a corresponding offer even if the APBM is required to reimburse a pharmacy a higher price upon redemption of the offer. The APBM program, in accordance with at least some embodiments, infers or determines otherwise confidential Pharmacy Reimbursement Amounts contracted as between pharmacies and PBMs (or, in some embodiments, negotiates low Pharmacy Reimbursement Amounts directly with PBMs) and eliminates PBMs as a costly middleman in a pharmaceutical prescription fulfillment while maintaining the profits of pharmacies at an acceptable level and working within the parameters of a consumer's existing pharmacy benefit plan.

It should be noted that the examples provided herein of what type of information may be included in which type of example data should not be taken in a limiting fashion. Modifications can be made as to what type of information is stored with which type of data, different types of data may be combined, some information may be stored with more than one type of data, etc.

The system 200 may further comprise one or more software module(s) for directing the processor 201 to perform certain functions. In accordance with some embodiments, software components, applications, routines or subroutines, or sets of instructions for causing one or more processors to perform certain functions may be referred to as "modules". It should be noted that such modules, or any software or computer program referred to herein, may be written in any computer language and may be a portion of a monolithic code base, or may be developed in more discrete code portions, such as is typical in object-oriented computer languages. In addition, the modules, or any software or computer program referred to herein, may in some embodiments be distributed across a plurality of computer platforms, servers, terminals, and the like. For example, a given module may be implemented such that the described functions are performed by separate processors and/or computing hardware platforms.

With reference to FIG. 2, it should be understood that any of the software module(s) or computer programs illustrated therein may be part of a single program or integrated into various programs for controlling processor 201. Further, any of the software module(s) or computer programs illustrated therein may be stored in a compressed, uncompiled, and/or encrypted format and include instructions which, when performed by the processor 201, cause the processor 201 to operate in accordance with at least some of the methods described herein. Of course, additional and/or different software module(s) or computer programs may be included and it should be understood that the example software module(s) illustrated and described with respect to FIG. 2 are not necessary in any embodiments. Use of the term "module" is not intended to imply that the functionality described with reference thereto is embodied as a stand-alone or independently functioning program or application. While in some embodiments functionality described with respect to a particular module may be independently functioning, in other embodiments such functionality is described with reference to a particular module for ease or convenience of description only and such functionality may in fact be a part of integrated into another module, program, application, or set of instructions for directing a processor of a computing device.

According to an embodiment, the instructions of any or all of the software module(s) or programs described with respect to FIG. 2 may be read into a main memory from another computer-readable medium, such from a ROM to RAM. Execution of sequences of the instructions in the software module(s) or programs causes processor 201 to perform at least some of the process steps described herein. In alternate embodiments, hard-wired circuitry may be used in place of, or in combination with, software instructions for implementation of the processes of the embodiments described herein. Thus, the embodiments described herein are not limited to any specific combination of hardware and software. Some non-limiting examples of software module (s) that may be utilized in system 200 include: (i) a drug selection module 222; (ii) a pricing module 224; (iii) a pharmacy selection module 226; (iv) a reward calculation module 228; (v) an offer assembly module 230; and (vi) a PBM Switchboard module 232.

In the example embodiment illustrated in FIG. 2, offer assembly module 230 is illustrated as communicating with (i) a drug selection module 222; (ii) a pricing module 224; (iii) a pharmacy selection module 226; (iv) a reward module 228; and (v) a PBM Switchboard module 232. Any of (i) a drug selection module 222; (ii) a pricing module 224; (iii) a pharmacy selection module 226; (iv) a reward module 228; and (v) a PBM Switchboard module 232 may be operable to communicate with the database 202 (either directly or via the offer assembly module 230) and thus able to access or retrieve various data therefrom. Such an arrangement is illustrated as one example of how the data in database 202 may be accessed, modified and utilized.

Generally, the modules 222-232 should be understood as being accessible to processor 201, irrespective of how in particular they are arranged within the system 200, to implement one or more embodiments described herein. As described, one or more of the modules 222-232 may be operable to utilize at least some of the data stored in database 202. Further, in accordance with some embodiments, one or more of the modules 222-232 may be operable to retrieve, manipulate, select, update, modify and/or determine data that is transmitted to and stored in database 102.

Offer assembly module 230 may, in accordance with some embodiments, operate to manipulate the data from database 202 in order to generate a plurality of offers to be output to a consumer via a mobile device 120 (FIG. 1). In accordance with one embodiment, the offer assembly module 230 or another component of system 200 may be operable to output one or more offers to a consumer (and, in some instances, receive input from a consumer, such as a request for a plurality of offers for filling a prescription, an acceptance of an offer and/or information regarding pharmacy benefit plan of the consumer) via an APBM user interface 215. The description herein of process 300 (described with respect to FIG. 3) provides some examples of how the modules 222-232 may be operable to utilize the data stored in database 202 to facilitate fulfillment of a prescription.

The APBM interface 215 may, for example, take the form of a Web server that conveys data in HTML, XML, or other well-known formats using well-known transmission protocols, such as HTTP and TCP/IP. Proprietary protocols and data formats may also be used. A mobile device 120, which may take the form of a desktop computer, laptop computer, personal digital assistant (PDA), mobile phone, smart phone, or other computing device, may be used by a consumer or consumer to obtain information relating to fulfillment of pharmaceutical prescriptions and such information may be presented to the consumer or consumer via the APBM interface 215. FIGS. 4A-4H illustrate non-limiting examples of the type of information that may be output to, and mechanisms which may be collected from, a consumer via an APBM interface such as APBM interface 215.

Figure 3A:
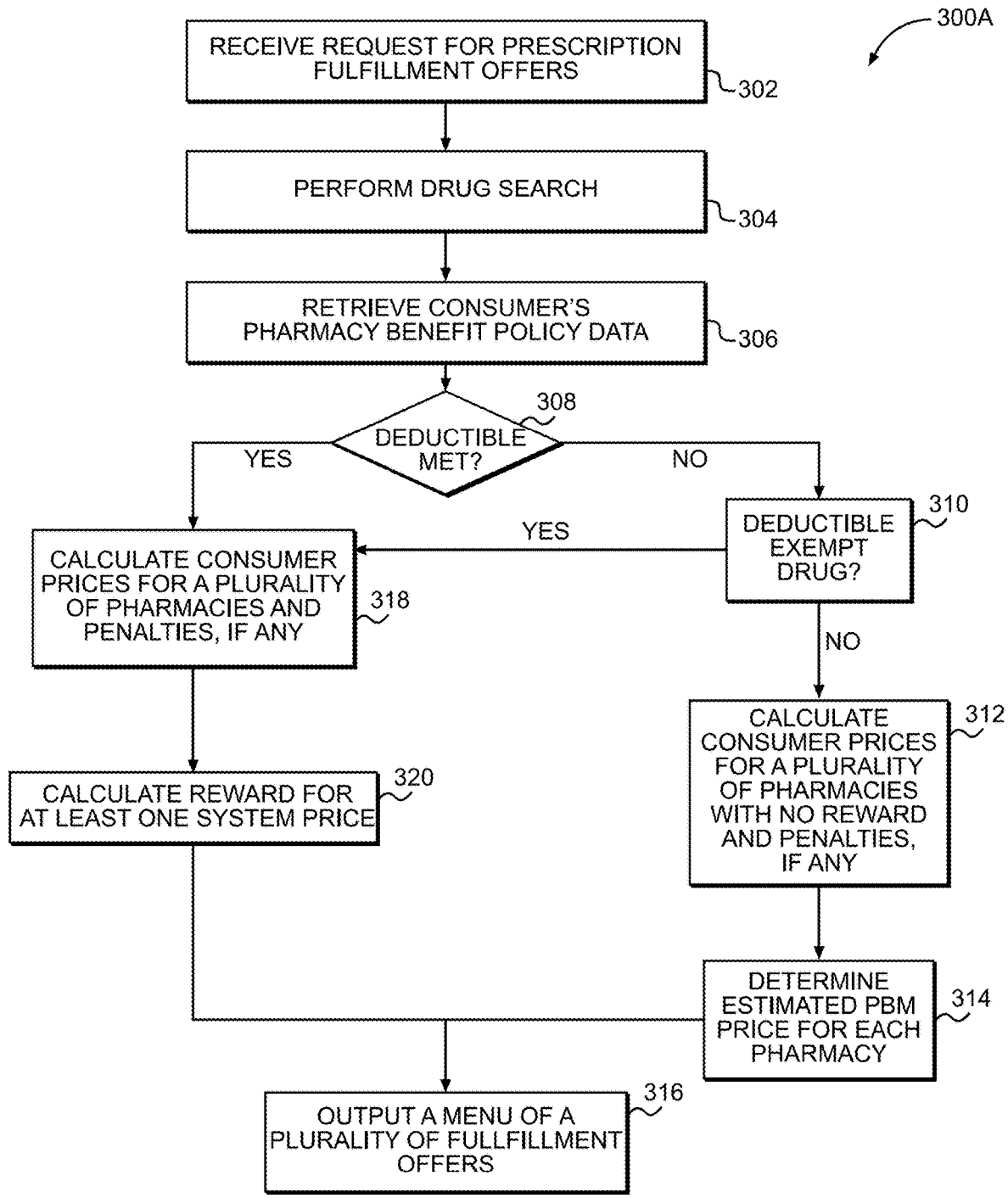
FIG. 3A is a flow diagram of an example offer assembly process consistent with at least some embodiments described herein.

Turning now to FIG. 3A, illustrated therein is an example process 300A which provides one embodiment of how a plurality of offers for fulfilling a pharmaceutical prescription outside of the traditional PBM structure may be output to a consumer. Process 300A may, for example, be performed by APBM system 200 (FIG. 2). In some embodiments, the process 300A may be performed and/or implemented by and/or otherwise associated with one or more specialized and/or specially-programmed computers (e.g., the processor 201 of FIG. 2). It should be noted, with respect to process 300A and all other processes described herein, that not all steps described with respect to the process are necessary in all embodiments, that the steps may be performed in a different order in some embodiments and that additional or substitute steps may be utilized in some embodiments.

Figure 4A:
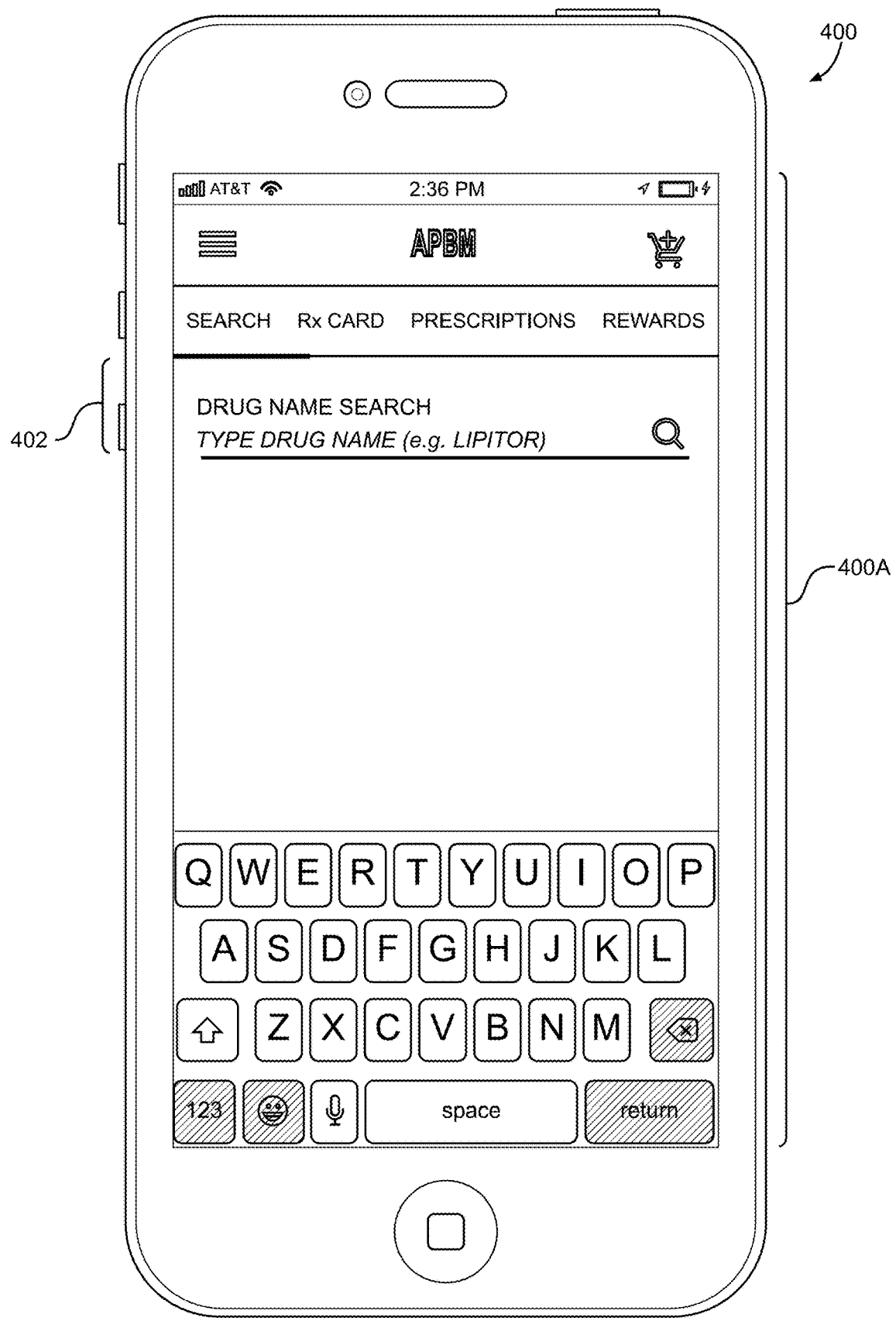
FIGS. 4A through 4H are example graphical user interfaces that may be output to a consumer in accordance with some embodiments described herein.
Figure 4B:
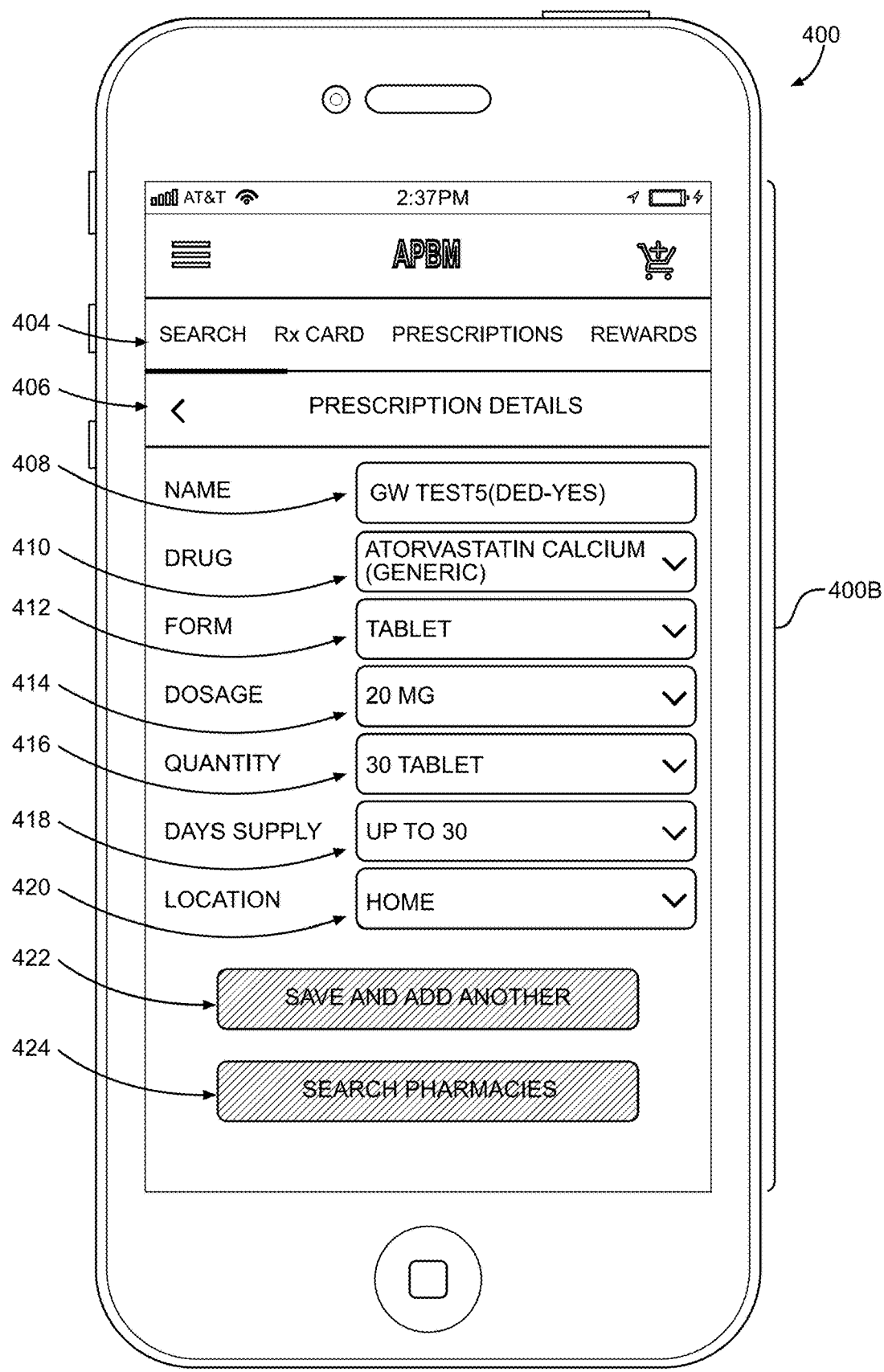
Figure 4C:
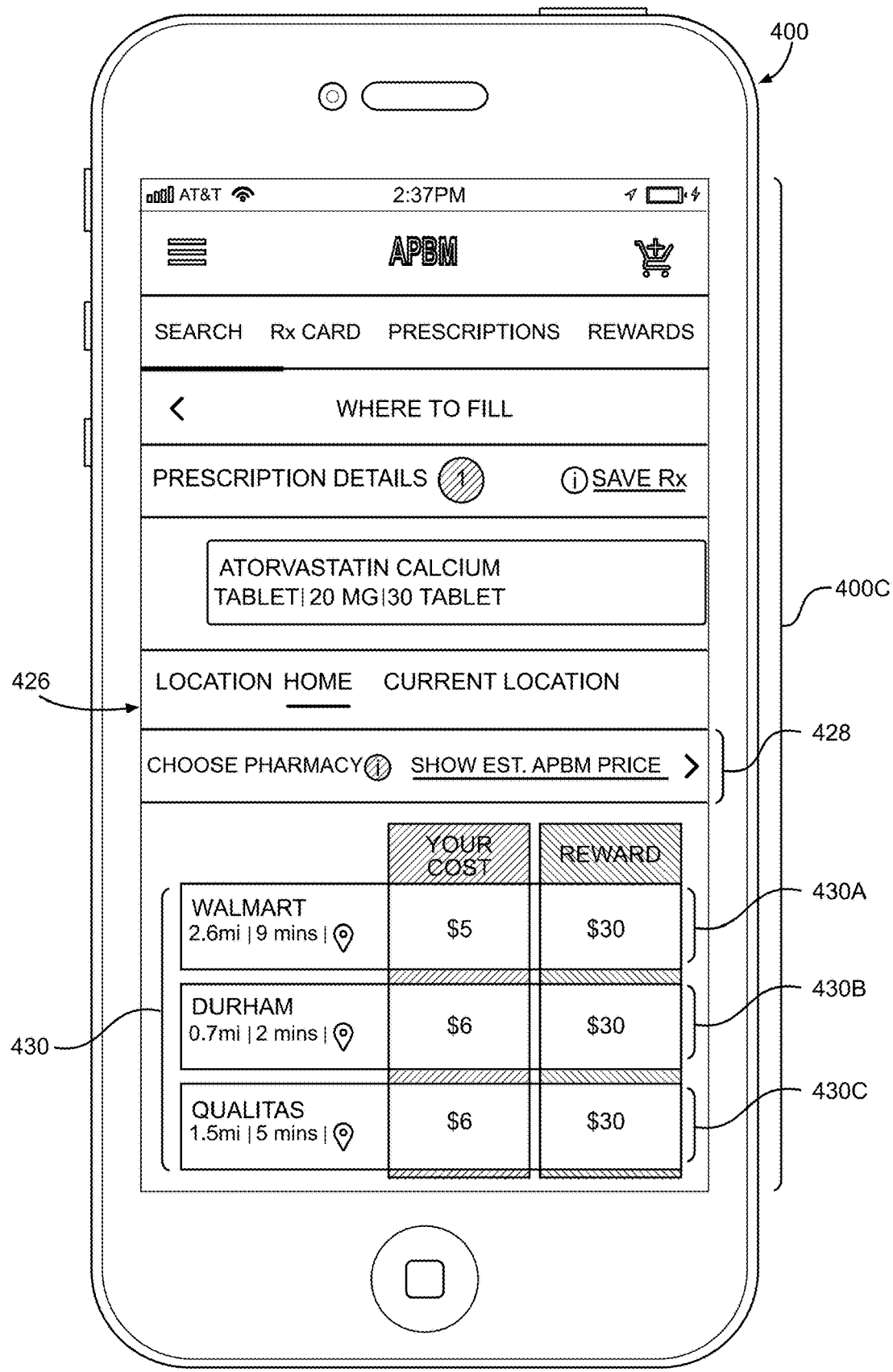
Figure 4D:
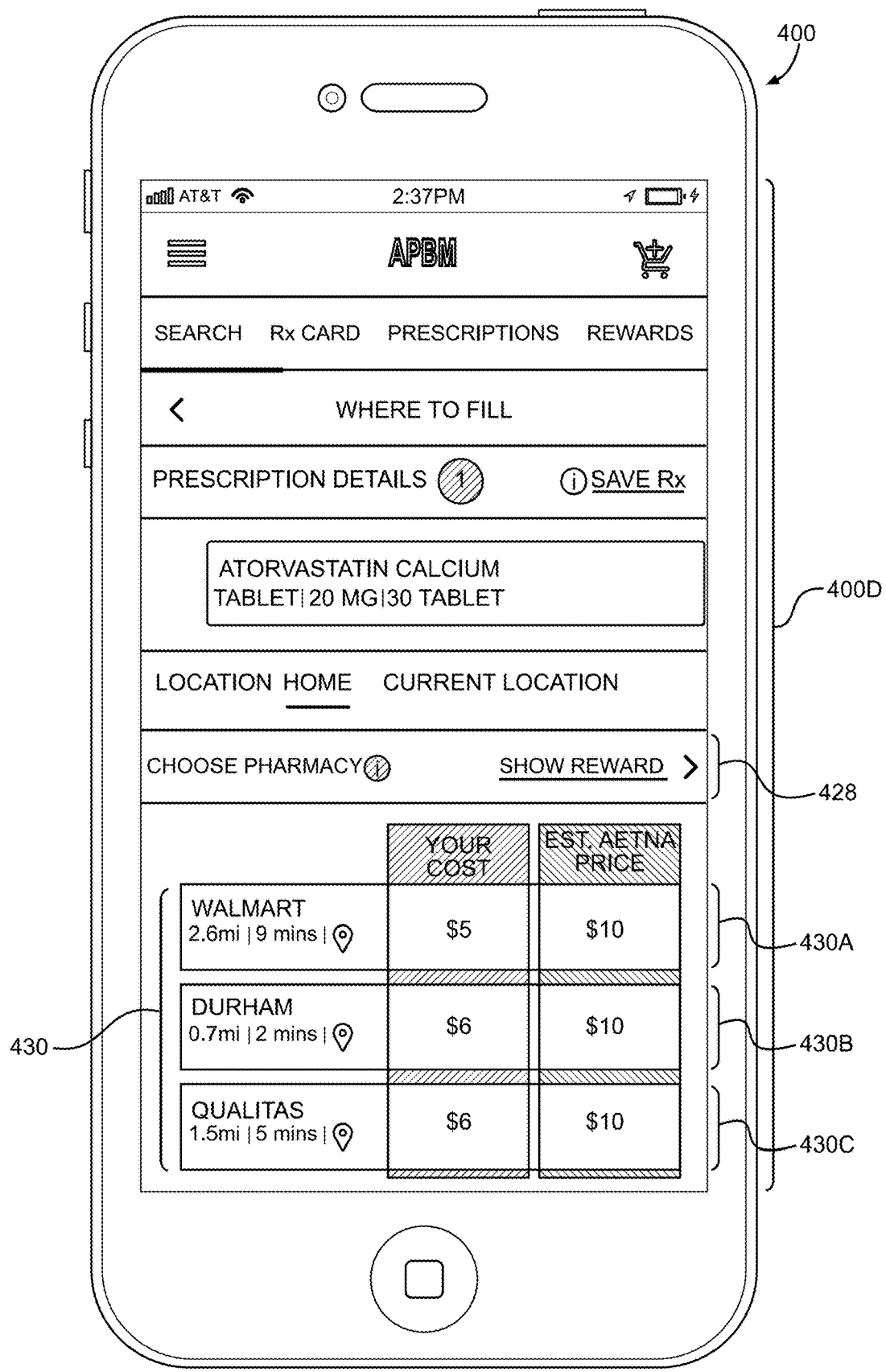
Figure 4E:
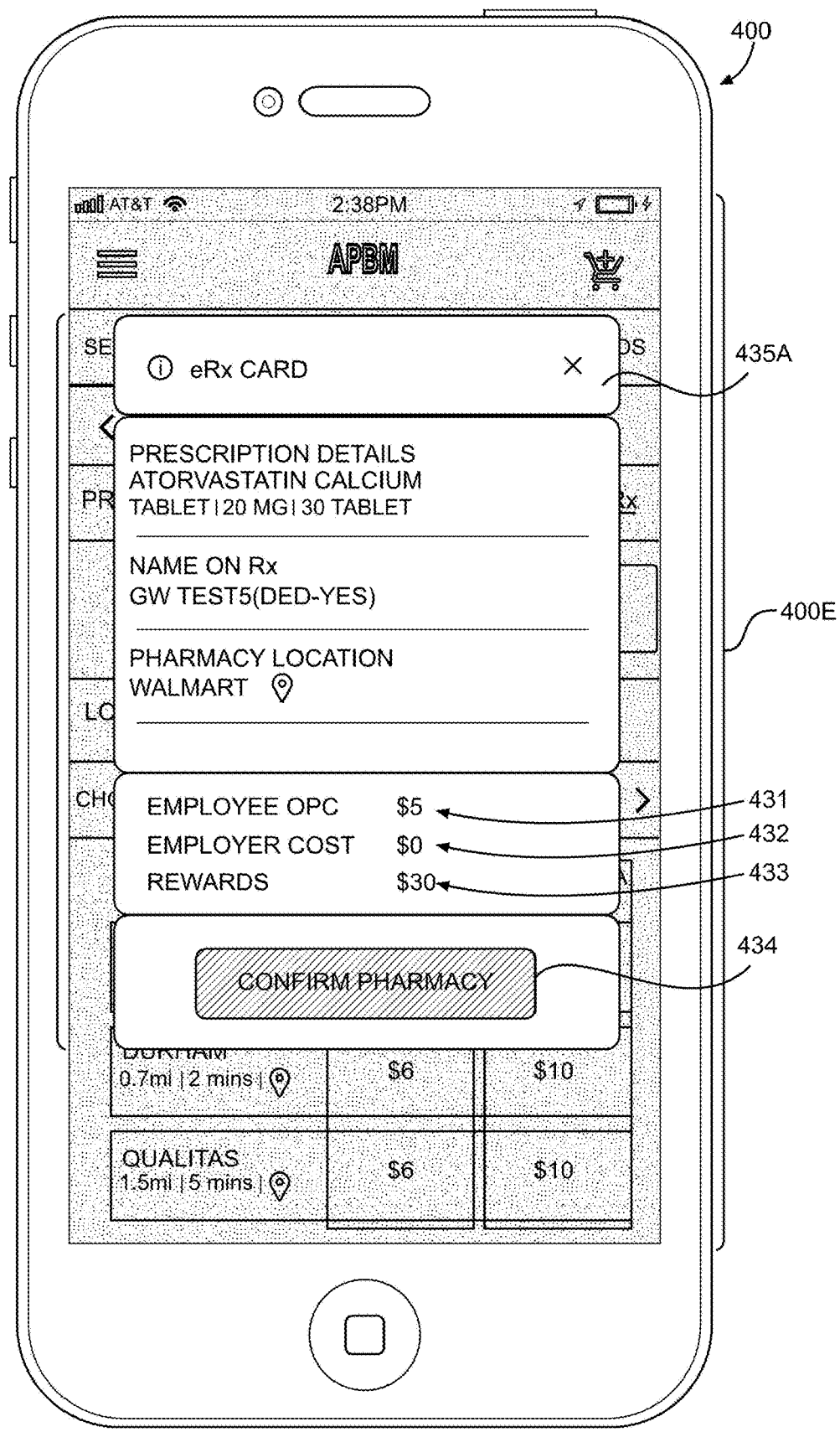
Figure 4F:
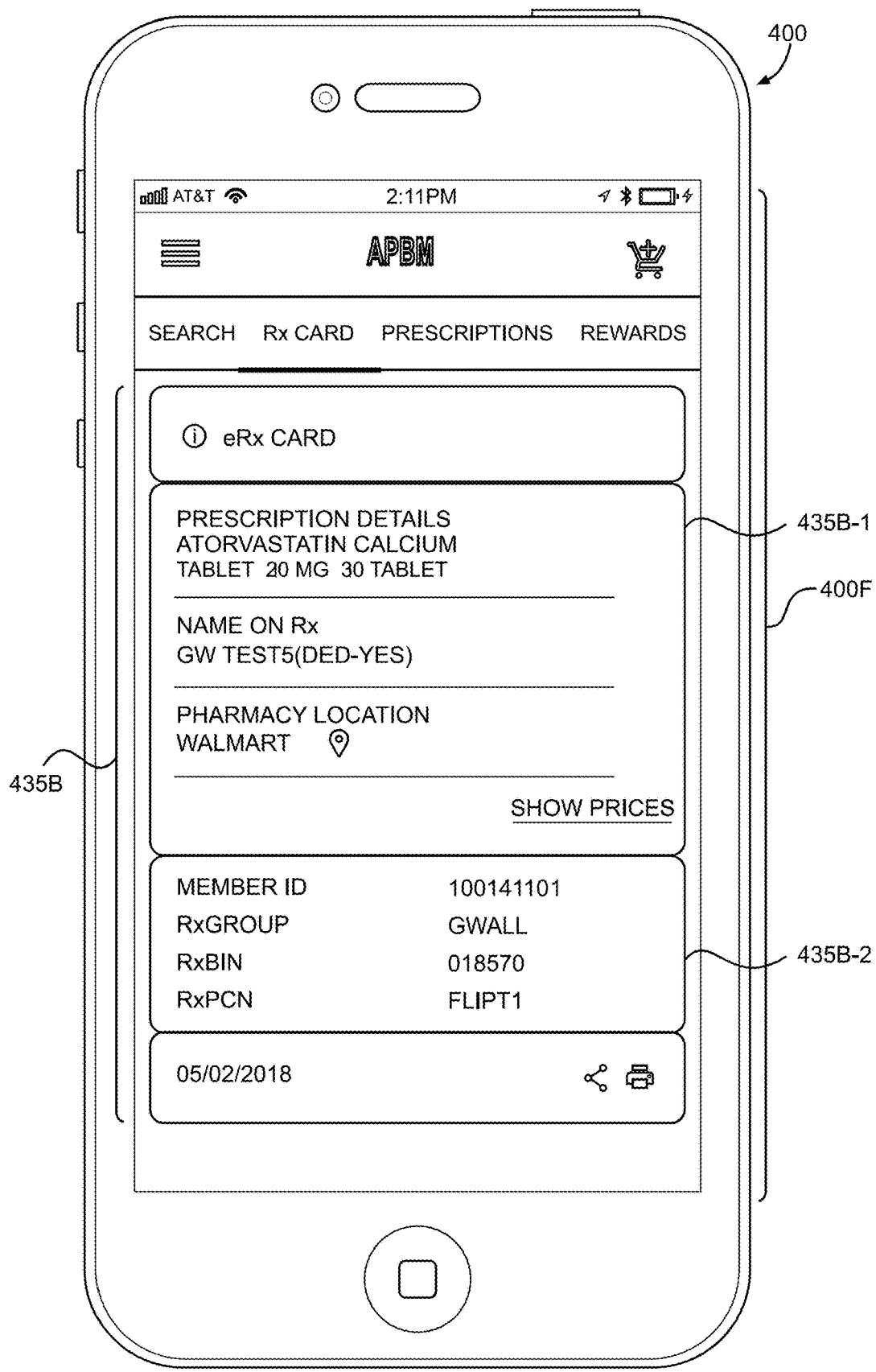
Figure 4G:
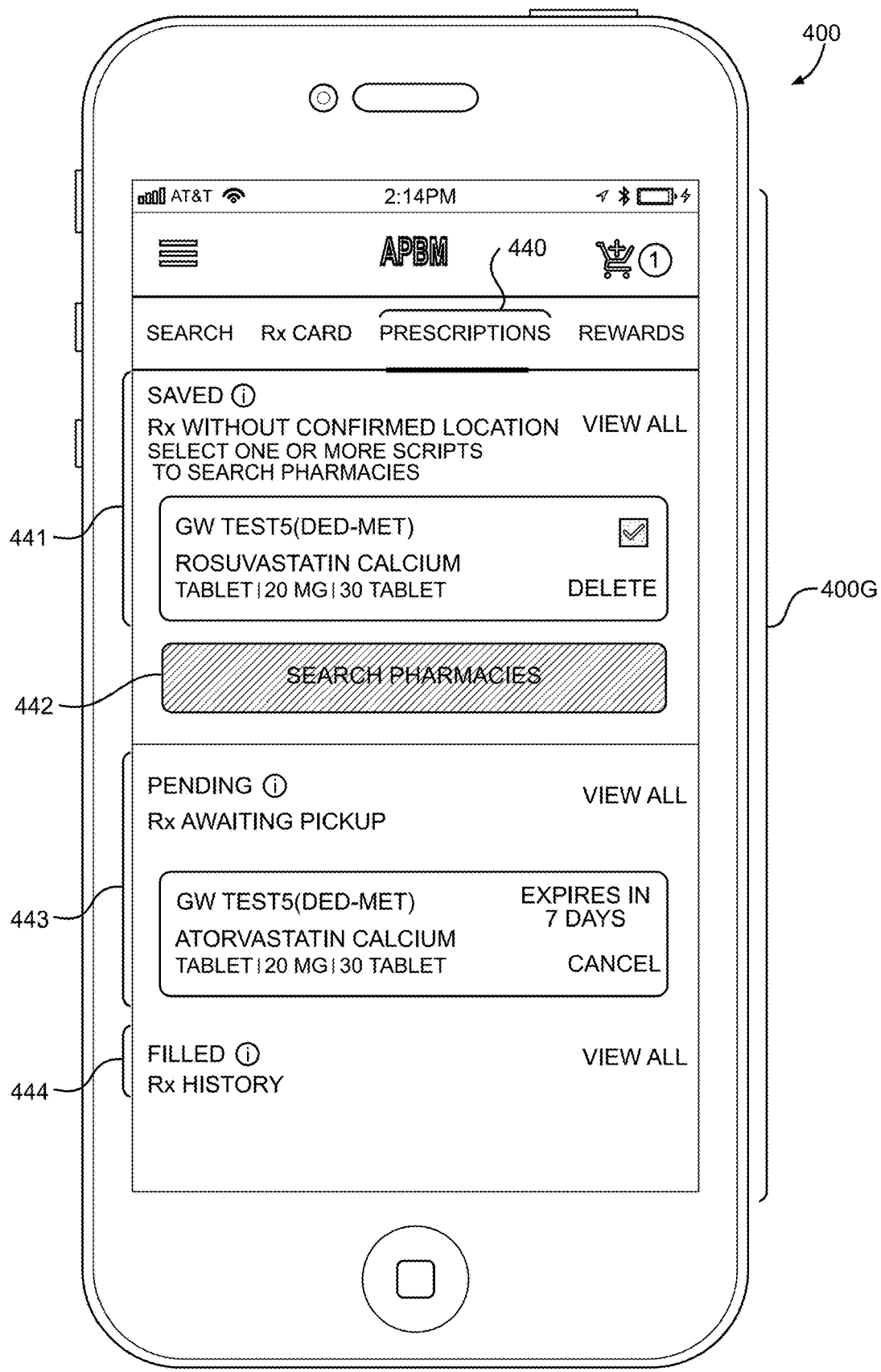
Figure 4H:
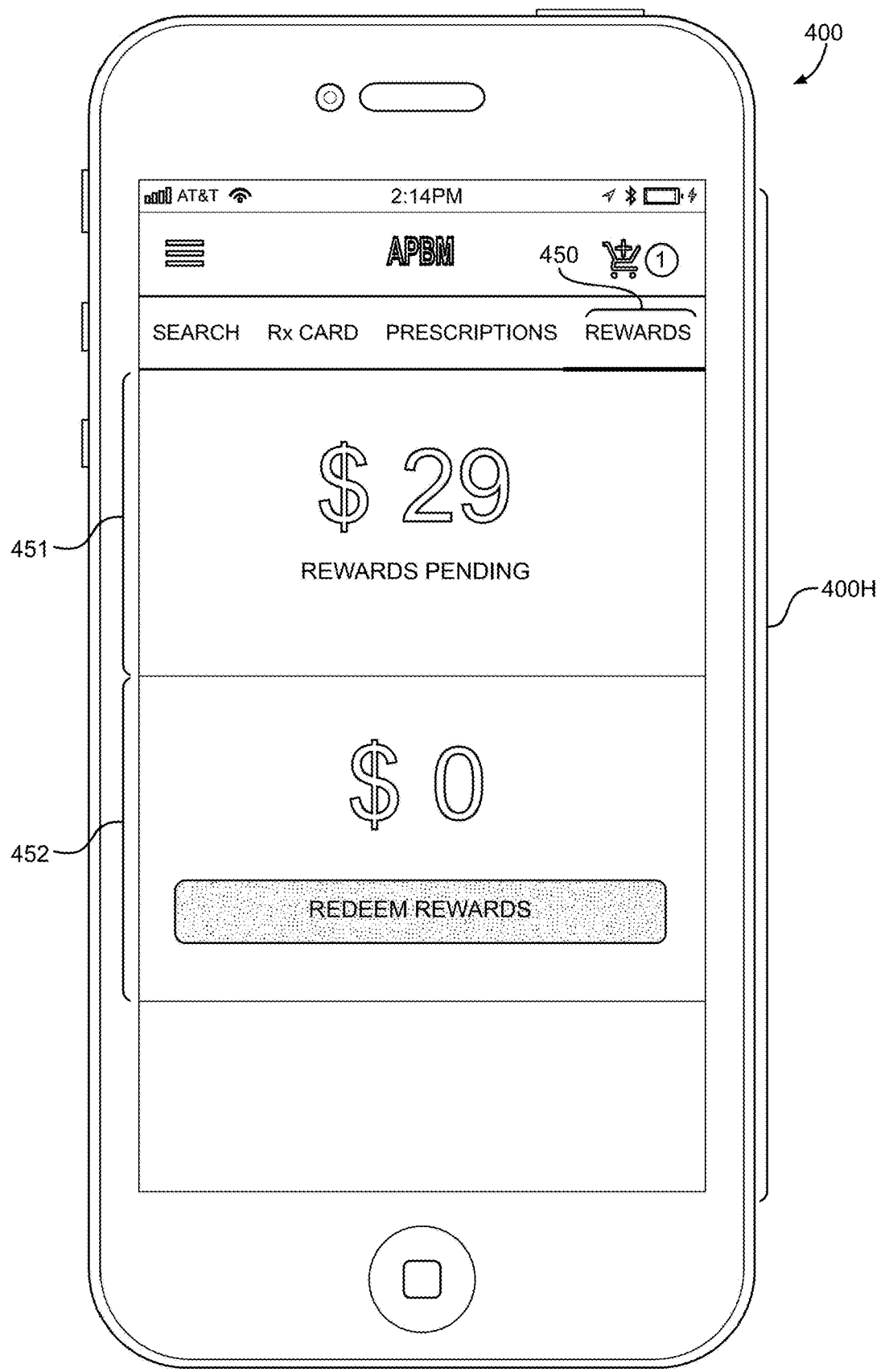

Process 300A will be described herein with reference to FIGS. 4A-4F, which illustrate a series of graphical user interfaces which may be presented to a consumer during a progression of the consumer's request for a plurality of offers for pharmacy locations at which a prescription may be filled, as well as examples of user interfaces that the consumer may access via an APBM app in order to track and manage his prescriptions and rewards. FIGS. 4A-4H each illustrate a respective graphical user interface (GUI) as it may be output on a mobile device 400 (which may comprise an example of a mobile device 120, FIG. 1, or mobile device 501, FIG. 5). The GUI 400 may comprise several tabs or screens, as illustrated in each of FIGS. 4A-4H. Thus, FIG. 4A illustrates a screen 400A that may be output as part of an APBM GUI, FIG. 4B illustrates a screen 400B that may be output as part of an APBM GUI, FIG. 4C illustrates a screen 400C that may be output as part of an APBM GUI, FIG. 4D illustrates a screen 400D that may be output as part of an APBM GUI, FIG. 4E illustrates a screen 400E that may be output as part of an APBM GUI, FIG. 4F illustrates a screen 400F that may be output as part of an APBM GUI, FIG. 4G illustrates a screen 400G that may be output as part of an APBM GUI and FIG. 4H illustrates a screen 400H that may be output as part of an APBM GUI.

In accordance with some embodiments, the APBM GUI may be made available via a software application operable to receive and output information regarding pharmaceutical prescription fulfillment offers as generated and managed by an APBM in accordance with embodiments described herein. It should be noted that many variations on such graphical user interfaces may be implemented (e.g., menus and arrangements of elements may be modified, additional graphics and functionality may be added). The graphical user interfaces of FIGS. 4A-4H are presented in simplified form in order to focus on particular embodiments being described.

The FIGS. 4A-4F illustrate successive screens that may be output to a consumer from the time a consumer enters a name of a prescription drug and requests at least one offer for fulfilling the prescription, as the one or more offers are output to the consumer, the consumer confirms an accepted offer and an indication from the APBM is output to the consumer for the confirmed accepted offer. FIGS. 4G and 4H each respectively illustrate a screen that may be output to a consumer upon demand, as the consumer desires to view certain information regarding prescriptions or rewards he/she has with the APBM system.

Turning now to FIG. 3A, process 300A is initiated at block 302 upon it being determined that a request for prescription fulfillment offers has been received from a consumer (e.g., via an APBM interface, such as APBM interface 215 or such as illustrated in GUI 400A of FIG. 4A).

In accordance with some embodiments, a consumer may enter prescription information for a new prescription while at a medical provider's office, such that the medical provider (e.g., doctor) can help the consumer provide the appropriate information when submitting the request (e.g., the drug name, dosage and quantity). For example, the consumer (who has pre-registered with the ABPM system) may log in to his account with the APBM using a software application pre-loaded onto his mobile device and select an option to enter a new prescription (e.g., as illustrated in the search bar 402 of FIG. 4A). In one embodiment, the consumer may enter the brand name of a prescription drug in order to initiate the process, while in other embodiments the consumer may provide a generic name or even a name that is descriptive of a class of drugs or a medical condition that the desired drug is approved to treat. The consumer may also be prompted to provide additional information for the prescription, such as the dosage, form (e.g., liquid or tablet) and quantity of the drug as being prescribed by the medical provider. In some embodiments, the process 300A or a similar process may be initiated while the consumer is at a pharmacy of his/her choice, attempting to fill a prescription.

The APBM system then launches a drug search in block 304, based on the information received from the consumer in block 302 (e.g., based on the information provided in GUI 400A and/or GIU 400B). In accordance with some embodiments, the search for an acceptable pharmaceutical drug based on the information received from the consumer in step 302 may be performed by the drug selection module 222 of FIG. 2 and utilizing the data stored in database 202, such as the drug data 216, the formulary data 218 or other prescription drug data). In accordance with some embodiments, the APBM maintains a database of pharmaceutical drugs such that it can search for and retrieve acceptable substitutes for a drug name as entered by the consumer. For example, if the consumer has entered a brand name for a pharmaceutical drug, the APBM may be operable to look up any and all generic versions of the drug. In accordance with one embodiment, the system may utilize the Generic Product Identifier (GPI) classification system to identify acceptable generic equivalents. In one embodiment, the system may store a ranking of generic equivalents and alternatives for a brand drug and may be programmed to select the highest ranked generic equivalent or alternative. In one embodiment, a ranking of equivalents may be based on the Pharmacy Reimbursement Price corresponding to each equivalent (e.g., the lowest priced equivalent being ranked the highest).

In some embodiments, the APBM may facilitate a proprietary crowd-sourcing or peer-review process via which medical professionals are polled to provide their professional opinions as to which prescription drugs are acceptable substitutes for one another. In the event that the consumer searched for a drug and at least one equivalent or alternative generic version was found, or cheaper alternative brand version was found, the system may suggest the alternative version to the consumer and/or the medical professional prescribing the drug and, if the consumer agrees to view offers for the alternative version, the system may proceed with process 300A using the alternative version (in accordance with some embodiments, the consumer may be provided with a mechanism to switch back to the brand drug if desired, in which case some of the following steps of process 300A may be repeated for the brand drug). If the consumer had entered a generic prescription drug name to initiate the search, the APBM system may look up the generic drug in its drug database (e.g., in drug data 216 of memory 202) to either find the closest match and present it to the consumer or to find with the highest ranked product equivalent.

In accordance with some embodiments, the APBM system may request that the consumer confirm details of the prescription for which fulfillment offers are being requested and/or verify the drug information (e.g., dosage, quantity or days of supply needed) prior to continuing to step 306. In some embodiments, confirming the details of the prescription may also include confirming the name of the patient named on the prescription for which fulfillment offers are being requested (e.g., the prescription may be for a child, spouse or other family member of the consumer who is submitting the request for the offers). Turning briefly to FIG. 4B, illustrated therein is an example screen 400B that may be output to a consumer, via which the consumer is requested to confirm information regarding the prescription for which fulfillment offers will be assembled. In the example screen 400, area 406 indicates to the consumer that the consumer is viewing details of the prescription (and allows the consumer to go back to a previous screen, such as screen 400A, by selecting the arrow in the left side of this area). Area 404 indicates a plurality of different types of information that the consumer can view using the software app. Area 408 indicates the name of the consumer who has logged in to the app and is requesting the prescription offers. In some embodiments, this area or another area may indicate the name of the patient named on the prescription, which may differ from the consumer who is requesting the offers (e.g., the patient may be a child or spouse of the consumer) and/or allow the consumer to indicate a name of a patient other than the consumer. Area 410 indicates the name of the prescription drug for which the prescription offers will be assembled. For example, area 410 may indicate the name of the drug as entered by the consumer in area 402 of screen 400A or the name of an alternate generic version of that drug that the system is recommending. In accordance with some embodiments, area 410 may comprise a drop-down menu via which the consumer may select alternate versions of the drug or other acceptable substitute drugs (e.g., as identified in step 304, which may in some embodiments comprise populating this drop-down menu). Area 412 indicates the form of the drug (e.g., tablet vs. liquid) that is going to be used to assemble the offers and allows the consumer (e.g., via a drop-down menu) to select an alternate form. Area 414 indicates the dosage of the drug that is going to be used to assemble the offers and allows the consumer (e.g., via a drop-down menu) to select an alternate form. Area 416 indicates the quantity of the drug that is going to be used to assemble the offers and allows the consumer (e.g., via a drop-down menu) to select an alternate form. Area 418 indicates the number of days of supply of the drug that is going to be used to assemble the offers and allows the consumer (e.g., via a drop-down menu) to select an alternate form. Area 420 indicates the search location that is going to be used to search for pharmacies at which the prescription may be fulfilled (the search location and process of searching for pharmacies is described in detail with respect to process 300B of FIG. 3B). In accordance with some embodiments, the content of any of the drop-down menus illustrated in areas 410-418 may be populated by the system, such as in step 304 based on the results of step 304. In some embodiments, data entry formats other than drop-down menus may be used in any of the fields 410-420 (e.g., the consumer may be allowed to enter data free-form or select options via radio buttons or pop-up windows). Once the consumer is satisfied with the prescription details shown, he/she can select area 424 to launch the offer assembly process (or to allow the offer assembly process to continue). Alternately, the consumer may select area 422 to save the details of the present prescription and continue to add information for another prescription, in which case the consumer may be taken to another screen or returned to screen 400A.

Returning now to FIG. 3, as described herein, a consumer who would like to see offers for prescription drug fulfillment options from the APBM system may download its software app onto his/her mobile device and register with the APBM system. In registering with the APBM system, the consumer may, in at least some embodiments, be asked to provide information on his/her pharmacy benefit plan or plan (or this information may be provided by the consumer's PBPP or employer). Such information may include, for example, the PBPP of the plan, a group number, a member identification number, a type or classification of the plan and the names of all persons covered under the plan (e.g., any family members of the consumer who are covered under the plan, their birthdates, etc.). The APBM system may be operable to verify the consumer's coverage under this plan (e.g., by contacting the PBPP directly). In some embodiments the APBM system may further be operable to obtain from the PBPP additional information regarding the consumer's benefits under the plan for use in assembling offers (e.g., the deductible amount, period and associated restrictions or conditions; the coverage period under the plan; the formulary to be utilized for the plan). Such information defining the consumer's pharmacy benefit pharmacy may be stored by the APBM (e.g., in the patient data 210 of database 202) and subsequently retrieved when the consumer inputs a request to receive fulfillment offers for a new prescription.

In accordance with some embodiments, the APBM may have relationships with certain PBPPs and only consumers who have plans from these PBPPs may be able to register with the APBM. In some embodiments, the APBM may receive (e.g., periodically) and store updated information regarding a consumer's pharmacy benefit plan (e.g., from the PBPP corresponding to the consumer's plan or another party), such as whether the consumer is still within the deductible period and/or how much is left in the consumer's deductible amount. In other embodiments, consumers may be able to register with the APBM system even if their PBPP does not have a relationship with the APBM. In some embodiments, consumers who do not have a pharmacy benefit plan or who do not desire to provide information regarding their pharmacy benefit plan to the APBM for purposes of having the APBM assemble prescription fulfillment offers may also be able to register with the APBM.

In block 306, the pharmacy benefit plan information corresponding to the consumer for whom offers are currently being assembled is retrieved. For example, a record for the consumer may be stored in a database of the APBM and accessed based on the login credentials the consumer entered when launching the software application or otherwise initiating a request for the offers.

The APBM system may retrieve information associated with the consumer's pharmacy benefit plan that will be used to assemble one or more prescription fulfillment offers. One example of information related to the consumer's pharmacy benefit plan that may be retrieved is an identification of the PBM associated with the PBPP that provides the plan to the consumer such that the appropriate formulary corresponding to the PBM may be retrieved from a database (e.g., from the formulary data 218 of memory 202, FIG. 2). In one embodiment, the PBM identification may be determined based on information stored in consumer data 210 of memory 202 while in other embodiments the PBM may be identified based on information stored in PBPP data 212 of memory 202. Other examples of information related to the consumer's pharmacy benefit plan that may be retrieved and utilized in assembling one or more prescription fulfillment offers include, without limitation, (i) an indication of whether the consumer is still within the deductible period of the plan; (ii) persons covered under the consumer's plan; (iii) an indication of any co-insurance or co-pay amounts the consumer is responsible for paying and corresponding rules or conditions that govern the application of such co-insurance or co-pay; (iv) other prescriptions prescribed to the same patient of the present prescription; (v) health-related information such as weight, age and medical treatment history; (vi) income from the company sponsoring the plan; (vii) zip code; (viii) length of employment with the company sponsoring the plan; and/or (ix) position within the company sponsoring the plan.

Block 308 is a decision block as to whether to proceed to block 310 or block 318, based on whether the consumer is currently within his/her deductible period (if any) or has met their maximum annual out of pocket (if any) the pharmacy benefit plan retrieved in block 306. In accordance with some embodiments, the calculation of a Consumer Price (the monetary value the consumer will pay out-of-pocket for the prescription drug of the present prescription) is calculated differently depending on whether the consumer is still under a deductible period (in which case the consumer will be expected, under most circumstances, to pay for the prescription drug without the PBPP paying for any portion of it) or whether the consumer is no longer under a deductible period (in which case, under most circumstances, the consumer will be responsible for paying the co-pay and a co-insurance amount (if any) as defined by his/her pharmacy benefit plan and the PBPP will be responsible for paying the remainder).

If it is determined in step 308 that the deductible amount for the consumer's pharmacy benefit plan has not yet been met (i.e., the answer to step 308 is "no"), the process 300A proceeds to block 310; otherwise the process 300A proceeds to block 318. In block 310 it is determined whether the prescription drug for which prescription fulfillment offers are currently being assembled is one that is exempt from the plan's deductible amount. Some pharmacy benefit plans define a list of drugs (e.g., preventative maintenance drugs like cholesterol and blood pressure medications) that are "deductible exempt" meaning that the consumer only has to pay the co-pay amount for these drugs even during the deductible period and the PBPP is responsible for the remaining cost. The system may access information associated with the consumer and/or the consumer's pharmacy benefit plan (e.g., consumer data 210, PBPP data 212 and/or formulary data 218 of memory 202, FIG. 2) to determine whether the drug is a deductible exempt drug under the consumer's pharmacy benefit plan. If it is determined that the drug is a deductible exempt drug, the process 300A continues to block 318; otherwise the process continues to block 312.

In some embodiments, a consumer who does not have (or has not provided to the APBM an indication of having) a pharmacy benefit plan may be registered with the APBM and be requesting prescription fulfillment offers. In such an embodiment, the process 300A may include a step that determines whether this is the case and performs a different subroutine or process as a result. Alternatively, such a consumer's offers may be assembled in accordance with process 300A but the system may be programmed to handle such a consumer in a specific manner at different blocks of process 300A (e.g., omit step 304 and determine the answers to each of step 306 and step 308 is "no").

Figure 3B:
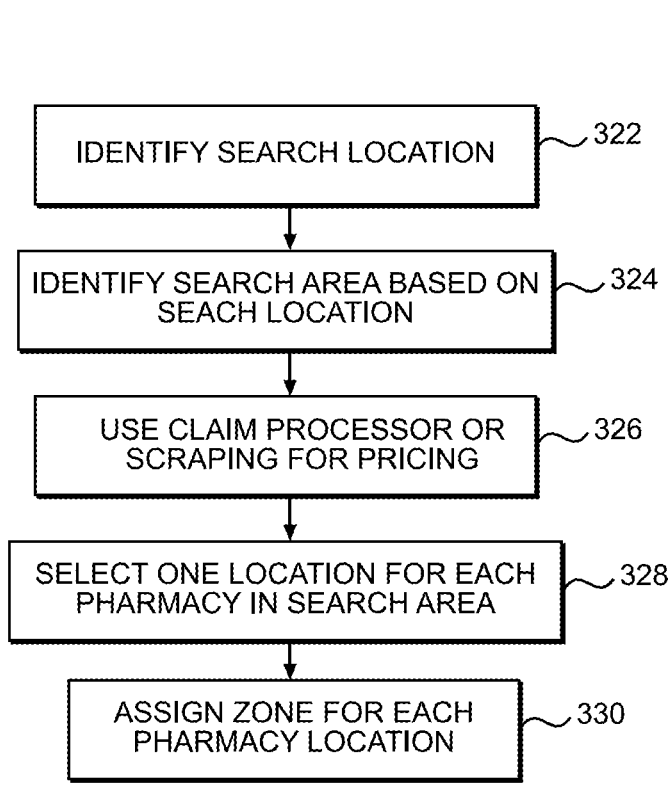
FIG. 3B is a flow diagram of an example pharmacy selection sub-routine that is consistent with at least some embodiments described herein.

In block 312 consumer prices are calculated for a plurality of pharmacies at which the consumer may redeem the prescription, in a scenario in which the consumer has not yet satisfied his/her deductible and the prescription is for a drug that is not a deductible drug (or in a scenario in which the consumer does not have a pharmacy benefit plan and is relying on the APBM system as his primary prescription fulfillment mechanism). In this scenario, the consumer is responsible for the entire cost of the drug (i.e., the cost is not shared with a PBPP). As a preliminary sub-routine for determining the consumer price for each of a plurality of pharmacy locations may comprise a process for selecting the plurality of pharmacy locations, one for each offer being assembled. FIG. 3B illustrates one example process 300B for selecting a plurality of pharmacy locations to be included in offers being assembled for a prescription and will now be described.

Turning now to FIG. 3B, illustrated therein is an example process 300B which provides one embodiment of how a plurality of specific pharmacy locations, one for each of a plurality of offers that are being assembled for a prescription, may be selected. Process 300B may, for example, be performed by APBM system 200 (FIG. 2). In some embodiments, the process 300B may be performed and/or implemented by and/or otherwise associated with one or more specialized and/or specially-programmed computers (e.g., the processor 201 of FIG. 2). In one embodiment, the process 300B may be performed by a sub-routine of APBM 200, such as the pharmacy selection module 226 (FIG. 2).

As a preliminary matter, a search location for the prescription is identified at block 322. The search location may, in accordance with some embodiments, comprise a starting location for the search based on a location associated with the consumer who has requested the prescription fulfillment offers. For example, the search location may comprise one of: (i) a current location of the consumer's mobile device; (ii) a home address of the consumer; or (iii) a stored addressed that the consumer has provided as a preferred address to be used as a search location (e.g., the consumer's work address). In some embodiments, the consumer may enter or select (and update as desired) a default location to be used as a search location for his prescriptions and have this stored in association with his/her data by the APBM system (e.g., as part of the consumer data 210 in memory 202). In some embodiments, as illustrated in area 426 of the screen 400C illustrated in FIG. 4C, the GUI may output to the user a mechanism for toggling back-and-forth between two or more search location choices (in the example of FIG. 4C, this being a choice between the consumer's stored home address and a current location of the consumer's mobile device). In accordance with some embodiments, identifying the search location may comprise identifying the geocodes for, or geocoding, the search location. Geocoding is the computational process of transforming a postal address description to a location on the Earth's surface (spatial representation in numerical coordinates).

Once the search location is identified in block 322, a search area is determined in block 324. A search area is the geographical area around the search location within which potential pharmacy locations are to be searched. Although any scope and shape of a search area may be utilized and the embodiments described herein are not dependent on any particular search area scope or shape, in accordance with one embodiment the search area is identified by creating a box by adding ten (10) miles to the search location longitude and latitude in each direction.

In block 326, pricing information that may be useful for narrowing down the pharmacies within the search area that may be selected for inclusion in a plurality of prescription offers may be determined, in accordance with some embodiments (in other embodiments, step 326 may be omitted or different or additional filters may be applied to narrow down a list of possible pharmacies). For example, information from one or more of the following sources may be utilized to generate a list of potential pharmacies within the search area: (i) a claim processor; (ii) publicly available information from the world wide web (e.g., www.cms.gov); and (iii) a proprietary database such as the pharmacy data 214 of memory 202). Such information may be obtained by scraping it from one or more of the available sources or having it provided by the one or more sources to the APBM system. In some embodiments, additional information corresponding to the pharmacies (e.g., MAC prices corresponding to different pharmacies) may further be utilized to generate a list of potential pharmacies to include in the offers (e.g., the pharmacies with the lowest MAC list prices for the prescription drug may be selected).

It should be understood that for prescription drugs for which multiple different generic versions are available, different pharmacies may stock different ones of these generic versions. The APBM may identify or infer which particular generic version a particular pharmacy stocks in its inventory based on claims data that it may receive from a claims processor. In other embodiments in which the APBM has direct relationships with pharmacies, the APBM may receive an indication directly from the pharmacy as to which generic version of a particular drug it stocks. In one embodiment, the APBM may store an indication of which generic drug a particular pharmacy stocks and retrieve this data for use in either selecting pharmacies within the search area (e.g., if the APBM is searching for pharmacies that stock a particular generic drug), such as in pharmacy data 214 of memory 202, FIG. 2).

In many cases, multiple locations for a given pharmacy may be identified within the search area. Accordingly, in block 328, if multiple pharmacy locations (i.e., pharmacy retail stores) are identified for a given pharmacy, the system selects a subset of these (e.g., one) to include in the plurality of offers that are being assembled for the current prescription. For example, in accordance with one embodiment the pharmacy location that is closest to the search location (e.g., based on linear distance) may be selected for each pharmacy.

In accordance with some embodiments, the offers that are assembled and output to a consumer are generated and organized such that in the plurality of offers there is at least one offer that includes a pharmacy location in each of a plurality of zones (e.g., distance zones) relative to the search location. In accordance with some embodiments, three (3) zones may be utilized, as follows: (i) a first zone (which may, in accordance with some embodiments, be referred to as a "comfort zone") which is defined by the shortest relative distance to the search location; (ii) a second zone (which may, in accordance with some embodiments, be referred to as an "economy zone" and is farther from the search location; and (iii) a third zone (which may, in accordance with some embodiments, be referred to as a "savers zone") and be the furthest from the search location.

In accordance with some embodiments, an economy zone may be defined as being wide enough to capture the three (3) closest pharmacies of the search location, an economy zone may be defined as the next five (5) closest pharmacies of the search location and a savers zone may be defined as being all other pharmacies of the search location. In other embodiments, such zones may be defined via other parameters (e.g., distance from the search location, such that the first zone is within X miles of the search location, the second zone is located between X and Y miles of the search location and the third zone is located between Y and Z miles of the search location, where Z>Y>X).

While such zones may be utilized internally by the system to generate offers for a consumer, the indication of which offer corresponds to which zone may not be explicitly indicated to the consumer (e.g., the distance of a particular pharmacy location may be indicated in an offer, but not that it is in a "economy zone" as such).

A zone categorization of a particular pharmacy location may be utilized by the system to define other parameters of an offer in which the pharmacy location is included. For example, in one embodiment the zone categorization of the pharmacy location may be utilized to determine a reward amount to be included in the offer that defines that pharmacy location (e.g., by determining what percentage or portion of the difference between the PBM Price and the Pharmacy Reimbursement Amount corresponding to that offer should be included as a reward defined by the offer). In accordance with some embodiments, the APBM system may encourage a consumer to fill a prescription at a pharmacy location that maximizes savings for the consumer and/or the consumer's PBPP by presenting the consumer with an offer that defines a pharmacy with a relatively low Patient Price (based on a relatively low Pharmacy Reimbursement Amount) even though the pharmacy location is not located at a convenient distance from the consumer's location.

In accordance with some embodiments, if a pharmacy location that is within the search area for a prescription has a very low Consumer Price (or has a relatively large differential between the PBM Price and the Pharmacy Reimbursement Price) but is within relatively further distance from the search location (e.g., within the economy zone or within the savers zone), the offer may include a relatively larger reward amount in order to encourage the consumer to accept the offer and fill the prescription at an inconvenient location but one that results in relatively higher savings (vis-à-vis a PBM Price) to the consumer and/or the consumer's PBPP. In another embodiment, a use of the zone categorization may be to allow the system to ensure that the plurality of offers that is ultimately output to the consumer includes at least one pharmacy location from each zone.

It should be understood that the number of zones (and the distance from the search location that each zone is defined by) may differ based on preference of the APBM and/or the PBPP and the embodiments described herein are not dependent on any particular number of zones or any particular distances or other parameters that defines each zone. Once a list of pharmacy locations is determined via sub-routine 300B (and, in some embodiments, a zone categorization is assigned to each such location), the offer assembly process may return to process 300A.

Returning once again to process 300A (FIG. 3A) and block 318 thereof, once a list of pharmacy locations is determined (e.g., via a sub-routine such as sub-routine 300B of FIG. 3B), the system continues to further assemble the plurality of prescription fulfillment offers by determining a Consumer Price for each pharmacy location. In accordance with some embodiments, determining the consumer price may also comprise determining a penalty or reward (if any) to be included in a particular offer. An example process 300C will now be described, with reference to FIG. 3C, to illustrate one method for how a Consumer Price may be calculated for a particular offer (including a determination of whether the offer should include a penalty or a reward, as described below).

Figure 3C:
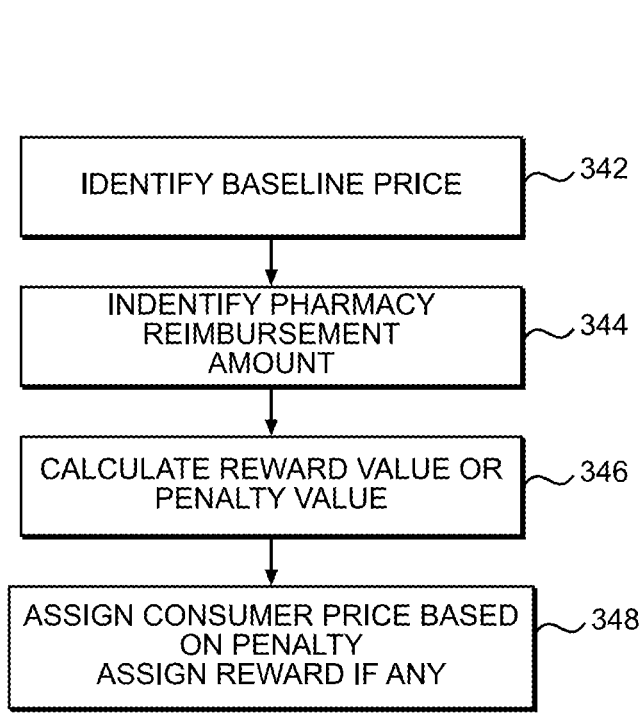
FIG. 3C is a flow diagram of an example price determination sub-routine that is consistent with at least some embodiments described herein.

Turning now to FIG. 3C, the process 300C illustrated therein is an example sub-routine that may be executed for each offer being assembled (e.g., for each pharmacy that will be defined in a particular offer), such that a respective Consumer Price to be included in each offer is determined. In accordance with some embodiments, process 300C may be performed by Pricing Module 224 (FIG. 2). It is again noted that process 300C is performed to determine a Consumer Price in scenarios where the consumer is no longer within the deductible period of his/her pharmacy benefit plan or the prescription drug for which offers are being assembled is a deductible exempt drug (such that the PBPP would be responsible for paying the PBM Price to the PBM if the PBM were to be utilized for filling the prescription).

At block 342 of process 300C, a Baseline Price is determined for the first offer being assembled. In accordance with some embodiments, the Baseline Price may be determined to be either a PBM Price or a Standard Baseline Price. In accordance with some embodiments, if the consumer is utilizing the APBM as an alternate prescription fulfillment mechanism parallel to the traditional PBM channel corresponding to the consumer's pharmacy benefit plan (the PBM associated with the consumer's PBPP), the Baseline Price may be determined to be the PBM Price for the prescription drug. As described herein, the PBM Price is the price the PBM would charge the PBPP for facilitating a fulfillment of a prescription of the drug under the consumer's pharmacy benefit plan. In accordance with one embodiment, the APBM may receive and store the PBM Prices for various PBMs from one or more sources and store them (e.g., in the drug pricing data 220 and/or the PBPP data 212 of memory 202, FIG. 2). For example, in one embodiment each PBPP with which the APBM has a relationship may provide the ABPM with a schedule of PBM Prices that it is charged by the PBM managing its pharmacy benefit plans. Thus, in one embodiment, if it is determined that a PBM Price is to be used for purposes of calculating a Consumer Price for an offer, the PBM Price may be retrieved from a database of the APBM (e.g., drug pricing data 220 of memory 202, FIG. 2).

In accordance with some embodiments, the APBM may not have direct access to, or confirmation of, a PBM price for a particular prescription drug. In such scenarios, the APBM may be operable to determine an estimated PBM Price, which may comprise a PBM Price that includes one of the following discount factors: (i) a generic discount factor (e.g., (0.39)*AWP of a generic drug); and (ii) a brand discount factor (e.g., (0.85)*AWP of the brand drug. The AWP comprises the "average wholesale price" for the drug, which is a published "sticker" price or average price for which wholesalers are said to sell the drug but that is not typically a true price that any entity pays for the drug (e.g., a MAC list price may be based on the AWP, and the Drug Cost a pharmacy paid to a wholesaler for the drug may be a portion of the AWP). In some embodiments, the APBM may have negotiated its own pricing contracts with one or more pharmacies and may utilize the prices or Pharmacy Reimbursement Amount from such pricing contracts.

In accordance with some embodiments, the brand discount factor may comprise an estimated rebate amount negotiated between a PBM and a drug manufacturer (which, in some circumstances, is at least partially passed on to a PPBP by the PBM) may be determined based on how many acceptable product substitutes (e.g., generic versions or brands that are similarly effective for a given condition) there are available for the brand drug (the more brand or generic substitutes there being available, the higher the brand discount factor). The following table illustrates one brand discount scheme that may be applied based on the number of product substitutes available for a brand drug:

TABLE 1

Brand Discount Factors

| # of drug alternatives | Estimated Rebate Amount |
|---|---|
| 6+ | 60% |
| 3-5 | 40% |
| 1-2 | 20% |
| 0 | 10% |

In accordance with one embodiment, the number of drug alternatives may be derived using online published exclusion lists from third party services such as Express Scripts™ or Caremark™ For example, if the exclusion list of Express Scripts™ specifies that drug A is excluded and drug B, C and D can be used instead, we would assume that each of drug A, B, C and D have 3 substitutes and assign each of them an estimated rebate of 40% based on the table above. In one embodiment, data such as that illustrated in Table 1 may be updated (e.g., periodically) based on new estimates of rebate levels from various sources. In accordance with one embodiment, the determination of the number of acceptable substitutes may be determined by polling clinical experts to get their views on which drugs can be substitutes for other drugs. In one embodiment, the APBM may "crowd-source" this information and allow qualified medical practitioners to weigh in with their judgments on substitutability and make such information available to consumers (e.g., by informing consumers and/or PBPPs that "X % of medical practitioners believe 'A' can be substituted for B'").

In another embodiment (e.g., in an embodiment in which the consumer and/or the PBPP is using the APBM as its stand-alone prescription fulfillment mechanism, not as a mechanism running in parallel with a PBM prescription fulfillment option), the Baseline Price may be determined to be a Standard Baseline Price calculated in accordance with a formula. For example, in one embodiment the Standard Baseline Price may be determined to be the lowest of:
  (i) the minimum Pharmacy Reimbursement Amount of the Pharmacy Reimbursement Amounts corresponding to a plurality of pharmacies identified as being within a first zone (e.g., pharmacies identified in accordance with process 300B to be within a comfort zone of the consumer's home location for the current prescription);
  (ii) 120% of the lowest Pharmacy Reimbursement Amount of the Pharmacy Reimbursement Amounts corresponding to a plurality of pharmacies identified as being within a second zone (e.g., pharmacies identified in accordance with process 300B to be within an economy zone of the consumer's home location for the current prescription); and
  (iii) 100% of the third lowest Pharmacy Reimbursement Amount of the Pharmacy Reimbursement Amounts corresponding to a plurality of pharmacies identified as being within the second zone (e.g., pharmacies identified in accordance with process 300B to be within an economy zone of the consumer's home location for the current prescription).

It should be understood that the above example formula for determining a Standard Baseline Price is intended as a non-limiting example and the embodiments described herein are not dependent on any particular formula for calculating a Standard Baseline Price. For example, other calculations that are based on a consideration of the Pharmacy Reimbursement Amounts corresponding to the pharmacies determined in process 300B may be substituted.

In accordance with some embodiments, a PBPP may be provided with a choice of different formularies to be utilized for its members, each formulary corresponding to a different Baseline Price formula or calculation. For example, in accordance with one embodiments, the APBM may offer to PBPPs three different formularies to choose from: Silver, Gold or Platinum (the names of the different levels or formularies are intended to be non-limiting, any differentiating names may be used). The different formularies may each correspond to a different formulas for how a Baseline Price is to be calculated when the APBM is generating offers for a particular prescription of a consumer and the PBPP may select a particular formulary based on how much they are willing or able to pay as their portion. For example, it may be assumed that there are three different types or cost levels of prescription drugs that may be utilized to fill a given prescription (e.g., first generic, second generic and brand). It may further be assumed, for purposes of the present example, that price level A corresponds to the lowest cost drug, level B corresponds to a mid-priced drug and price level C corresponds to the highest cost drug. In a Silver level formulary, the Baseline Price calculation may utilize the price of the A price level drug; this would result in the consumer normally having to pay an additional amount if (s)he selects an offer that defines either a B price level drug or a C price level drug. In a Gold level formulary, the Baseline Price may utilize a price that is the average of the A level price drug, the B level price drug and the C level price drug; this would result in the consumer normally receiving a Reward if (s)he selects an offer that defines the A price level drug but needing to pay an additional amount if (s)he selects an offer that defines the C price level drug. In a Platinum level formulary, the Baseline Price may utilize the price of the C level price drug; this would result in the consumer normally receiving a Reward if (s)he selects an offer that defines the drug corresponding to either the A price level or the B price level.

Next, in block 344, the Pharmacy Reimbursement Amount is identified. This is a determination of the monetary value that the pharmacy for which an offer is being assembled is expecting to be reimbursed by the PBM (or the APBM, if a pricing contract as agreed between the APBM and a pharmacy is being utilized to generate an offer) corresponding to the consumer's pharmacy benefit plan, if the consumer were to fill the prescription using the PBM channel. In accordance with some embodiments, the Pharmacy Reimbursement Amount may comprise an estimated or inferred Pharmacy Reimbursement Amount that is estimated or inferred by the APBM based on available but indirect information (since the Pharmacy Reimbursement Amount is often a confidential monetary value defined in a contract between a pharmacy and a PBM, and pharmacies are often contractually obligated to maintain such information as confidential). In accordance with one embodiment, the APBM may estimate or infer a Pharmacy Reimbursement Amount for respective prescription drugs as corresponding to particular pharmacies based on claims history data it receives from a claims processor (a third party entity that handles processing of reimbursements of Pharmacy Reimbursement Amounts from PBMs to pharmacies for prescriptions filled by the pharmacies). For example, the APBM may be operable to determine claims history information from a claims processor to determine which generic version of a drug a given pharmacy is stocking in its inventory. In one embodiment, the APBM may have access to a real time feed to one or more claims processors (in other embodiments, the APBM may receive this data periodically or non-periodically). The APBM may be operable to identify the particular generic being stocked by a given pharmacy based on the NDCs in the claims and therefrom determine the AWP for that generic using the published AWP lists that are publicly available ("NDC" being a National Drug Code, which is a unique 10-digit, 3-segment number that serves as a universal and unique product identifier for human drugs in the United States). In accordance with one embodiment, the APBM may then be operable to further estimate the Pharmacy Reimbursement Amount based on the AWP or MAC list corresponding to the particular brand or generic stocked by that pharmacy using published AWP or MAC lists and thus infer or estimate the Pharmacy Reimbursement Amount for a particular drug if it is filled at a particular pharmacy. It should be noted that the order of steps 342 and 344 may be reversed or the determinations of each may be performed simultaneously.

In accordance with some embodiments, the APBM may store an indication of various pricing contracts, each corresponding to a different PCN identifier, which list actual or estimated Pharmacy Reimbursement Amounts for specific prescription drugs. For example, in one embodiment the drug pricing data 220 (FIG. 2) may store an indication of the PCN identifier corresponding to each available Pharmacy Reimbursement Amount. In accordance with some embodiments, determining one or more Pharmacy Reimbursement Amounts for purposes of assembling one or more offers may comprise determining which pricing contract offers the lowest price (or the lowest set of possible prices) for the prescription drug for which offers are being assembled and identifying the PCN identifier corresponding to each such Pharmacy Reimbursement Amount that is selected for use in assembling an offer. In embodiments in which the APBM has negotiated its own pricing contracts with one or more pharmacies, such a PCN identifier may identify the Pharmacy Reimbursement Amount negotiated by the APBM.

In block 346, a reward or penalty value to be included in an offer is determined. In one embodiment, the functionality of determining a reward or penalty may be performed by the pricing module 224 as part of determining the Consumer Price while in other embodiments it may be performed as a separate sub-routine or by a different software module. This comprises comparing the Baseline Price (whether using the PBM Price as the Baseline Price or the Standard Baseline Price as the Baseline Price) to the Pharmacy Reimbursement Amount. If the Baseline Price is higher than the Pharmacy Reimbursement Amount, then it is determined that a potential reward should be calculated for inclusion in the current offer being assembled. If, on the other hand, the Drug Cost is higher than the Baseline Price, then it is determined that a penalty should be included in the Patient Price of the offer being assembled. Either the penalty value or the reward value may be based on the difference between the Baseline Price and the Drug Cost, although neither needs to be equal to that difference. In one embodiment in which a penalty is determined to be appropriate, the entire difference between the Drug Cost and the Baseline Price is determined to be the penalty and the penalty is added to the co-pay (or co-insurance amount, if any) that the consumer is responsible for paying under the terms of his pharmacy benefit plan and the sum is determined to be the Consumer Price for the current offer.

In accordance with some embodiments, an entity may make available one or more incentives (e.g., financial incentives, such as monetary amounts) that may be used to calculate a reward (or a net amount that a consumer would pay out of pocket, if the embodiment of FIG. 8A is being utilized) to be included in one or more offers being generated for a consumer. An entity may wish to make such incentives available for the APBM to use in generating offers in an effort to modify or influence the behavior of a consumer. For example, an entity may wish to incentivize the consumer to select an offer that defines drug X rather than the offer that defines drug Y (wherein one is a brand and the other is a generic or the two are different generics). In another example, an entity may wish to incentivize the consumer to select an offer that defines pharmacy or pharmacy location X rather than an offer that defines another pharmacy or pharmacy location Y (e.g., pharmacy X may wish to offer incentives to consumers who normally visit pharmacy Y, in an effort to get these consumers used to shopping at pharmacy X instead). In yet another example, a healthcare provider X may wish to offer an incentive to consumers in order to have them select an offer that defines that healthcare provider (e.g., a healthcare provider who is new in a community may be motivated to do this in order to attract new patients). An entity that may provide such incentives to be used to generate rewards amounts (or the net amount that a consumer would pay out of pocket) for offers may comprise, for example, a PBPP, a pharmacy, a drug manufacturer, the APBM and/or any party that may benefit from incentivizing the behavior of a consumer via an offer. An entity may define certain conditions or guidelines to be used in including an incentive amount in an offer. For example, an entity may define one or more consumer segments, characteristics or categories that a particular incentive amount (or range of incentive amounts) are to be used for. Some non-limiting examples of such segments, characteristics or categories include the following (the entity may specify a particular value or range of values within one or more of the following): (i) age; (ii) gender; (iii) socio-economic factors (e.g., salary, title, education); (iv) geographic location; (v) family size; (vi) family life cycle; (vii) medical history (e.g., prior drug usage, existing conditions, etc.) of the consumer and/or the consumer's family; (viii) APBM app usage statistics (e.g., value maximizers vs. convenience seekers).

In some embodiments, an evolving or self-learning algorithm may be used by the APBM to determine whether an incentive (or the magnitude of an incentive) should be included in a particular offer. For example, a reward module algorithm or module may evaluate a success rate of offering certain incentive amounts to certain types of consumers and re-adjust the incentive amount, whether the incentive amount is provided at all or which type of consumer it is offered to based on the results of such an evaluation. In some embodiments, the results of such an evaluation may be provided to the entity that is providing or funding the incentives such that the entity may, if desired based on the results, provide modified instructions or conditions for offering the incentives.

In accordance with some embodiments, if the Pharmacy Reimbursement Amount is less than PBM Price for a given pharmacy/offer, then the system determines that a Reward should be offered to the consumer for filling the prescription at this pharmacy. This is because having the consumer fill the prescription at the pharmacy will only cost the PBPP the lower Pharmacy Reimbursement Amount rather than the higher PBM Price. The value of the Reward may be based on the difference between the PBM Price and the Pharmacy Reimbursement Amount. In one embodiment, the system may be programmed to provide to the consumer as a Reward a certain percentage of the difference between the PBM Price and the Pharmacy Reimbursement Amount (e.g., 50%). In some embodiments, the percentage or portion of this difference that is to be offered to the consumer as a Reward may be selected by the PBPP of the consumer's pharmacy benefit plan (e.g., some PBPPs may desire for the consumer to share in more of the cost savings that will result from the consumer filling the prescription at this pharmacy via the APBM system than will others). Thus, in such latter embodiments, the APBM may be programmed to retrieve the percentage or portion as selected by the consumer's PBPP in order to calculate the final Reward value. Alternately, the calculation of the Reward to be included in an offer may be done in block 320 of process 300A (in the same or similar manner as described with respect to block 346 of process 300C).

If the Pharmacy Reimbursement Amount is determined to be higher than the PBM Price (such that it would cost the PBPP more if the consumer were to fill the prescription at this pharmacy via the APBM system rather than via the traditional PBM channel), a Penalty may be determined as appropriate for inclusion with the offer. The Penalty value may be based on (e.g., equal to) the difference between the Pharmacy Reimbursement Amount and the PBM Price. The Penalty value may be, for example, set such that the PBPP is made whole and does not incur any additional costs if the consumer accepts an offer for which the Pharmacy Reimbursement Amount is higher than the PBM Price (and/or to discourage the consumer from accepting such an offer).

Once the Reward value or the Penalty value are set, the Consumer Price is assigned for the offer in block 348 (the Consumer Price is also referred to a consumer's out-of-pocket cost or OPC herein). The Consumer Price may, in accordance with some embodiments, be set to be the consumer's co-pay amount (and co-insurance amount, if any) plus the penalty value (if any had been determined in block 346). In accordance with one embodiment, the consumer's co-pay (or co-insurance) amount may be retrieved from a record defining the consumer's pharmacy benefit plan (e.g., from consumer data 210, memory 202, FIG. 2). In accordance with some embodiments, the Consumer Price may not necessarily be set to the co-pay amount, even if the consumer has already satisfied the deductible amount and would otherwise be expected to pay the co-pay amount when filling the prescription via the traditional PBM channel. In accordance with some embodiments, the Consumer Price may be set to be the lower of the co-pay amount and the Pharmacy Reimbursement Amount.

The Reward value (if any, as determined in block 346) is also assigned to the offer. If there is an additional offer being assembled for the consumer (i.e., if the offer currently being assembled is not the last of the plurality of offers being assembled in response to a request from the consumer), the process 300C may return to block 342 and repeated for the pharmacy of the next offer. Otherwise, the sub-routine 300C may end and the APBM may return to block 318. If the Reward value had not been calculated as part of the calculation in block 346 of process 300C, it may be calculated in block 320 of process 300A.

Reference will now be made to FIGS. 4C-4F, which illustrate how a result of process 300A (including sub-routines 300B and 300C) may be output to a consumer via an APBM interface. Turning first to FIG. 4C, illustrated therein is a screen 400C that may be output on a mobile device 400 once a plurality of offers have been assembled for a consumer (e.g., the consumer who requested the offers by inputting information via the screen 400A and confirming the prescription details in screen 400B). For purposes of an illustrative example only, it may be assumed that it was determined (based on the pharmacy benefit plan information of the consumer stored by the APBM) that the consumer is no longer within a deductible period of the plan (i.e., the consumer has met the deductible amount of the plan, such that going forward the consumer is only responsible for a predetermined co-pay amount for prescriptions). In accordance with some embodiments, three (3) pharmacy fulfillment offers have been assembled for the consumer and are being output in area 430 of screen 400C. The first offer, 430A, defines a first pharmacy (Walmart™) and a first pharmacy location of that pharmacy that is indicated by the distance and estimated travel time relative to the consumer's search location (indicated in area 426 as being the consumer's home address). In some embodiments, if the consumer were to select the location symbol or name of the pharmacy, the consumer may be presented with specific information about the pharmacy location (e.g., an address and/or directions, in a pop-up window). The offer 430A also defines a Consumer Price of $5 (as indicated in the "Your Price" column of area 430) and a reward of $30 to be provided to the consumer if the consumer were to accept this offer and select this pharmacy location for fulfillment of the prescription in accordance with the terms of the offer. The second offer, offer 430B, defines a second pharmacy Durham™ (at a specific location that is a specified distance and estimated travel time from the consumer's home location) and that has a Consumer Price of $6 and a Reward of $30. Finally, the third offer 430C defines a third pharmacy Qualitas™ (at a specific location that is a specified distance and estimated travel time from the consumer's home location) and that also has a Consumer Price of $6 and a Reward of $30. Thus, as a visual comparison of the three example offers reveals, the offer that will be most financially beneficial to the consumer (because it has the lowest Consumer Price but the same Reward as the other two) is the least convenient in terms of distance and travel time.

It should be noted that screen 400C includes a mechanism, in area 428, via which the consumer may toggle between a view of the Reward corresponding to each offer and a view of the Estimated Non-APBM Price corresponding to each offer. Screen 400D (FIG. 4D) illustrates the alternate view that can, in some embodiments, be output to the consumer if the consumer selected to view the Estimated Non-APBM Prices rather than the Rewards corresponding to each offer. As each of offers 430A, 430B and 430C indicate in area 430 of screen 400D, the Estimated Non-APBM Price for each offer is $10. In the present example, it may be assumed that the co-pay the consumer would be expected to pay if he/she were to fill the prescription using the traditional PBM channel (i.e., not using the APBM app/system), is $10. The Estimated Non-APBM Price is the price the consumer would pay for filling the prescription using the traditional PBM channel (in the present example this being the $10 co-pay). Thus, the consumer can readily appreciate that if he/she were to fill the prescription via the APBM system, he/she would pay $5 or $6 out-of-pocket and receive a $30 reward while if he/she were to not accept any of the offers in area 430 and instead choose to fill the prescription in the conventional manner using the PBM channel, his/her out-of-pocket cost would be $10 and he/she would receive no reward.

It may be assumed, for purposes of the example of FIGS. 4C-4F, that the Pharmacy Reimbursement Amounts for offers 430A, 430B and 430C were determined (e.g., via sub-routine 300C) to be $5, $5 and $6, respectively. Thus, in accordance with some embodiments, the Consumer Price was assigned in each offer to be the Pharmacy Reimbursement Amount, since in each case this was lower than the consumer's co-pay amount. Turning now to FIG. 4E, illustrated therein is a screen 400E that may be output to the consumer in response to the consumer selecting one of the offers output in screen 400D. For purposes of the present illustrative example, it may be assumed that the consumer selected offer 430A and screen 400E has popped up (as window 435A) to indicate the details of the offer (including the details of the prescription) and provide the consumer with an opportunity to accept the offer (e.g., by actuating the virtual button 434 on screen 400E). It should be noted that the screen 400E outputs additional detail regarding the offer 430A, including a breakdown of (i) the employee (consumer) OPC (which is $5 in the present example), 431; (ii) the employer (PBPP) cost (which is $0, since the $5 to be paid by the consumer/employee is the Pharmacy Reimbursement Amount in this case, such that the employer is not responsible for any additional payment; and (iii) the Reward to be provided to the consumer upon fulfillment of the prescription in accordance with the offer (which is $30 in the present example), 433.

It may be assumed, for purposes of the present example, that the PBM Price of the prescription drug that is the subject of offers 430A, 430B and 430C is $65. In other words, if the consumer were to fill the prescription via the traditional PBM channel and not via the APBM system/app, the PBM would charge the PBPP $65 for facilitating the fulfillment of this prescription and that the consumer would be responsible for $10 of this PBM Price (the consumer's co-pay amount) while the PBPP (e.g., employer) would be responsible for the remaining $65. Thus, if the consumer were to choose to fill the prescription via the APBM system/app and pay only the $5 or $6 Consumer Price (depending on which offer the consumer accepts), and the Consumer Price being the Pharmacy Reimbursement Amount, the PBPP would not be responsible for paying its portion of the $65 PBM Price to the PBM. The difference between the PBM Price and the Pharmacy Reimbursement Amount is $60 (for the pharmacy with the $5 Pharmacy Reimbursement Amount) or $59 (for the pharmacy with the $6 Pharmacy Reimbursement Amount). In accordance with some embodiments, the Reward for each offer may be set to be 50% of this difference, rounded to the nearest dollar (of course, any % or portion may be used and the 50% is used merely as a non-limiting example). This calculation accounts for the $30 reward to the consumer, which the PBPP will ultimately fund because paying this $30 Reward to the consumer still results in significant savings to the PBPP.

In accordance with some embodiments, if a consumer elects to accept an offer, the consumer's acceptance may be stored in the system and an electronic prescription card may be generated by the system. An example of such a prescription card for offer 430A is illustrated in area 435B of screen 400F (FIG. 4F). In some embodiments, such an electronic prescription card may be utilized by the consumer to fill the prescription at the pharmacy. In other embodiments, the consumer may be provided with a static electronic prescription card on which the BIN/PCN identifier identifies the APBM such that a pharmacy at which the consumer presents the card places a request for fulfillment of the prescription to the APBM and the APBM may, in turn, route the request to a PBM if a PBM pricing contract is going to be utilized to fill the prescription (more details regarding such an embodiment are provided with reference to FIGS. 5, 6B, 7 and 8). Consistent with at least some embodiments, the electronic prescription card 435B may include details of the prescription (in area 435B-1) and APBM details that will allow a pharmacy claims system to process a claim for the prescription (in area 435B-2). With respect to area 436B-2 and the prescription BIN and prescription PCN identifiers illustrated thereon, it should be noted that the digital prescription card may include a BIN (Bank Identification Number, which identifies a PBM (or the APBM, in the case of embodiments described herein with reference to FIGS. 5, 6B, 7 and 8), associated with the processing of the prescription), a PCN (Processor Control Number, which identifies the particular APBM or PBM Network or pricing contract corresponding to the prescription) and a Group identifier (which identifies a plan of the consumer attempting to fill the prescription). Each of these identifiers helps facilitate a pharmacy and/or claims processor in processing the prescription by indicating the pricing contract that corresponds to the prescription fulfillment offer.

Returning now to block 312, in this block a Consumer Price may be calculated for each of a plurality of offers being assembled for a consumer/prescription in a scenario in which the consumer has not yet met his deductible amount and the prescription drug for which prescription fulfillment offers are being assembled is not a deductible exempt drug. In other words, the consumer is responsible for the full cost of the prescription drug, not just the co-pay (whether this be the PBM Price if the consumer chooses to fill the prescription using the traditional PBM channel or the APBM Consumer Price if the consumer chooses to fill the prescription using the APBM system/app). In such a scenario, no rewards are calculated or provided to the consumer (since the PBPP is not responsible for any portion of the cost of the prescription drug and thus does not have any potential savings to pass on to the consumer in the form of a reward). Rather, the Consumer Price is determined to be the Pharmacy Reimbursement Amount for each pharmacy defined by each respective offer. In some embodiments, the Consumer Price may also include a Penalty that is added to the Pharmacy Reimbursement Amount. The Penalty may be added if, as described with respect to block 346 of sub-routine 300C, the Pharmacy Reimbursement Amount is determined to be higher than the PBM Price or estimated PBM Price for the offer. In block 314, the PBM Price or estimated PBM Price is determined. The determination of a PBM Price or estimated PBM Price was described with respect to block 342 of process 300C and will not be repeated herein for purposes of brevity.

In block 316, a the one or more offers assembled for the consumer is output via an APBM GUI. If the process 300A flows to block 316 from block 320, the output comprise information such as indicated in FIGS. 4A-4F. If, on the other hand, the process 300A flows to block 316 from block 314 (in which scenario there are no Rewards to offer to the consumer), the output may include, for each offer included in the menu of offers, a comparison of the Consumer Price (which often will be based on the Pharmacy Reimbursement Amount for each pharmacy) to the PBM Price or estimated PBM Price that the consumer would otherwise pay for the prescription, thus allowing the consumer to appreciate the savings he/she can realize (which can be considered a reward in and of itself) by filling the offer via the APBM System and thus paying the Pharmacy Fulfillment Price rather than the typically higher PBM Price.

In accordance with some embodiments, once a plurality of offers is output to a consumer and the consumer accepts an offer, additional steps or another sub-routine of APBM may be initiated. For example, as described herein, in some embodiments the consumer pays the Consumer Price for an accepted offer directly to the APBM using the APBM app and thus has nothing to pay to the pharmacy at the point-of-sale when filling his/her prescription using the APBM electronic prescription card. In such embodiments, once the consumer accepts an offer he/she may be routed to a payment process via which the consumer provides payment of the Consumer Price to the APBM. In one embodiment, the consumer may previously have stored credit card or other financial account information with the APBM (or provided with the APBM to charge fees to such credit card or other financial account) and thus the payment process may simply comprise having the consumer confirm the Consumer Price that is to be charged and authorizing the payment. In other embodiments, the consumer may need to input payment information. In yet other embodiments, the consumer may need to provide the Consumer Price at the point-of-sale to the pharmacy and the pharmacy and APBM may reconcile at a later point.

Further, in some embodiments once a consumer accepts an offer the APBM may transmit information regarding the offer to a claim processor (e.g., claim processor 150) that will be expected to process the claim from the pharmacy location defined by the accepted offer. The information transmitted to the claim processor may be whatever information the claim processor requires to approve and process the claim when a request for it comes through from the pharmacy location. Thus, the claim processor may, in accordance with some embodiments, open a pending claim or record for the offer (which, in some embodiments, may expire after a specified time) upon receiving the information from the APBM.

Turning now to FIG. 4G, illustrated therein is an example screen 400G, which may be output to a consumer who is a registered user of the APBM, and allow the user to view and manage the various prescription offers the consumer has accepted and/or filled via the APBM. In accordance with some embodiments, area 441 of screen 400G allows a consumer to view or manage (e.g., delete) information on prescriptions which the consumer has entered information for but for which the consumer has not yet selected a prescription fulfillment offer (in accordance with one embodiment, the user may request offers to be assembled for such a prescription by actuating the virtual button 442). Also in accordance with some embodiments, area 443 allows the consumer to view or access information on prescriptions for which the user has accepted a fulfillment offer but which prescription the consumer has not yet filled (in accordance with some embodiments, such an offer may expire if not filled within a predetermined period of time, as indicated in area 443). Also in accordance with some embodiments, area 444 allows the consumer to view or access information on prescriptions that the consumer has filled via the APBM system.

It should be noted that a consumer may be able to view and manage prescriptions for other persons (e.g., other family members who are covered under the consumer's pharmacy benefit plan). Thus, in such embodiments, a screen such as screen 400G may allow the consumer to view and manage prescriptions for such other people (e.g., view an electronic prescription card for a child or spouse's prescription such that the consumer can go to a pharmacy to fill the prescription).

Turning now to FIG. 4H, illustrated therein is an example screen 400H that allows a consumer to view or manage (e.g., redeem) rewards earned by the consumer by accepting prescription fulfillment offers via the APBM. In accordance with some embodiments, the storing, managing and facilitating of pending and earned rewards, as well as the redemption of earned rewards, may be facilitated by reward module 228 (FIG. 2).

In accordance with some embodiments, some offers output to a consumer may include an indication of a Reward to be provided to the consumer upon the consumer accepting the offer and filling the prescription in accordance with the terms of the accepted offer. In some embodiments, such Rewards may define monetary value amounts that can be redeemed at partner merchants (e.g., Amazon™ or Walmart™). For example, in some embodiments such Rewards may be used as store credit or to purchase gift cards to such partner merchants. Area 451 of the example screen 400H indicates a value of Rewards that are pending. Rewards that are pending may comprise, for example, Rewards for offer(s) the consumer (or others associated with the consumer's APBM account, such as children or a spouse that may be covered under the consumer's pharmacy benefit plan) has accepted but has not yet filled the prescription in accordance with the terms of the offer(s). Area 452, on the other hand, indicates a value of Rewards that are available for redemption (e.g., Rewards for offers that have been accepted and for which the prescriptions have been filled in accordance with the terms of the offer). In accordance with some embodiments, redeeming a value of Rewards may comprise (i) using the Rewards to purchase gift cards or store credit for use with one or more merchants; (ii) requesting a check or deposit of the monetary value to be made to a bank account associated with the consumer; or (iii) requesting that a value of the Reward be applied to a Consumer Price corresponding to a new offer output to the consumer via the APBM.

Reference will now be made to a particular embodiment that is illustrated via FIGS. 5, 6B, 7 and 8 (referred to as the "ABPM as switchboard" embodiment), one in which consumers who utilize the APBM for prescriptions by providing to the pharmacy of their choice the BIN/PCN of the APBM (e.g., the pharmacy prescription benefit card or app of the APBM may store such BIN/PCN) when filling a prescription. In this embodiment, the pharmacy forwards a request for the prescription claim (i.e., a request from a pharmacy for approval to fill a prescription, based on a prescription provided to the pharmacy by a consumer) to the APBM by transmitting a data packet consisting of certain first data (e.g., data identifying the prescription, the consumer and the pharmacy). The APBM processes the prescription claim by either (i) approving and adjudicating the prescription claim based on its own pricing contract negotiated with the pharmacy (in which case the APBM is the entity that will be responsible for paying to the pharmacy the Pharmacy Reimbursement Amount for the prescription); or (ii) selecting a pricing contract negotiated between the pharmacy and a PBM for filling the prescription, approving and pre-adjudicating the prescription claim based on that pricing contract, modifying the data packed defining the prescription claim request as received from the pharmacy (based on the pre-adjudicating) and transmitting the modified data packet to the selected PBM (and in which case the PBM is the entity that will be responsible for paying to the pharmacy the pharmacy Reimbursement Amount for the prescription).

Figure 5:
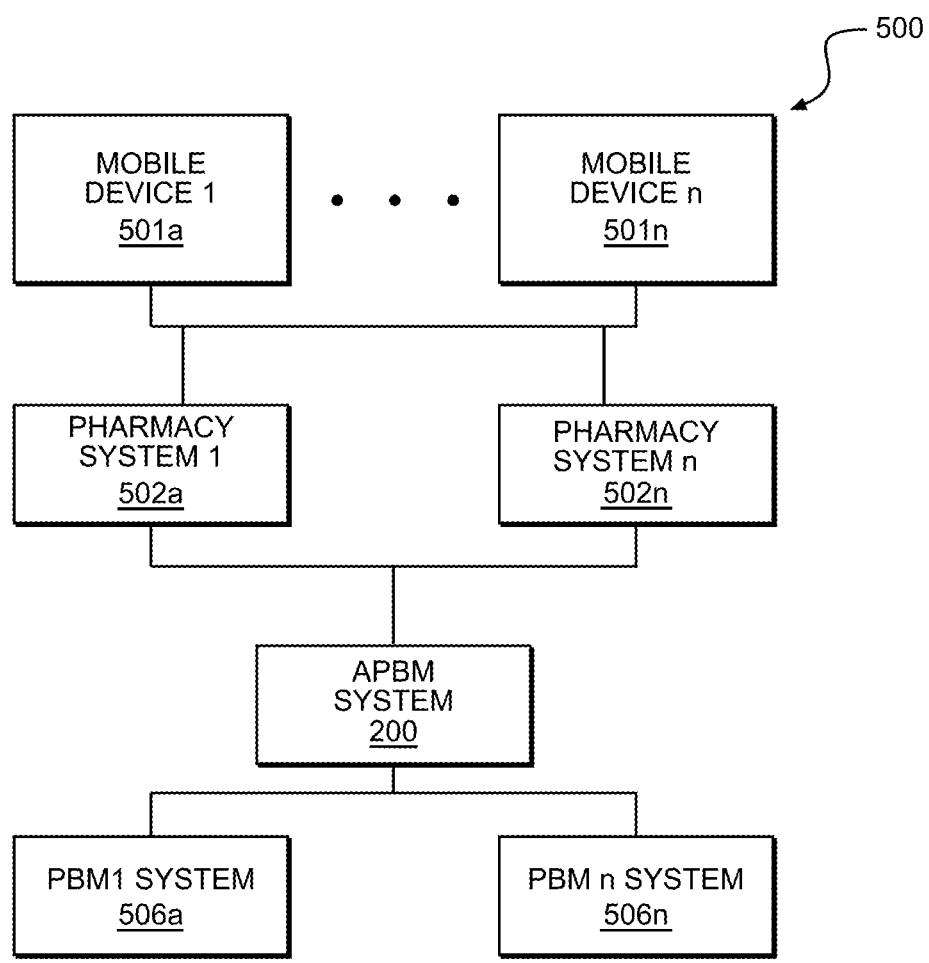
FIG. 5 is a block diagram of an alternate view of a system for facilitating redemption of a prescription, consistent with at least some embodiments described herein.

Referring now to FIG. 5, illustrated therein is an example system 500, for facilitating requests for prescription claims in accordance with the "APBM-as-switchboard" embodiment. In embodiments utilizing system 500, the APBM System may maintain a static electronic prescription plan identifier or set of identifiers for its consumers. In other words, a given consumer's prescription benefit plan indicator (whether a physical card or a bar code, QR code or other indicator output on a GUI of an app that the consumer may present to a pharmacy when attempting to fill a prescription) remains the same for multiple prescriptions, this indicator including an identifier comprising a BIN/PCN identifier that identifies the APBM and is utilized by a pharmacy to send a prescription claim request to the APBM upon a consumer presenting himself/herself at the pharmacy and requesting to fill the prescription utilizing the BIN/PCN identifier of the APBM as identified on the consumer's prescription plan indicator (e.g., physical card or electronic card output on a GUI of the APBM app). The prescription benefit plan indicator may further include a member identifier that uniquely identifies the consumer to the APBM, and which is also transmitted to the APBM by the pharmacy in a submission for a prescription to be filled. In such embodiments, while the APBM System may continue to select the a particular PBM pricing contract (which may correspond to a particular BIN/PCN identifier combination of the associated PBM) based on the best prices for a specific drug at a specific time for a specific retailer, the consumer's prescription benefit card (or the BIN/PCN identifier as stored in the APBM App of the consumer and shown to a pharmacist) may be one that corresponds to the APBM. In some embodiments, neither the consumer nor the pharmacy may know, at the time the consumer presents himself or herself at the pharmacy in order to fill a prescription, the BIN/PCN identifier of the PBM or PBM price contract that the APBM will use to fill the prescription. Further, while in some embodiments the BIN/PCN identifier of the pricing contract may be stored in the APBM's database as corresponding to a particular prescription (e.g., in embodiments in which the consumer had reviewed various offers and selected one, such as described with respect to FIGS. 4A-4H) in other embodiments the APBM may select the pricing contract and/or PBM to be utilized in furtherance of fulfillment of a particular prescription at the time the request to fill the prescription is received from a pharmacy (e.g., a consumer may not review and select offers ahead of time or the APBM may reserve the right to review and select its preferred pricing contract and/or PBM at the time a request for filling a prescription is received from a pharmacy).

The system 500 includes various components for facilitating the processing of requests for prescription claims, including (i) a plurality of mobile devices 501 of consumers; (ii) a plurality of pharmacy systems 502; (iii) the APBM System 200; and (iv) a plurality of PBM Systems 506. The mobile devices 501 may be the same as the mobile devices 120 of system 100 (FIG. 1), the pharmacy systems 502 may be the same as the pharmacy systems 130 of system 100 (FIG. 1) and the APBM 200 may be the same as the APBM 200 of FIGS. 1 and 2. Thus, a detailed description of these components and the functionalities they may perform will not be repeated; rather, the detailed description provided earlier herein for such components is incorporated by reference herein from the description provided with reference to FIGS. 1 and 2 and elsewhere herein. The PBM Systems 506 may each comprise one or more servers operated by or on behalf of respective PBMs. As illustrated in FIG. 5, the APBM is embodied, in terms of communication processing, between the pharmacy systems 502 and the PBM systems 506, thus positioned to route requests for prescription claims to a PBM it selects (or based on a selection of an offer from a consumer) for fulfillment of a prescription.

Although not illustrated in FIG. 5, it should be understood that the various components of system 500 may communicate with one another via one or more networks. Such networks may comprise, for example, a mobile network such as a cellular, satellite, or pager network, the Internet, a wide area network, a Wi-Fi network, another network, or a combination of such networks. For example, in one embodiment, both a wireless cellular network and a Wi-Fi network may be involved in routing communications and/or transmitting data among two or more devices or components illustrated in FIG. 5. The communication between any of the components of system 500 may take place over one or more of the following: the Internet, wireless data networks, such as 802.11 Wi-Fi, PSTN interfaces, cable modem DOC SIS data networks, or mobile phone data networks commonly referred to as 3G, LTE, LTE-advanced, etc.

In some embodiments, additional devices or components that are not show in FIG. 5 may be part of a system for facilitating the APBM-as-switchboard embodiment as described herein. For example, one or more servers operable to serve as wireless network gateways or routers may be part of such a system. In other embodiments, some of the functionality described herein as being performed by system 200 may instead or in addition be performed by a third party server operating on behalf of the system 200 (e.g., the APBM may outsource some functionality, such as registration of new consumers or managing the redemption of rewards earned by consumers). Thus, a third party server may be a part of a system such as that illustrated in FIG. 5.

It should be understood that any of the functionality described herein as being performed by a particular component of the system 500 may in some embodiments be performed by another component of the system 500 and/or such a third party server. For example, one or more of the functions or processes described herein as being performed by APBM System 200 (e.g., a module or software application of the APBM System 200) or another component of system 500 may be implemented with the use of one or more cloud-based servers which, in one embodiment, may be operated by or with the help of a third party distinct from the APBM. In other words, while in some embodiments the APBM System 200 may be implemented on servers that are maintained by or on behalf of an APBM, in other embodiments it may at least partially be implemented using other arrangements, such as in a cloud-computing environment, for example.

In accordance with some embodiments in which a consumer's prescription benefit indicator (e.g., electronic or physical card) is one that includes a static identifier or set of identifiers usable for fulfillment of multiple prescriptions (e.g., the identifiers include a BIN/PCN and/or Group Identifier that identifies the APBM), the dynamic sourcing for the best contracted pricing may continue to be processed and selected on the backend via a processor of the APBM based on information provided by the consumer and pricing information available to the APBM (e.g., as described with respect to FIGS. 3A-3C), whether prior to the consumer's visit to the pharmacy or upon a request for a prescription fulfillment being received from a pharmacy. The communications and/or interactions of the APBM with a PBM and/or pharmacy in processing fulfillment of a request for a prescription claim may comprise (i) the APBM communicating with the pharmacy directly to authorize fulfillment of a prescription and provide information allowing the consumer to obtain the prescription at the pharmacy (e.g., an indication of a Consumer Price the consumer is to pay the pharmacy directly); and (ii) the APBM communicating with a selected PBM in order to inform the PBM that a prescription is being fulfilled based on their pricing contract with a pharmacy such that the selected PBM can subsequently close the transaction by providing the pharmacy with the appropriate Pharmacy Reimbursement Amount. As described in detail elsewhere herein, the APBM may select for fulfillment of a particular prescription a particular pricing contract and/or BIN/PCN combination for a particular PBM from one of two sources: (i) from a contract the APBM has in place directly with a pharmacy or pharmacy location; or (ii) from a leased contract or price list that has been negotiated with a PBM (e.g., if the best or lowest price for a given pharmaceutical drug happens to be found by the APBM in a price list negotiated between a PBM and the pharmacy rather that in a price list negotiated between the APBM and the pharmacy). In scenario (i), the APBM may not forward the prescription fulfillment data to any PBM but may simply authorize the fulfillment of the prescription and provide the appropriate pharmacy reimbursement amount at a later time directly to the pharmacy. In scenario (ii), the APBM may forward the prescription fulfillment request received from the pharmacy (e.g., in modified form, based on a pre-adjudication, as described herein) to the PBM corresponding to the price list selected for fulfillment of the prescription, such that this PBM may subsequently provide the Pharmacy Reimbursement Amount to the pharmacy. In scenario (ii) the APBM may be acting effectively as a switchboard that routes the prescription fulfillment request to the appropriate PBM once it received a request for a prescription claim from a pharmacy (and the pharmacy may be providing the request to the APBM based on the BIN/PCN that identifies the APBM as indicated on the consumer's pharmacy benefit indicator or card). Further, in scenario (ii) the pharmacy may not be aware that the request for a prescription claim is being forwarded to a third party (the selected PBM) and the APBM may pre-adjudicate the claim request and modify a data packet comprising the request received from the pharmacy, such that the data packet that is then forwarded by the APBM to a PBM includes data that is different from and/or in addition to that received from the pharmacy (as described in more detail below).

As described in relation to other embodiments described herein, in some embodiments the pharmacy may contact the relevant PBM directly, based on a BIN/PCN identifier(s) on the consumer's electronic prescription card that identifies the PBM, and a payment loop would close as it does under prior art methodologies when consumers use a traditional PBM (one that is illustrated and described with reference to FIG. 6A). In accordance with the alternate methodologies and infrastructures illustrated in FIGS. 5, 6B, 7 and 8, however, the pharmacy may initiate a transaction (a request for fulfillment of a prescription, also a referred to as a prescription claim herein) directly with the APBM System (or a subsidiary, affiliate or contractor thereof, tasked with communications with pharmacies at which a consumer is attempting to redeem a prescription for which the APBM System is identified in the BIN/PCN identifier provided by a consumer, collectively referred to as the APBM System for purposes of simplicity). In the embodiments relevant to the system and methodologies of FIGS. 5, 6B, 7 and 8, it is a static BIN/PCN and/or Group Identifier on a consumer's prescription benefits card that identifies the APBM System as the "PBM" that is being used for the transaction and that, in turn, allows the APBM to pull up the consumer's accepted offer(s) (or select a pricing contract for fulfillment of the prescription at the time of receiving the request) and determine whether to authorize the transaction at the pharmacy. On the backend, upon receiving a communication from a pharmacy indicating that a consumer is requesting to fulfill a prescription, the processor of the APBM initiates a communication with the PBM that the APBM System has identified as having the best price for that prescription drug at that pharmacy (e.g., the PBM that was identified or associated with in the offer accepted by the consumer or the PBM that the APBM determines, at the time of receiving the request for a prescription claim from a pharmacy, has the best Consumer Price for the prescription), and the APBM System communicates with that PBM regarding the transaction.

Figure 6A:
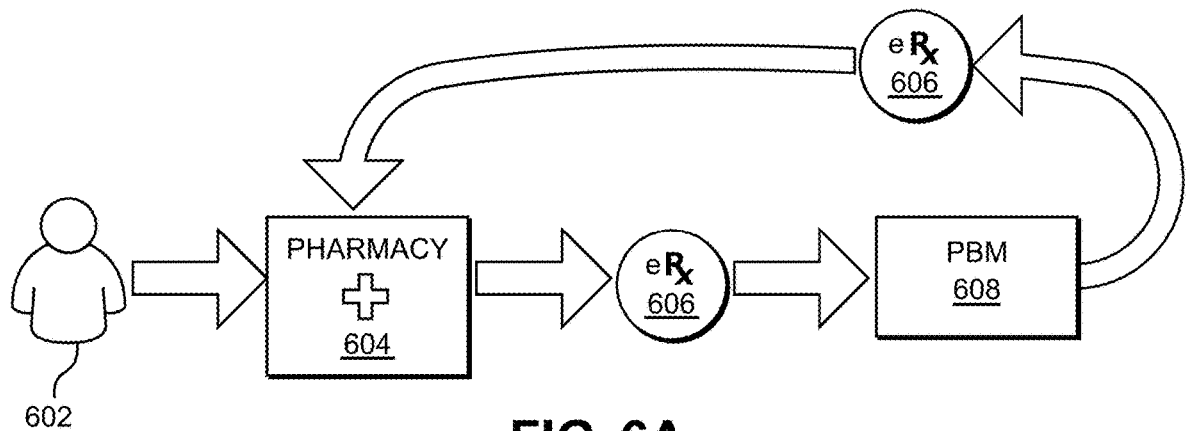
FIG. 6A comprises an example of a data processing infrastructure for processing requests for prescription fulfillment, as it occurs in the prior art.

Referring now to FIG. 6A, illustrated therein is an illustration of the data flow for how a request for a prescription claim is currently processed for approval under prior art infrastructure and processes. A consumer (602) presents a prescription to a pharmacy that he/she would like filled at the pharmacy. The consumer may provide a BIN/PCN identifier on his/her prescription benefit card or indicator (e.g., as indicated on a printed card that the consumer presents to the pharmacy or has previously presented to the pharmacy and is stored in the pharmacy's records). The BIN/PCN identifier identifies the PBM that is affiliated with prescription benefit plan of the consumer and the pricing contract or network that corresponds to the prescription benefit plan. The pharmacy submits a request for a prescription claim to the PBM (or claims processor of the PBM), via the eRx Network™ 606 or another secure and specialized network for requesting approvals of prescription claims. The pharmacy does this for the particular prescription the patient has from his/her the doctor (digital or physical script) by transmitting certain data to the PBM 608 (or claim processor thereof), such as the patient's prescription plan card details (most of the time these are keyed in once and then stored in the pharmacy system), the consumer details (e.g., consumer's member identifier, name, date of birth) and the prescription details (e.g., which particular drug is to be used to fill the prescription). The PBM or claim processor then adjudicates the prescription claim, such as by (i) checking eligibility by confirming if the individual whose name is on the prescription is still active in the census file that comes from the PBPP associated with the plan identified via the prescription plan card; (ii) cross-checking the prescription details against the plan formulary to determine if the drug is covered and/or if any restrictions apply, and (iii) checking whether the consumer has met any applicable deductibles. The claim processor then sends back a message to the pharmacy 605, via the eRx Network™ 606 either (i) approving the claim and confirming the consumer is eligible, the drug is covered, and indicating the amount the pharmacy should charge the consumer at the point of sale (the Consumer Price), such as the co-pay amount if the consumer has satisfied the deductible amount or the PBM Price if the consumer has not yet satisfied the deductible amount; or (ii) denying the claim (e.g., if either the eligibility or drug coverage are not confirmed by the claim processor, the message that is sent to the pharmacy from the claim processor indicates that the prescription is "rejected" (and may include a brief description indicating the reason for the rejection)).

As described above, a PBM enters into PPAs with various pharmacies, a PPA between a PBM and a pharmacy defining the rates at which a pharmacy company will be reimbursed by the PBM for both brand and generic drugs. The PPAs are often confidential and include the pricing terms between a PBM and the pharmacy, one of which terms may specify an amount of money the PBM has to reimburse the pharmacy for drugs (usually structured as a Generic Effective Rate, GER, for generic drugs, which measures the reimbursement for an entire basket of drugs rather than pricing each drug individually; for example, a PPA may specify that for every $1 of "AWP" the pharmacy will receive $0.20 in reimbursement). A PBM may resell their network of pharmacy agreements to a PBPP at a markup (e.g., an agreement with a PBPP may specify that the PBPP will only pay $0.30 on every dollar of AWP when the PBM has agree to pay pharmacies $0.20 on every dollar of AWP), such that the PBM profits from the spread between the pricing it reimburses to the pharmacy and the amounts it charges to its client PBPPs (e.g., in the present illustrative example the profit is a 50% mark-up, ($0.30–$0.20)/$0.20). However, to know exactly what price each drug needs to be reimbursed at, the PBM provides a MAC list to the pharmacy (and a separate one that's marked-up to the client PBPP) that essentially offers an itemized price list per drug. The individual prices on the MAC list, multiplied by the actual volumes filled for each generic drug, should come close to the target GER that the PBM contracted with the pharmacy. A given PPA includes a specific BIN and PCN identifier that it corresponds to. The BIN identifies the PBM. And within that PBM's network, the PCN identifies a specific account that can have its own specific set of prices and unique MAC lists. Thus, a claim processor that receives a request for a prescription claim from a pharmacy determines the BIN/PCN identifiers corresponding to the request (e.g., from the consumer's Prescription Plan card as provided by the pharmacy with the request) and, if the request is approved based on the eligibility and drug coverage verifications, determines the price that the consumer is to be charged for the prescription based on the BIN/PCN and returns this information to the pharmacy. It should be noted that, in the traditional pharmacy fulfillment process involving a PBM and the pharmacy's communication with a claim processor when the consumer is filling a prescription (such as illustrated in FIG. 6A), the consumer is using a static BIN/PCN set of identifiers that are on his/her prescription plan card issued by his/her PBPP and that identifies the PBM that the PBPP has contracted with and the particular PCN corresponding to that PBM contract/network associated with the consumer's pharmacy benefit plan.

In the traditional prescription claim approval process illustrated in FIG. 6A, the pharmacy system (604) initiates a request for a prescription claim via a communication to a secure, specialized network for facilitating prescription claims. The communication comprises a request for a prescription claim and includes a data packet or file that indicates (i) the BIN/PCN of the PBM that is affiliated with the consumer's prescription benefit plan; (ii) an identifier of the consumer and/or consumer's group plan; (iii) information identifying the patient who is requesting to fill the prescription (e.g., name and date of birth); (iv) an indication of the prescription drug that the prescription will be filled with (e.g., generic or brand name, dosage or strength, form, size, etc.); (iv) the current date; and (v) an indication of the pharmacy that is submitting the request for the prescription claim. Of course, additional detailed data may be included in such a data packet or file, as desired. In FIG. 6A (as well as in FIG. 6B) this prescription claim network is illustrated as eRx Network™ 606, although another dedicated prescription claim network may be utilized. The eRx Network™ 606 forwards the request/data packet or file to the PBM identified in the BIN/PCN field of the data packet. The PBM adjudicates the prescription claim (e.g., determines whether to authorize the claim based on the consumer's prescription benefit plan). A description of the various steps and determinations that may comprise a prescription claim adjudication are described elsewhere herein and will not be repeated for purposes of brevity.

Once the prescription claim is adjudicated, the PBM 608 returns a response to the request for the prescription claim in a communication that is transmitted to eRx Network™ 606, which in turn forwards the response to the pharmacy 604. The response to the request for a prescription claim may comprise, for example: (i) an approval/authorization or denial of the prescription claim; (ii) if the prescription claim is approved/authorized, an indication of the Consumer Price the consumer is to pay the pharmacy; and (iii) if the prescription claim is denied, a suggestion for an alternate prescription drug for filling the prescription (e.g., a generic substitute). Thus, as can be appreciated from the data process flow illustrated in FIG. 6A, the pharmacy initiates a request for a prescription claim via the eRx Network™ 606 and receives a response thereto, also via the eRx Network™ 606. If the prescription claim is authorized, the pharmacy then also expects to eventually receive, from the PBM that authorized the claim, the Pharmacy Reimbursement Amount as previously negotiated, as set forth in a PPA, between the pharmacy and the PBM for the prescription drug that was authorized for filling the prescription.

It should be noted that a unique transaction identifier is assigned to the request for the prescription claim by the PBM (or, in some embodiments, by the eRx Network™ 606) and this unique transaction identifier is referenced in the response to the request that is returned to the pharmacy via the eRx Network™ 606 and in the payment for the Pharmacy Reimbursement Amount that the PBM subsequently provides to the pharmacy. The pharmacy system 404 may, for example, store an indication of the transaction identifier received for the request for a given prescription claim and, when Pharmacy Reimbursement Amounts are subsequently received from a given PBM (which may be provided along with a report that includes the unique transaction identifier of each approved claim for which a Pharmacy Reimbursement Amount is being paid), to verify that Pharmacy Reimbursement Amounts have been received for all approved prescription claims, as expected.

Figure 6B:
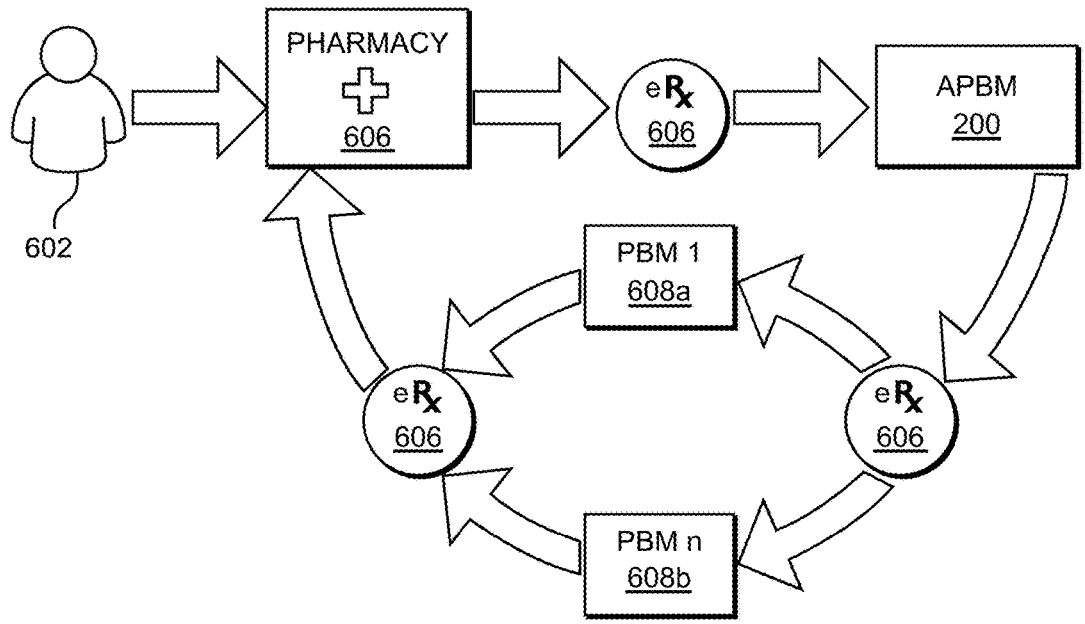
FIG. 6B comprises an example of a new data processing infrastructure that is consistent with at least some embodiments described herein.

Applicant has endeavored to create a system (the APBM-as-switchboard embodiment described herein) that not only allows a consumer to realize savings (and sometimes rewards) when filling prescriptions at a pharmacy, but to be able to do so (i) while having the prescription go through the consumer's prescription benefit plan (such that the Consumer Price is counted towards the deductible and the health benefit plan administrator is aware of all the prescriptions being filled by the consumer, for purposes of tracking drug interactions, allergies, adherence to prescriptions, etc.); and (ii) while minimizing any disruptions or modifications to the pharmacies, such that retraining of pharmacy personnel and/or re-programming of pharmacy systems and processes is unnecessary or minimal. The APBM-as-switchboard embodiment described with reference to FIG. 5 will now be described with reference to FIG. 6B. FIG. 6B illustrates in a graphical format some relevant differences between how a prescription claim is processed and approved within Applicant's APBM-as-switchboard infrastructure as compared to the traditional prescription claim processing infrastructure described with reference to FIG. 6A. FIG. 6B also illustrates how these difference may be transparent to the pharmacy and consumer such that, from the perspective of the pharmacy and consumer, the prescription claim process of FIG. 6B appears very similar to the traditional process of FIG. 6A. The data flow diagram of FIG. 6B will be described with reference to process 800 (FIG. 8), which follows the data flow and infrastructure illustrated in FIG. 6B.

The prescription claim process in FIG. 6B begins, from the perspective of the pharmacy and the consumer, in a manner that appears the same as the traditional process illustrated in FIG. 6A: the consumer (602) presents a prescription to a pharmacy and request that it be filled by the pharmacy. The consumer may provide a BIN/PCN identifier on his/her prescription benefit card or indicator (e.g., as stored on the APBM app downloaded on the consumer's mobile phone or on a printed card that the consumer presents to the pharmacy or has previously presented to the pharmacy and is stored in the pharmacy's records), either at the time of filling a particular prescription or earlier if the consumer had previously filled a prescription at the pharmacy. The BIN/PCN identifies the APBM such that when the pharmacy system 604 transmits a request for a prescription claim, through the eRx Network™ 606, the rRx Network™ recognizes based on the BIN/PCN that it is to forward the request and accompanying data packet or file to the APBM 200. The ABPM 200 therefore receives a request for a prescription claim, from a particular pharmacy and via the eRx Network 606 (step 802 of FIG. 8). The APBM adjudicates the request based on the consumer's prescription benefit policy data, as stored by or accessible to the APBM, and the data file received from the pharmacy (step 804 of FIG. 8). In other words, the APBM 200 determines, based on the data included in the data packet or file received from the pharmacy as part of the request for the prescription claim, whether to authorize/approve the prescription claim, following some of the same steps that a claims processor would follow when adjudicating a prescription claim. It should be noted that the adjudicating process may be performed by the APBM 200 in circumstances in embodiments in which the consumer has not previously accepted an offer from the APBM 200 to have the prescription filled at this pharmacy, in which case the steps of adjudicating the claim (or similar steps, that comprise determining whether the consumer is eligible to fill the prescription with the particular drug identified in the data packet or file and at what Consumer Price) may have previously been performed when generating the offer for the consumer, as described above with reference to FIGS. 3A-3C. For example, the APBM 200 may (i) retrieve the consumer's records, based on a consumer identifying information included in the data packet, to determine whether the consumer has previously accepted an offer for this prescription to be filled at this pharmacy (e.g., an offer that had been output to the consumer after the APBM 200 followed a process such as process 300A, 300B or 300C described with respect to FIGS. 3A, 3B and 3C, respectively); or (ii) dynamically adjudicate the prescription claim upon receiving the data packet or file from the pharmacy by retrieving the consumer's healthcare or prescription plan data and following a process similar to process 300A, 300B or 300C described with respect to FIGS. 3A, 3B and 3C, respectively, in order to determine whether to approve the prescription being filled at this pharmacy and the corresponding Consumer Price.

Figure 8:
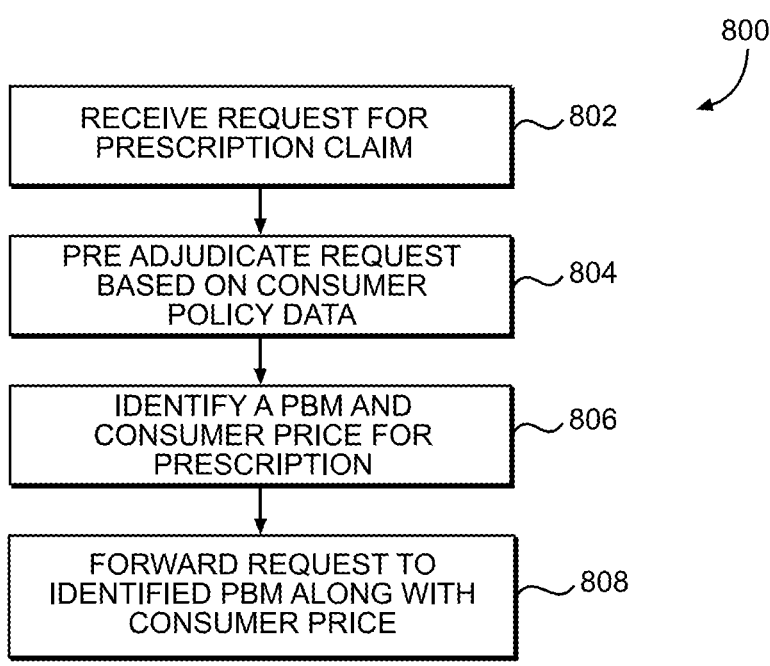
FIG. 8 comprises an example process flow diagram of another example process consistent with at least some embodiments described herein.

Thus, as part of the adjudicating process, the APBM 200 determines whether to fill the prescription based on a pricing contract that the APBM 200 has itself negotiated with the pharmacy 604 or based on a pricing contract of a PBM (i.e., a pricing contract that a particular PBM has negotiated with the pharmacy 604) and the Consumer Price for the prescription (step 806 of FIG. 8). If the prescription claim is for a prescription for which the consumer has previously accepted an offer, this may simply comprise determining the PBM corresponding to the pricing contract utilized to generate the offer (or that it was an APBM pricing contract that had been used to generate the offer).

If it is determined that the prescription should be filled based on a pricing contract of a PBM, the APBM 200 may then forward the request for the prescription claim to the PBM 608 corresponding to that pricing contract (step 808 of FIG. 8). Forwarding the request may comprise forwarding the data packet or file received from the pharmacy 604. In accordance with some embodiments, the APBM 200 may modify the data packet file, or certain fields thereof, such that additional or different information is included in the data packet (as compared to the data packet received from the pharmacy 604). For example, the APBM 200 may insert a unique transaction identifier and a Consumer Price (as determined by the APBM 200's pre-adjudication process that had been performed prior to determining to forwarding the prescription claim to the PBM) into the data packet, as well as an indication that the prescription claim has been approved/authorized. Additionally, the APBM may replace the BIN/PCN identifying the APBM 200 (as it was included in the request received from the pharmacy 604) with the BIN/PCN identifying the PBM 608 corresponding to the pricing contract being used to fill the prescription, such that the rRx Network™ 606 recognizes the appropriate PBM 608 to which the pre-adjudicated prescription claim is to be forwarded. The APBM 200 then forwards this modified data packet to the appropriate PBM 608 via the rRx Network™ 606. The APBM 200 may utilized a sub-routine or module, such as PBM Switchboard Module 232 (FIG. 2) to identify the PBM 608 to which the data packed comprising the request for a prescription claim should be routed, the particulars for modifying the data packet and/or for transmitting the data packet to the PBM 608 via the eRx Network™ 606.

Since the prescription claim, in the process illustrated in FIG. 6B, has been pre-adjudicated by the APBM 200 prior to being transmitted to the PBM 608, the internal process of PBM 608 may be much more minimal and efficient when processing requests for prescription claims received from APBM 200 than it would be for traditional requests for prescription claims that may be received directly from pharmacies via the eRx Network™ 606. For example, the PBM 608 need not adjudicate the prescription claim by retrieving the consumer's prescription plan data and determining whether to approve the prescription claim (e.g., based on whether the consumer is eligible under his/her current prescription benefit plan) or what the Consumer Price is to be. These determinations have been made by the APBM in pre-adjudicating the prescription claim and the results are included in the modified data packet transmitted to the PBM 608 by APBM 200. Thus, the PBM 608 need only forward the approval of the prescription claim to the pharmacy (and, in some embodiments, the Consumer Price), which approval communication may in some embodiments include the BIN/PCN of the PBM (rather than the BIN/PCN of the APBM using which the pharmacy initiated the request for the prescription claim in a current transaction). In some embodiments, the PBM 608 does not respond to the pharmacy 604 directly if the APBM 200 has already responded directly to the pharmacy with the approval of the prescription claim and the Consumer Price. The PBM 608 also stores in its own records an indication of the approved prescription claim (in association with the unique transaction identifier that had been assigned to the prescription claim by the APBM 200 or the eRx Network 606 and the Consumer Price), so that it can include the appropriate Pharmacy Reimbursement Amount (and, in some embodiments, transaction identifier) in a payment of Pharmacy Reimbursement Amounts and accompanying report that it at some later point sends to the pharmacy 604.

In some embodiments, the APBM 200 may respond to a request for a prescription claim received from a pharmacy 604 directly to the pharmacy (e.g., prior to or simultaneously with forwarding a modified data packet to a PBM 608), such that the pharmacy receives an indication of an approval of the claim and the Consumer Price without any potential delays. In such embodiments, the PBM 608 may also transmit a response to the pharmacy 604 to the same request for a prescription claim, once it receives the modified data packet from the APBM 200. As described above, in some embodiments the PBM 608 does not respond to the pharmacy 604 for the prescription claim if the APBM 200 has already done so.

Thus, as can be appreciated from comparing the data flow infrastructure of FIG. 6A (the traditional infrastructure) to that of FIG. 6B (Applicant's novel infrastructure), from a consumer and pharmacy perspective a prescription claim approval process appears much the same: (i) a request for a prescription claim is submitted via the eRx Network 606™ using a BIN/PCN of a consumer's prescription benefit plan indicator (whether it be the BIN/PCN of a PBM, as in FIG. 6A or the BIN/PCN of the APBM, as in FIG. 6B), along with other data normally included in such a request, such as a consumer identifier and an indication of the prescription drug that is to be used to fill the prescription, and (ii) an approval or denial of the prescription claim request is also received via the eRx Network™ 606, along with an indication of the Consumer Price that the consumer is to pay to the pharmacy. The fact that the processing of the request differs under the infrastructure of FIG. 6B is transparent to the pharmacy system 604. But this difference in the prescription claim processing allows the consumer to receive savings, and potentially additional rewards, by having the prescription be processed by the APBM 200 in accordance with embodiments described herein. Additionally, when it comes time for the pharmacy to be reimbursed the Pharmacy Reimbursement Amount it is expecting for filling the prescription, the payment is received by the pharmacy under its expected financial channels with PBMs (and with the APBM, for prescriptions that are filled using the APBM's pricing contract negotiated with the pharmacy), thus also minimizing any changes to the pharmacy's processes.

As noted below, there is a difference in the data that the pharmacy receives eventually from a prescription that is filled using a PBM to which the APBM routes a request, in that a given transaction identifier is associated with two different BIN/PCN identifiers (one for the APBM, to which the pharmacy submits the prescription claim, and one for the PBM that is responsible for paying the pharmacy the Pharmacy Reimbursement Amount). This, however, is a back-end data difference that may impact a financial audit or reconciliation process but not a front-end prescription claim approval process. Nevertheless, this different financial reconciliation process results in a new type of data being stored and utilized in reconciliation payments received from PBMs for prescriptions filled using the APBM BIN/PCN identifier. Process 700, described below, illustrates some example steps of one embodiment of such a reconciliation process.

Figure 7:
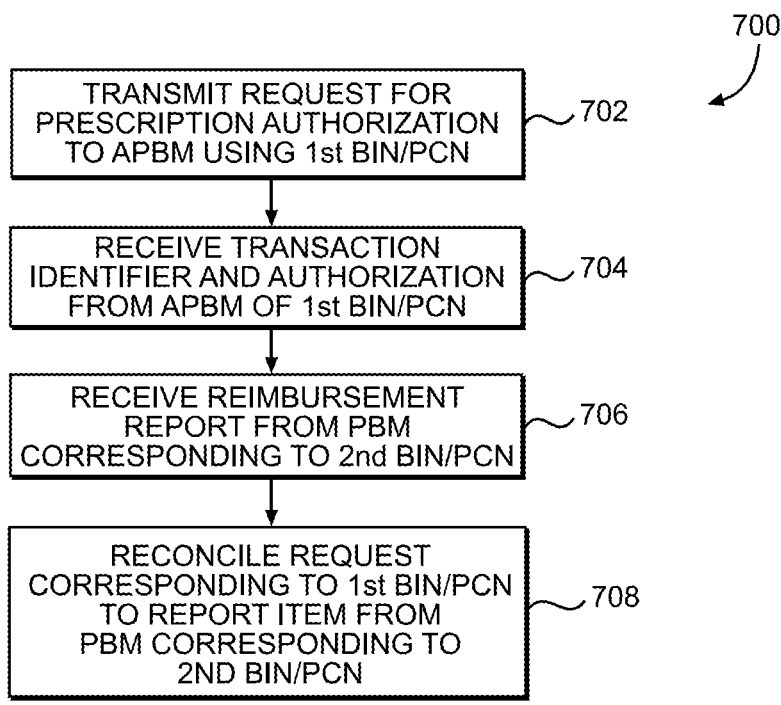
FIG. 7 comprises an example process flow diagram of an example process consistent with at least some embodiments described herein.

Turning now to FIG. 7, illustrated therein is an example process 700 that may be performed by a pharmacy of computer system of a pharmacy (e.g., a pharmacy system 502 of FIG. 5) in accordance with some embodiments (e.g., in the APBM-as-switchboard embodiment). Process 700 illustrates the unique steps and data that a pharmacy may process when reconciling claims processed via an APBM that were not necessary when processing claims that are approved under a traditional PBM process. In step 702, the pharmacy transmits a request for a prescription claim approval or authorization using a first BIN/PCN (the BIN/PCN identifying the APBM, as received from a consumer who is utilizing the APBM for filling his/her prescription). In response to this request, the pharmacy receives a response from the APBM (or, in some embodiments, from the PBM to which the APBM routes the request after modifying the data packet or file originally received from the pharmacy as part of the request). The response includes a unique transaction identifier that has been assigned to the request/transaction, by the APBM associated with the first BIN/PCN (alternatively, the transaction identifier may be assigned by a claim processor, eRx Network or another entity).

The particulars of what steps 702 and 704 may comprise (and the back-end processing that occurs in order for the prescription claim to be approved) has been described in detail with respect to FIG. 5 and FIG. 6B and will thus not be repeated for purposes of brevity.

The pharmacy may store in its records the transaction identifier, an indication that the prescription claim associated with the transaction identifier was approved and the first BIN/PCN identifier to which the request for approval of the prescription claim had been sent. At some later point in time (e.g., days or weeks later), in step 706, the pharmacy may receive a payment from a PBM, comprising Pharmacy Reimbursement Amounts for various approved prescription claims that had been approved and for which the PBM is responsible (known as an "835 remittance"). The payment may be accompanied by a report that details the particular Pharmacy Reimbursement Amounts that are included in the payment and the unique transaction identifier corresponding to each Pharmacy Reimbursement Amount (i.e., the transaction comprising an approved prescription claim to which a given Pharmacy Reimbursement Amount corresponds). This payment and accompanying report may be associated with a second BIN/PCN, corresponding to the PBM that is providing the payment and report. However, as noted in reference to step 702 (and also with reference to FIG. 5 and FIG. 6B), when the pharmacy first submitted the request for approval of the prescription claim to the eRx Network™ (in circumstances where the consumer is utilizing APBM for his/her prescriptions), the BIN/PCN it utilized was that of the APBM. However, in the pharmacy's records, the transaction identifier corresponding to the approved prescription claim (based on the response the pharmacy receives for the request) is associated with the first BIN/PCN identifying the APBM. Thus, using the unique transaction identifier of the prescription claim as received in response to the originally submitted request for approval, the pharmacy may reconcile that it has received the Pharmacy Reimbursement Amount as expected for a given prescription claim even though the payment it receives from a PBM associates it with a different BIN/PCN than had been originally associated with the prescription claim request (step 708).

RULES OF INTERPRETATION

Numerous embodiments have been described, and are presented for illustrative purposes only. The described embodiments are not intended to be limiting in any sense.

The invention is widely applicable to numerous embodiments, as is readily apparent from the disclosure herein. These embodiments are described in sufficient detail to enable those skilled in the art to practice the invention, and it is to be understood that other embodiments may be utilized and that structural, logical, software, electrical and other changes may be made without departing from the scope of the present invention. Accordingly, those skilled in the art will recognize that the present invention may be practiced with various modifications and alterations. Although particular features of the present invention may be described with reference to one or more particular embodiments or figures that form a part of the present disclosure, and in which are shown, by way of illustration, specific embodiments of the invention, it should be understood that such features are not limited to usage in the one or more particular embodiments or figures with reference to which they are described. The present disclosure is thus neither a literal description of all embodiments of the invention nor a listing of features of the invention that must be present in all embodiments.

The terms "an embodiment", "embodiment", "embodiments", "the embodiment", "the embodiments", "an embodiment", "some embodiments", "an example embodiment", "at least one embodiment", "one or more embodiments" and "one embodiment" mean "one or more (but not necessarily all) embodiments of the present invention(s)" unless expressly specified otherwise.

The terms "including", "comprising" and variations thereof mean "including but not limited to", unless expressly specified otherwise.

The term "consisting of" and variations thereof mean "including and limited to", unless expressly specified otherwise.

The enumerated listing of items does not imply that any or all of the items are mutually exclusive. The enumerated listing of items does not imply that any or all of the items are collectively exhaustive of anything, unless expressly specified otherwise. The enumerated listing of items does not imply that the items are ordered in any manner according to the order in which they are enumerated.

The term "comprising at least one of" followed by a listing of items does not imply that a component or subcomponent from each item in the list is required. Rather, it means that one or more of the items listed may comprise the item specified. For example, if it is said "wherein A comprises at least one of: a, b and c" it is meant that (i) A may comprise a, (ii) A may comprise b, (iii) A may comprise c, (iv) A may comprise a and b, (v) A may comprise a and c, (vi) A may comprise b and c, or (vii) A may comprise a, b and c.

The terms "a", "an" and "the" mean "one or more", unless expressly specified otherwise.

The term "based on" means "based at least on", unless expressly specified otherwise.

The methods described herein (regardless of whether they are referred to as methods, processes, algorithms, calculations, and the like) inherently include one or more steps. Therefore, all references to a "step" or "steps" of such a method have antecedent basis in the mere recitation of the term 'method' or a like term. Accordingly, any reference in a claim to a 'step' or 'steps' of a method is deemed to have sufficient antecedent basis.

Headings of sections provided in this document and the title are for convenience only, and are not to be taken as limiting the disclosure in any way.

Devices that are in communication with each other need not be in continuous communication with each other, unless expressly specified otherwise. In addition, devices that are in communication with each other may communicate directly or indirectly through one or more intermediaries.

A description of an embodiment with several components in communication with each other does not imply that all such components are required, or that each of the disclosed components must communicate with every other component. On the contrary a variety of optional components are described to illustrate the wide variety of possible embodiments of the present invention.

Further, although process steps, method steps, algorithms or the like may be described in a sequential order, such processes, methods and algorithms may be configured to work in alternate orders. In other words, any sequence or order of steps that may be described in this document does not, in and of itself, indicate a requirement that the steps be performed in that order. The steps of processes described herein may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to the invention, and does not imply that the illustrated process is preferred.

It will be readily apparent that the various methods and algorithms described herein may be implemented by, e.g., appropriately programmed general purpose computers and computing devices. Typically a processor (e.g., a microprocessor or controller device) will receive instructions from a memory or like storage device, and execute those instructions, thereby performing a process defined by those instructions. Further, programs that implement such methods and algorithms may be stored and transmitted using a variety of known media.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article.

The functionality and/or the features of a device may be alternatively embodied by one or more other devices which are not explicitly described as having such functionality/features. Thus, other embodiments of the present invention need not include the device itself.

The term "computer-readable medium" as used herein refers to any medium that participates in providing data (e.g., instructions) that may be read by a computer, a processor or a like device. Such a medium may take many forms, including but not limited to, non-volatile media, volatile media, and transmission media. Non-volatile media include, for example, optical or magnetic disks and other persistent memory. Volatile media may include dynamic random access memory (DRAM), which typically constitutes the main memory. Transmission media may include coaxial cables, copper wire and fiber optics, including the wires or other pathways that comprise a system bus coupled to the processor. Transmission media may include or convey acoustic waves, light waves and electromagnetic emissions, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, a carrier wave as described hereinafter, or any other medium from which a computer can read.

Various forms of computer readable media may be involved in carrying sequences of instructions to a processor. For example, sequences of instruction (i) may be delivered from RAM to a processor, (ii) may be carried over a wireless transmission medium, and/or (iii) may be formatted according to numerous formats, standards or protocols, such as Transmission Control Protocol, Internet Protocol (TCP/IP), Wi-Fi, Bluetooth, TDMA, CDMA, and 3G.

Where databases are described, it will be understood by one of ordinary skill in the art that (i) alternative database structures to those described may be readily employed, and (ii) other memory structures besides databases may be readily employed. Any schematic illustrations and accompanying descriptions of any sample databases presented herein are illustrative arrangements for stored representations of information. Any number of other arrangements may be employed besides those suggested by the tables shown. Similarly, any illustrated entries of the databases represent exemplary information only; those skilled in the art will understand that the number and content of the entries can be different from those illustrated herein. Further, despite any depiction of the databases as tables, other formats (including relational databases, object-based models and/or distributed databases) could be used to store and manipulate the data types described herein.

Likewise, object methods or behaviors of a database can be used to implement the processes of the present invention. In addition, the databases may, in a known manner, be stored locally or remotely from a device that accesses data in such a database.

For example, as an example alternative to a database structure for storing information, a hierarchical electronic file folder structure may be used. A program may then be used to access the appropriate information in an appropriate file folder in the hierarchy based on a file path named in the program.

It should also be understood that, to the extent that any term recited in the claims is referred to elsewhere in this document in a manner consistent with a single meaning, that is done for the sake of clarity only, and it is not intended that any such term be so restricted, by implication or otherwise, to that single meaning.

In a claim, a limitation of the claim which includes the phrase "means for" or the phrase "step for" means that 35 U.S.C. § 112, paragraph 6, applies to that limitation.

In a claim, a limitation of the claim which does not include the phrase "means for" or the phrase "step for" means that 35 U.S.C. § 112, paragraph 6 does not apply to that limitation, regardless of whether that limitation recites a function without recitation of structure, material or acts for performing that function. For example, in a claim, the mere use of the phrase "step of" or the phrase "steps of" in referring to one or more steps of the claim or of another claim does not mean that 35 U.S.C. § 112, paragraph 6, applies to that step(s).

With respect to a means or a step for performing a specified function in accordance with 35 U.S.C. § 112, paragraph 6, the corresponding structure, material or acts described in the specification, and equivalents thereof, may perform additional functions as well as the specified function.

Computers, processors, computing devices and like products are structures that can perform a wide variety of functions. Such products can be operable to perform a specified function by executing one or more programs, such as a program stored in a memory device of that product or in a memory device which that product accesses. Unless expressly specified otherwise, such a program need not be based on any particular algorithm, such as any particular algorithm that might be disclosed in the present application. It is well known to one of ordinary skill in the art that a specified function may be implemented via different algorithms, and any of a number of different algorithms would be a mere design choice for carrying out the specified function.

Therefore, with respect to a means or a step for performing a specified function in accordance with 35 U.S.C. § 112, paragraph 6, structure corresponding to a specified function includes any product programmed to perform the specified function. Such structure includes programmed products which perform the function, regardless of whether such product is programmed with (i) a disclosed algorithm for performing the function, (ii) an algorithm that is similar to a disclosed algorithm, or (iii) a different algorithm for performing the function.

While various embodiments have been described herein, it should be understood that the scope of the present invention is not limited to the particular embodiments explicitly described. Many other variations and embodiments would be understood by one of ordinary skill in the art upon reading the present description.

What is claimed is:

1. A system for routing pharmacy prescription fulfillment requests, the system comprising:
    a processor;
    a non-transitory memory storing a program, the processor operable with the program to:
    (a) receive, at a device functioning as an alternative pharmacy benefit manager (APBM) and from a pharmacy device via a prescription processing computer network dedicated to processing requests for fulfillment of pharmaceutical prescriptions, a first data, the first data comprising (i) a request for fulfillment of a prescription at a pharmacy corresponding to the pharmacy device; (ii) a first BIN/PCN identifier that had caused the pharmacy to transmit the first data to the system, and (iii) a user identifier identifying a user associated with the request;
    (b) select one of the following options: (i) fulfilling the prescription based on a first pricing contract previously established with the pharmacy; and (ii) utilizing at least one second pricing contract of at least one of a plurality of third party pharmacy benefit managers for fulfillment of the prescription;
    (c) only if option (ii) in (b) is selected, perform (d)—(f), otherwise utilize the first pricing contract for fulfillment of the prescription without transmitting the first data to any of the plurality of third party pharmacy benefit managers for fulfillment of the prescription;
    (d) identify one of the plurality of third party pharmacy benefit managers, for the fulfillment of the prescription;
    (e) modify the first data by replacing the first BIN/PCN identifier with a second BIN/PCN identifier that corresponds to the one of the plurality of third party pharmacy benefit managers identified for fulfillment of the prescription, thereby generating a modified first data; and
    (f) transmit, via the prescription processing computer network, the modified first data to a device of the one of the plurality of third party pharmacy benefit managers identified for fulfillment of the prescription.

2. The system of claim 1, wherein the processor is further operable with the program to:
    adjudicate the request for the fulfillment of the prescription in order to verify that the prescription is authorized to be redeemed by the user at the pharmacy; and
    further modify the first data by including in the modified first data that is transmitted to the one of the plurality of third party pharmacy benefit managers an indication that the prescription is authorized to be redeemed by the user at the pharmacy.

3. The system of claim 2, wherein the processor being operable with the program to adjudicate the request comprises the processor being operable with the program to:
    retrieve information corresponding to a pharmacy benefit plan of which the user is a member; and
    verify that the fulfillment of the prescription by the user at the pharmacy is within at least one rule of the pharmacy benefit plan.

4. The system of claim 1, wherein the processor is further operable with the program to:
    determine an out of pocket cost to be paid by the user for the fulfillment of the prescription at the pharmacy; and
    further modify the first data by including in the modified first data that is transmitted to the one of the plurality of third party pharmacy benefit managers an indication of the out of pocket cost.

5. The system of claim 4, wherein the processor is further operable with the program to:
    charge the out of pocket cost to a financial account associated with the user.

6. The system of claim 1, wherein the processor is further operable with the program to:
    determine a reward to be provided to the user for the fulfillment of the prescription at the pharmacy; and
    cause the reward to be provided to the user.

7. The system of claim 6, wherein the processor is further operable with the program to:
    determine that the reward to be provided to the user comprises a payment to be made to the user by the pharmacy; and
    wherein modifying the first data comprises adding to the first data an indication of the payment to be provided to the user by the pharmacy upon a fulfillment of the prescription.

8. The system of claim 1, wherein the processor being operable with the program to select one of a plurality of third party pharmacy benefit managers comprises:
    retrieving, from a database, the one of the plurality of third party pharmacy benefit managers identified for the fulfillment of the prescription by the user prior to receiving the first data.

9. The system of claim 1, wherein the processor being operable with the program to select the one of the plurality of third party pharmacy benefit managers comprises:
    identifying, after receiving the first data, a set of available prices for the prescription, each price of the set of prices corresponding to a different one of the plurality of third party pharmacy benefit managers; and selecting the different one of the plurality of third party pharmacy benefit managers that corresponds to a price satisfying at least one criteria.

10. A non-transitory computer-readable medium storing instructions for directing a processor to perform a process, the process comprising:
    (a) receiving, at a device functioning as an alternative pharmacy benefit manager (APBM) and from a pharmacy device via a prescription processing computer network dedicated to processing requests for fulfillment of pharmaceutical prescriptions, a first data, the first data comprising (i) a request for fulfillment of a prescription at a pharmacy corresponding to the pharmacy device; (ii) a first BIN/PCN identifier that had caused the pharmacy to transmit the first data to the system, and (iii) a user identifier identifying a user associated with the request;
    (b) selecting one of the following options: (i) fulfilling the prescription based on a first pricing contract previously established with the pharmacy; and (ii) utilizing at least one second pricing contract of at least one of a plurality of third party pharmacy benefit managers for fulfillment of the prescription;
    (c) only if option (ii) in (b) is selected, performing (d)—(f), otherwise utilize the first pricing contract for fulfillment of the prescription without transmitting the first data to any of the plurality of third party pharmacy benefit managers for fulfillment of the prescription;
    (d) identifying one of the plurality of third party pharmacy benefit managers, for the fulfillment of the prescription;
    (e) modifying the first data by replacing the first BIN/PCN identifier with a second BIN/PCN identifier that corresponds to one of the plurality of third party pharmacy benefit managers identified for fulfillment of the prescription, thereby generating a modified first data; and
    (f) transmitting, via the prescription processing computer network, the modified first data to a device of the one of the plurality of third party pharmacy benefit managers identified for fulfillment of the prescription.

11. The non-transitory computer-readable medium of claim 10, wherein the process further comprises:
    adjudicating the request for the fulfillment of the prescription in order to verify that the prescription is authorized to be redeemed by the user at the pharmacy; and
    further modifying the first data by including in the modified first data that is transmitted to the one of the plurality of third party pharmacy benefit managers an indication that the prescription is authorized to be redeemed by the user at the pharmacy.

12. The non-transitory computer-readable medium of claim 11, wherein the process further comprises:
    retrieving information corresponding to a pharmacy benefit plan of which the user is a member; and
    verifying that the fulfillment of the prescription by the user at the pharmacy is within at least one rule of the pharmacy benefit plan.

13. The non-transitory computer-readable medium of claim wherein the process further comprises:
    determining an out of pocket cost to be paid by the user for the fulfillment of the prescription at the pharmacy; and
    further modifying the first data by including in the modified first data that is transmitted to the one of the plurality of third party pharmacy benefit managers an indication of the out of pocket cost.

14. The non-transitory computer-readable medium of claim wherein the process further comprises:
    determining a reward to be provided to the user for the fulfillment of the prescription at the pharmacy; and
    causing the reward to be provided to the user.

15. The non-transitory computer-readable medium of claim 14, wherein the process further comprises:
    determining that the reward to be provided to the user comprises a payment to be made to the user by the pharmacy; and
    wherein modifying the first data comprises adding to the first data an indication of the payment to be provided to the user by the pharmacy upon a fulfillment of the prescription.

16. The non-transitory computer-readable medium of claim 15, wherein the process further comprises:
    retrieving, from a database, the one of the plurality of third party pharmacy benefit managers identified for the fulfillment of the prescription by the user prior to receiving the first data.

17. The non-transitory computer-readable medium of claim 10, wherein the process further comprises:
    charging the out of pocket cost to a financial account associated with the user.

* * * * *